(12) United States Patent
Barnhill et al.

(10) Patent No.: US 8,146,613 B2
(45) Date of Patent: Apr. 3, 2012

(54) WASH CHAMBER FOR SURGICAL ENVIRONMENT

(75) Inventors: Paul R. Barnhill, Aurora, CO (US); James Glenn, Denver, CO (US); Kathy Lockridge, Littleton, CO (US); Jeff Heng, Morrison, CO (US)

(73) Assignee: Resurgent Health & Medical, LLC, Golden, CO (US)

( * ) Notice: Subject to any disclaimer, the term of this patent is extended or adjusted under 35 U.S.C. 154(b) by 277 days.

(21) Appl. No.: 12/432,718

(22) Filed: Apr. 29, 2009

(65) Prior Publication Data
US 2009/0301523 A1 Dec. 10, 2009

Related U.S. Application Data

(60) Provisional application No. 61/048,924, filed on Apr. 29, 2008, provisional application No. 61/097,715, filed on Sep. 17, 2008, provisional application No. 61/097,723, filed on Sep. 17, 2008, provisional application No. 61/097,736, filed on Sep. 17, 2008, provisional application No. 61/097,704, filed on Sep. 17, 2008, provisional application No. 61/058,521, filed on Jun. 3, 2008, provisional application No. 61/112,120, filed on Nov. 6, 2008.

(51) Int. Cl.
*B08B 3/06* (2006.01)

(52) U.S. Cl. ........ 134/119; 134/117; 134/175; 134/177; 134/199

(58) Field of Classification Search .................. 134/117, 134/118, 119, 175, 177, 182, 199, 201
See application file for complete search history.

(56) References Cited

U.S. PATENT DOCUMENTS

| | | |
|---|---|---|
| 2,325,008 A | 7/1943 | Gruett |
| 2,386,455 A | 10/1945 | Green |
| 2,522,928 A | 9/1950 | Carroll |
| 2,647,801 A | 8/1953 | Lycan |
| 2,769,547 A | 11/1956 | Hirsch |
| 2,789,865 A | 4/1957 | Shannon |
| 2,826,763 A | 3/1958 | Bass |
| 2,896,856 A | 7/1959 | Kravits |
| 3,059,815 A | 10/1962 | Parsons, Jr. |

(Continued)

FOREIGN PATENT DOCUMENTS
DE 19903079 8/2000
(Continued)

OTHER PUBLICATIONS

Official Action for U.S. Appl. No. 12/432,693, mailed Sep. 21, 2011.
(Continued)

*Primary Examiner* — Michael Barr
*Assistant Examiner* — Saeed T Chaudhry
(74) *Attorney, Agent, or Firm* — Sheridan Ross P.C.

(57) ABSTRACT

A system and method for a surgical scrub automated cleaning station are disclosed. The surgical scrub cylinder automated cleaning station includes a rotatable, extendable, and retractable wash cylinder that is operable to accommodate any variety of arm length. More specifically, the surgical scrub automated cleaning station may include an accordion, telescoping, or otherwise adjustable cylinder to accommodate a variety of arm lengths. The surgical scrub cylinder automated cleaning station may be used to provide a surgeon or other health care personnel with a hand and forearm washing. The surgical scrub cylinder automated cleaning station may also be monitored to ensure compliance with one or more hygiene protocols.

4 Claims, 64 Drawing Sheets

U.S. PATENT DOCUMENTS

| | | |
|---|---|---|
| 3,081,471 A | 3/1963 | Newell |
| 3,220,424 A | 11/1965 | Nelson |
| 3,243,264 A | 3/1966 | Hickey |
| 3,437,274 A | 4/1969 | Apri |
| 3,529,774 A | 9/1970 | Apri |
| 3,639,844 A | 2/1972 | Karklys |
| 3,647,147 A | 3/1972 | Cook |
| 3,699,984 A | 10/1972 | Davis |
| 3,744,149 A | 7/1973 | Helbling |
| 3,754,559 A | 8/1973 | Seiwert |
| 3,757,806 A | 9/1973 | Baaskar et al. |
| 3,817,651 A | 6/1974 | Law et al. |
| 3,844,278 A | 10/1974 | Weider |
| 3,881,328 A | 5/1975 | Kleimola et al. |
| 3,918,117 A | 11/1975 | Plante |
| 3,918,987 A | 11/1975 | Kopfer |
| 3,967,478 A | 7/1976 | Guinn |
| 3,992,730 A | 11/1976 | Davis |
| 3,997,873 A | 12/1976 | Thornton |
| 4,001,599 A | 1/1977 | Karklys |
| 4,020,856 A | 5/1977 | Masterson |
| 4,073,301 A | 2/1978 | Mackinnon |
| 4,120,180 A | 10/1978 | Jedora |
| 4,137,929 A | 2/1979 | Grossman |
| 4,219,367 A | 8/1980 | Cary, Jr. et al. |
| 4,275,385 A | 6/1981 | White |
| 4,295,233 A | 10/1981 | Hinkel et al. |
| 4,398,310 A | 8/1983 | Lienhard |
| 4,402,331 A | 9/1983 | Taldo et al. |
| 4,453,286 A | 6/1984 | Wieland |
| 4,496,519 A | 1/1985 | McGuire |
| 4,509,543 A | 4/1985 | Livingston et al. |
| 4,601,064 A | 7/1986 | Shipley |
| 4,606,085 A | 8/1986 | Davies |
| 4,606,500 A | 8/1986 | Mussler et al. |
| 4,670,010 A | 6/1987 | Dragone |
| 4,688,585 A | 8/1987 | Vetter |
| 4,769,863 A | 9/1988 | Tegg et al. |
| 4,817,651 A * | 4/1989 | Crisp et al. ................ 134/102.1 |
| 4,896,144 A | 1/1990 | Bogstad |
| 4,916,435 A | 4/1990 | Fuller |
| 4,921,211 A | 5/1990 | Novak et al. |
| 4,925,495 A | 5/1990 | Crisp et al. |
| 4,942,631 A | 7/1990 | Rosa |
| 4,999,613 A | 3/1991 | Williamson et al. |
| 5,016,172 A | 5/1991 | Dessertine |
| 5,031,258 A | 7/1991 | Shaw |
| 5,060,323 A | 10/1991 | Shaw |
| 5,074,322 A | 12/1991 | Jaw |
| RE33,810 E | 2/1992 | Strieter |
| 5,086,526 A | 2/1992 | Van Marcke |
| 5,119,104 A | 6/1992 | Heller |
| 5,184,642 A | 2/1993 | Powell |
| 5,193,563 A | 3/1993 | Melech |
| 5,199,118 A | 4/1993 | Cole et al. |
| 5,202,666 A | 4/1993 | Knippscheer |
| 5,238,749 A | 8/1993 | Cueman et al. |
| 5,257,423 A | 11/1993 | Jacobsen et al. |
| 5,265,628 A | 11/1993 | Sage et al. |
| 5,291,399 A | 3/1994 | Chaco |
| 5,340,581 A | 8/1994 | Tseng et al. |
| 5,387,993 A | 2/1995 | Heller et al. |
| RE35,035 E | 9/1995 | Shipley |
| 5,455,851 A | 10/1995 | Chaco et al. |
| 5,465,082 A | 11/1995 | Chaco |
| 5,503,840 A | 4/1996 | Jacobson et al. |
| 5,515,426 A | 5/1996 | Yacenda et al. |
| 5,548,637 A | 8/1996 | Heller et al. |
| 5,561,412 A | 10/1996 | Novak et al. |
| 5,572,195 A | 11/1996 | Heller et al. |
| 5,594,786 A | 1/1997 | Chaco et al. |
| 5,601,100 A | 2/1997 | Kawakami et al. |
| 5,610,589 A | 3/1997 | Evans et al. |
| 5,633,742 A | 5/1997 | Shipley |
| 5,670,945 A | 9/1997 | Applonie |
| 5,689,229 A | 11/1997 | Chaco et al. |
| 5,695,091 A | 12/1997 | Winings et al. |
| 5,699,038 A | 12/1997 | Ulrich et al. |
| 5,702,115 A | 12/1997 | Pool |
| 5,727,579 A | 3/1998 | Chardack |
| 5,745,272 A | 4/1998 | Shipley |
| 5,765,242 A | 6/1998 | Marciano |
| 5,774,865 A | 6/1998 | Glynn |
| 5,781,942 A | 7/1998 | Allen et al. |
| 5,793,653 A | 8/1998 | Segal |
| 5,808,553 A | 9/1998 | Cunningham |
| 5,812,059 A | 9/1998 | Shaw et al. |
| 5,818,617 A | 10/1998 | Shipley |
| 5,822,418 A | 10/1998 | Yacenda et al. |
| 5,822,544 A | 10/1998 | Chaco et al. |
| 5,823,447 A | 10/1998 | Maybach |
| 5,838,223 A | 11/1998 | Gallant et al. |
| 5,845,225 A | 12/1998 | Mosher |
| 5,860,437 A | 1/1999 | Fernie |
| 5,863,497 A | 1/1999 | Dirksing |
| 5,870,015 A | 2/1999 | Hinkel |
| 5,900,067 A | 5/1999 | Jones |
| 5,900,801 A | 5/1999 | Heagle et al. |
| 5,924,148 A | 7/1999 | Flowers, Sr. |
| 5,939,974 A | 8/1999 | Heagle et al. |
| 5,945,068 A | 8/1999 | Ferone |
| 5,945,910 A | 8/1999 | Gorra |
| 5,952,924 A | 9/1999 | Evans et al. |
| 5,954,069 A | 9/1999 | Foster |
| 5,966,573 A | 10/1999 | Yu et al. |
| 5,966,753 A | 10/1999 | Gauthier et al. |
| 5,972,126 A | 10/1999 | Fernie |
| 5,979,500 A | 11/1999 | Jahrling et al. |
| 5,992,430 A | 11/1999 | Chardack et al. |
| 6,029,600 A | 2/2000 | Davis |
| 6,031,461 A | 2/2000 | Lynn |
| 6,037,871 A | 3/2000 | Babylon |
| 6,038,331 A | 3/2000 | Johnson |
| 6,038,519 A | 3/2000 | Gauthier et al. |
| 6,110,292 A | 8/2000 | Jewett et al. |
| 6,125,482 A | 10/2000 | Foster |
| 6,131,587 A | 10/2000 | Chardack et al. |
| 6,147,607 A | 11/2000 | Lynn |
| 6,161,227 A | 12/2000 | Bargenquast |
| 6,176,941 B1 | 1/2001 | Jewett et al. |
| 6,195,588 B1 | 2/2001 | Gauthier et al. |
| 6,211,788 B1 | 4/2001 | Lynn et al. |
| 6,232,870 B1 | 5/2001 | Garber et al. |
| 6,235,351 B1 | 5/2001 | DiMarzio et al. |
| 6,236,317 B1 | 5/2001 | Cohen et al. |
| 6,236,953 B1 | 5/2001 | Segal |
| 6,268,797 B1 | 7/2001 | Berube et al. |
| 6,278,372 B1 | 8/2001 | Velasco, Jr. et al. |
| 6,317,717 B1 | 11/2001 | Lindsey et al. |
| 6,335,686 B1 | 1/2002 | Goff et al. |
| 6,344,794 B1 | 2/2002 | Ulrich et al. |
| 6,351,866 B1 | 3/2002 | Bragulla |
| 6,392,546 B1 | 5/2002 | Smith |
| 6,399,853 B1 | 6/2002 | Roe et al. |
| 6,404,837 B1 | 6/2002 | Thompson et al. |
| 6,413,921 B1 | 7/2002 | Childers et al. |
| 6,417,773 B1 | 7/2002 | Vlahos et al. |
| 6,424,262 B2 | 7/2002 | Garber et al. |
| 6,426,701 B1 | 7/2002 | Levy et al. |
| 6,431,189 B1 | 8/2002 | Deibert |
| 6,448,886 B2 | 9/2002 | Garber et al. |
| 6,462,656 B2 | 10/2002 | Ulrich et al. |
| 6,486,780 B1 | 11/2002 | Garber et al. |
| 6,523,193 B2 | 2/2003 | Saraya |
| 6,524,390 B1 | 2/2003 | Jones |
| 6,539,393 B1 | 3/2003 | Kabala |
| 6,542,568 B1 | 4/2003 | Howes, Jr. et al. |
| 6,577,240 B2 | 6/2003 | Armstrong |
| 6,600,420 B2 | 7/2003 | Goff et al. |
| 6,663,719 B2 | 12/2003 | Shinozaki et al. |
| 6,671,890 B2 | 1/2004 | Nishioka |
| 6,706,243 B1 | 3/2004 | Sias et al. |
| 6,707,873 B2 | 3/2004 | Thompson et al. |
| 6,727,818 B1 | 4/2004 | Wildman et al. |
| 6,733,595 B1 | 5/2004 | Grillo |
| 6,759,959 B2 | 7/2004 | Wildman |
| 6,768,419 B2 | 7/2004 | Garber et al. |

| | | |
|---|---|---|
| 6,825,763 B2 | 11/2004 | Ulrich et al. |
| 6,832,916 B2 | 12/2004 | Collopy |
| 6,882,278 B2 | 4/2005 | Winings et al. |
| 6,883,563 B2 | 4/2005 | Smith |
| 6,892,143 B2 | 5/2005 | Howes, Jr. et al. |
| 6,902,397 B2 | 6/2005 | Farrell et al. |
| 6,938,282 B2 | 9/2005 | Yamamoto |
| 6,956,498 B1 | 10/2005 | Gauthier et al. |
| 6,970,574 B1 | 11/2005 | Johnson |
| D512,648 S | 12/2005 | Smith et al. |
| 6,975,231 B2 | 12/2005 | Lane et al. |
| 6,992,561 B2 | 1/2006 | Sandt et al. |
| 7,010,369 B2 | 3/2006 | Borders et al. |
| 7,015,816 B2 | 3/2006 | Wildman et al. |
| 7,020,508 B2 | 3/2006 | Stivoric et al. |
| 7,080,061 B2 | 7/2006 | Kabala |
| 7,107,631 B2 | 9/2006 | Lang et al. |
| 7,113,094 B2 | 9/2006 | Garber et al. |
| 7,119,688 B2 | 10/2006 | Wildman |
| 7,120,800 B2 | 10/2006 | Ginter et al. |
| 7,123,151 B2 | 10/2006 | Garber et al. |
| 7,150,293 B2 | 12/2006 | Jonte |
| 7,174,577 B2 | 2/2007 | Jost et al. |
| 7,242,306 B2 | 7/2007 | Wildman et al. |
| 7,242,307 B1 | 7/2007 | LeBlond et al. |
| 7,248,933 B2 | 7/2007 | Wildman |
| 7,270,268 B2 | 9/2007 | Garber et al. |
| 7,271,719 B2 | 9/2007 | Ku et al. |
| 7,271,728 B2 | 9/2007 | Taylor et al. |
| 7,293,645 B2 | 11/2007 | Harper et al. |
| 7,408,470 B2 | 8/2008 | Wildman et al. |
| 7,423,533 B1 | 9/2008 | LeBlond et al. |
| 7,443,305 B2 | 10/2008 | Verdiramo |
| 2002/0019709 A1 | 2/2002 | Segal |
| 2002/0104083 A1 | 8/2002 | Hendricks et al. |
| 2002/0135486 A1 | 9/2002 | Brohagen et al. |
| 2002/0175182 A1 | 11/2002 | Matthews |
| 2003/0069815 A1 | 4/2003 | Eisenberg et al. |
| 2003/0089771 A1 | 5/2003 | Cybulski et al. |
| 2003/0197122 A1 | 10/2003 | Faiola et al. |
| 2004/0083547 A1 | 5/2004 | Mercier |
| 2004/0133081 A1 | 7/2004 | Teller et al. |
| 2004/0255409 A1 | 12/2004 | Hilscher et al. |
| 2005/0134465 A1 | 6/2005 | Rice et al. |
| 2005/0136949 A1 | 6/2005 | Barnes |
| 2005/0139239 A1 | 6/2005 | Prae |
| 2005/0147526 A1 | 7/2005 | Hishida |
| 2005/0151641 A1 | 7/2005 | Ulrich et al. |
| 2005/0171634 A1 | 8/2005 | York et al. |
| 2005/0248461 A1 | 11/2005 | Lane et al. |
| 2006/0122474 A1 | 6/2006 | Teller et al. |
| 2006/0192001 A1 | 8/2006 | Shaffer et al. |
| 2006/0224051 A1 | 10/2006 | Teller et al. |
| 2006/0229891 A1 | 10/2006 | Grier |
| 2006/0231568 A1 | 10/2006 | Lynn et al. |
| 2006/0241396 A1 | 10/2006 | Fabian et al. |
| 2006/0264730 A1 | 11/2006 | Stivoric et al. |
| 2007/0011893 A1 | 1/2007 | Garber et al. |
| 2007/0020212 A1 | 1/2007 | Bernal et al. |
| 2007/0247316 A1 | 10/2007 | Wildman et al. |
| 2007/0257803 A1 | 11/2007 | Munro et al. |
| 2007/0273525 A1 | 11/2007 | Garber et al. |
| 2008/0001763 A1 | 1/2008 | Raja et al. |
| 2008/0031838 A1 | 2/2008 | Bolling |
| 2008/0099043 A1 | 5/2008 | Barnhill |
| 2008/0099045 A1 | 5/2008 | Glenn |
| 2008/0099046 A1 | 5/2008 | Barnhill |
| 2008/0099047 A1 | 5/2008 | Barnhill |
| 2008/0099048 A1 | 5/2008 | Barnhill |
| 2008/0099049 A1 | 5/2008 | Barnhill |
| 2008/0099050 A1 | 5/2008 | Barnhill |
| 2008/0100441 A1 | 5/2008 | Prodanovich |
| 2008/0103636 A1 | 5/2008 | Glenn |
| 2009/0083970 A1 | 4/2009 | Barnhill et al. |
| 2009/0084407 A1 | 4/2009 | Glenn et al. |
| 2009/0084414 A1 | 4/2009 | Barnhill et al. |
| 2009/0084417 A1 | 4/2009 | Barnhill et al. |
| 2009/0090389 A1 | 4/2009 | Barnhill et al. |
| 2009/0090390 A1 | 4/2009 | Barnhill et al. |
| 2009/0094814 A1 | 4/2009 | Barnhill et al. |
| 2009/0107528 A1 | 4/2009 | Barnhill et al. |
| 2010/0095983 A1 | 4/2010 | Barnhill et al. |
| 2010/0097224 A1 | 4/2010 | Prodanovich et al. |
| 2010/0313916 A1 | 12/2010 | Barnhill |
| 2010/0326472 A1 | 12/2010 | Glenn |

FOREIGN PATENT DOCUMENTS

| | | |
|---|---|---|
| EP | 0396039 | 11/1990 |
| EP | 0616658 | 9/1994 |
| EP | 0758702 | 2/1997 |
| EP | 1872802 | 1/2008 |
| EP | 1935515 | 6/2008 |
| FR | 2659217 | 9/1991 |
| GB | 2324397 | 10/1998 |
| JP | 5-329065 | 12/1993 |
| WO | WO 80/01983 | 10/1980 |
| WO | WO 93/10311 | 5/1993 |
| WO | WO 03/086274 | 10/2003 |

OTHER PUBLICATIONS

Official Action for U.S. Appl. No. 12/432,711, mailed Sep. 29, 2011.
Official Action for U.S. Appl. No. 12/432,716, mailed Sep. 29, 2011.
U.S. Appl. No. 13/164,577, filed Jun. 20, 2011, Barnhill et al.
U.S. Appl. No. 13/243,461, filed Sep. 23, 2011, Barnhill et al.
Plus Search Results for U.S. Appl. No. 11/852,099, searched Apr. 26, 2010.
U.S. Appl. No. 12/643,786, filed Dec. 21, 2009, Glenn et al.
"HandGiene" available at http://handgienecorp.com/index.jsp, printed Nov. 2, 2009, pp. 1-2.
International Preliminary Report on Patentability for International (PCT) Patent Application No. PCT/US09/42174, mailed Nov. 11, 2010.
U.S. Appl. No. 12/432,693, filed Apr. 29, 2009, Barnhill.
U.S. Appl. No. 12/432,698, filed Apr. 29, 2009, Barnhill et al.
U.S. Appl. No. 12/432,711, filed Apr. 29, 2009, Glenn, et al.
U.S. Appl. No. 12/432,716, filed Apr. 29, 2009, Barnhill.
"Case Study: FL hospital used IT to monitor hand washing", FierceHealthIT website, dated Aug. 3, 2009, available at http://www.fiercehealthit.com/node/8503/print, printed on Aug. 11, 2009, p. 1.
"Michigan IT Companies Helping the University of Miami Center for Patient Safety Tackle a Leading Cause of Death Using an RTLS Solution to Monitor Staff Hand-Washing Compliance", prnewswire website, dated Jul. 29, 2009, available at http://news.prnewswire.com/DisplayReleaseContent.aspx?ACCT=104&STORY=/www/story/07-29-2009/0005068398&EDATE, printed on Aug. 10, 2009, pp. 1-2.
"HyGreen: How it Works",available at http://www.xhale.com/hygreen/solution/How.asp,printed Jul. 14, 2009, pp. 1-2.
"HyGreen: Sample Reporting",available at http://www.xhale.com/hygreen/solution/Reporting.asp,printed Jul. 14, 2009, pp. 1-3.
International Search Report for International (PCT) Patent Application No. PCT/US09/42174, mailed Aug. 19, 2009.
Written Opinion for International (PCT) Patent Application No. PCT/US09/42174, mailed Aug. 19, 2009.

* cited by examiner

Cleaning Station-Use Record

| Employee Name | Time Stamp | Duration | Date | Compliance |
|---|---|---|---|---|
| Janet Smith | 08:00:00 a.m. | 10 secs | 5/21/2006 | Y |
| Bill Powers | 09:00:23 a.m. | 5 secs | 5/21/2006 | N |
| Jason Williams | 10:07:40 a.m. | 12 secs | 5/21/2006 | Y |
| Judy Jones | 11:10:05 a.m. | 11 secs | 5/21/2006 | Y |
| Sandra Collins | 11:20:31 a.m. | 6 secs | 5/21/2006 | N |

*Fig. 4*

Employee Record 340

| Employee Name | Hand Washing Statistics | Current Training Segment | Preferred Entertainment Content | Allergy |
|---|---|---|---|---|
| Sandra Collins | 94% | 3 | Sport | None |
| Bill Forbes | 97% | 5 | News | Solution A |
| Jane Givens | 91% | 4 | Sports | None |
| Judy Jones | 99% | 9 | News | None |
| Bill Powers | 85% | 1 | News | None |
| Jane Smith | 95% | 8 | Sports | None |
| Jason Williams | 90% | 4 | News | None |

*Fig. 5A*

Lookup Table 520

| Employee Identifier (524) | Employee Type (528) | Protocol Identifier (532) |
|---|---|---|
| 11111 | 1 | 1 |
| 22222 | 1 | 1 |
| 33333 | 2 | 2 |
| 44444 | 3 | 3 |
| 55555 | 1 | 1 |
| 66666 | 4 | 0 |
| ⋮ | ⋮ | ⋮ |

*Fig. 5B*

Compliance Report 640

| Employee Name (700) | Time (704) | Date (708) | Location (712) | Full Cycle (716) |
|---|---|---|---|---|
| Janet Smith | 8:00 a.m. | 5/21/2006 | A | Y |
| Bill Powers | 9:00 a.m. | 5/21/2006 | A | N |
| Bill Forbes | 10:00 a.m. | 5/21/2006 | C | N |
| Jason Williams | 10:07 a.m. | 5/21/2006 | A | Y |
| Jane Givens | 10:30 a.m. | 5/21/2006 | D | N |
| Judy Jones | 11:10 a.m. | 5/21/2006 | A | Y |
| Sandra Collins | 11:20 a.m. | 5/21/2006 | A | Y |

*Fig. 7*

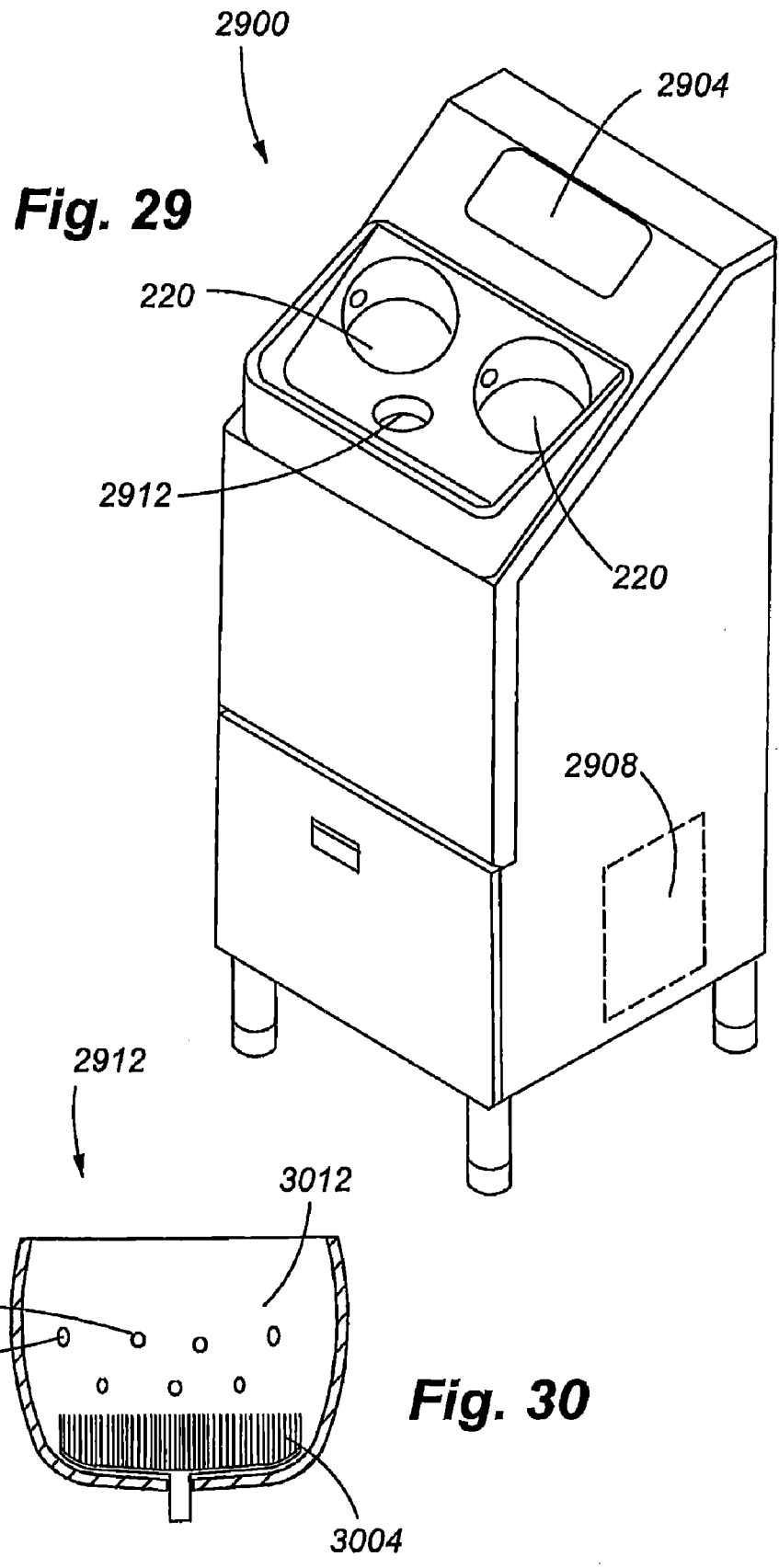

| | Hygiene Requirements | Response to Hygiene Radius Violation | Time to Hygiene Protocol Violation | Contingent Zone Contamination Allowed? | Time To Zone Contamination | Response to Zone Contaminant |
|---|---|---|---|---|---|---|
| Level 1 | None | N/A | N/A | N/A | N/A | N/A |
| Level 2 | BBBB | Alarm | 1 Min | Yes | ∞ | N/A |
| Level 3 | DDDD | Alarm | 30 Sec | Yes | 1 Min | Alarm |
| Level 4 | FFFF | Alarm | 0 Sec | No | 0 Sec | Alarm Lockout |
| | | | | | | |
| | | | | | | |
| | | | | | | |
| | | | | | | |

*Fig. 37*

| | Protocol Identifier 3804 | Hygiene Requirements 3704 | Response to Hygiene Radius Violation 3708 | Time to Hygiene Protocol Violation 3742 | Contingent Zone Contamination Allowed? 3716 | Time To Zone Contamination 3720 | Response to Zone Contaminant 3724 |
|---|---|---|---|---|---|---|---|
| Level 1 — 3808a | 1 | None | N/A | N/A | N/A | N/A | N/A |
| Level 1 — 3808b | 2 | None | N/A | N/A | N/A | N/A | N/A |
| Level 2 — 3812a | 1 | AAAA | Provide Instruction | N/A | Yes | ∞ | N/A |
| Level 2 — 3812b | 2 | BBBB | Alarm | 1 Min | Yes | ∞ | N/A |
| Level 3 — 3816a | 1 | CCCC | Provide Instruction Alarm | 30 Sec | Yes | 1 Min | Alarm |
| Level 3 — 3816b | 2 | DDDD | Alarm Lockout | 30 Sec | Yes | 1 Min | Alarm |
| Level 4 — 3820a | 1 | EEEE | Alarm | 0 Sec | No | 0 Sec | Alarm Lockout |
| Level 4 — 3820b | 2 | FFFF | Alarm | 0 Sec | No | 0 Sec | Alarm Lockout |

| Transition Type 3902 | Employee ID 3904 | Time 3908 | Date 3912 | Hygiene Radius During Transition 3916 | Hygiene Radius Violation? 3920 | Time To HR. Violation Remediation 3924 | Protocal Violation? 3928 | Zone Contamination? 3932 |
|---|---|---|---|---|---|---|---|---|
| 3→4 | 1111 | 9:20 AM | 8/17/08 | 3 | Yes | 20 Sec | No | No |
| 2→4 | 4444 | 10:29 AM | 8/17/08 | 4 | No | N/A | No | No |
| 2→4 | 5555 | 10:29 AM | 8/17/08 | 2 | Yes | 20 Sec | No | No |
| 2→3 | 7777 | 11:50 AM | 8/17/08 | 4 | No | N/A | No | No |
| 2→3 | 8888 | 12:10 PM | 8/17/08 | 2 | Yes | 6 Min | Yes | No |
| 3→4 | 9999 | 3:30 PM | 8/17/08 | 3 | Yes | 20 Sec | No | No |
| 3→4 | 1010 | 3:35 PM | 8/17/08 | 3 | Yes | 5 Min | Yes | Yes |

Fig. 39

| Transition Type | Employee ID | Time | Date | Hygiene Radius During Transition 3916 | Hygiene Radius Downgrade? 4004 | Time to H.R Downgrade 4008 |
|---|---|---|---|---|---|---|
| 3→2 | 2222 | 9:21 AM | 8/17/08 | 3 | No | N/A |
| 3→2 | 3333 | 9:22 AM | 8/17/08 | 3 | Yes | 1 Min |
| 4→2 | 4444 | 10:24 AM | 8/17/08 | 4 | No | N/A |
| 4→2 | 5555 | 10:26 AM | 8/17/08 | 4 | Yes | 1 Min |
| 4→3 | 6666 | 11:40 AM | 8/17/08 | 4 | Yes | 3 Min |
| 4→2 | 7777 | 11:50 AM | 8/17/08 | 4 | No | N/A |
| 4→2 | 8888 | 12:00 PM | 8/17/08 | 3 | Yes | 0 Min |
| 4→1 | 9999 | 3:30 PM | 8/17/08 | 3 | Yes | 1 Min |
| 4→1 | 1010 | 3:50 PM | 8/17/08 | 3 | Yes | 1 Min |

Fig. 40

| Hygiene Radius Violation | Employee ID | Cause | Time | Date | Time to Remediation | Protocol Violation |
|---|---|---|---|---|---|---|
| # 1 | 1111 | Boundary Transition | 9:20 AM | 8/17/08 | 20 Sec | No |
| # 2 | 5555 | Boundary Transition | 10:24 AM | 8/17/08 | 20 Sec | No |
| # 3 | 8888 | Boundary Transition | 12:10 PM | 8/17/08 | 6 Min | Yes |
| # 4 | 9999 | Boundary Transition | 3:30 PM | 8/17/08 | 20 Sec | No |
| # 5 | 1010 | Boundary Transition | 3:35 PM | 8/17/08 | 5 Min | Yes |
| # 6 | 1212 | Zone Contamination | 3:37 PM | 8/17/08 | 20 Sec | No |
| | | | | | | |
| | | | | | | |

*Fig. 41*

| Requirement | Frequency | Hygiene Station Component |
|---|---|---|
| Hand Wash | X Times / Day | Wash Chamber Or Hand Sanitizer |
| Lotion Use | After Every Sanitizer Use | Lotion Dispenser |
| Complete Hand Wash | After Every Y Use Of The Lotion Dispenser | Wash Chamber Only |

| | Employee Id 4404 | Use Type/ End Of Day 4408 | Date 4412 | Time 4416 | Compliance With Daily Requirement 4420 | Compliance With Lotion Use Requirement 4424 | Complete With Hand Wash Requirement 4428 |
|---|---|---|---|---|---|---|---|
| 4432a | 1 | Chamber | 8/17/08 | 9:00 AM | — | — | — |
| 4432b | 1 | Chamber | 8/17/08 | 12:00 PM | — | — | — |
| 4432c | 1 | Chamber | 8/17/08 | 2:00 PM | — | — | — |
| 4432d | 1 | End of Day | 8/17/08 | 5:00 PM | No | — | — |
| 4432e | 1 | Chamber | 8/18/08 | 9:00 AM | — | — | — |
| 4432f | 1 | Sanitizer | 8/18/08 | 10:00 AM | — | Yes | — |
| 4432g | 1 | Lotion | 8/18/08 | 10:01 AM | — | Yes | — |
| 4432h | 1 | Sanitizer | 8/18/08 | 2:00 PM | — | No | — |
| 4432i | 1 | Chamber | 8/18/08 | 4:00 PM | — | — | — |
| 4432j | 1 | End of Day | 8/18/08 | 5:00 PM | Yes | Yes | — |
| 4432k | 1 | Sanitizer | 8/19/08 | 9:00 AM | — | Yes | — |
| 4432l | 1 | Sanitizer | 8/19/08 | 9:01 AM | — | Yes | — |
| 4432m | 1 | Sanitizer | 8/19/08 | 11:00 AM | — | Yes | No |
| 4432n | 1 | Lotion | 8/19/08 | 11:01 AM | — | Yes | No |
| 4432o | 1 | Sanitizer | 8/19/08 | 1:00 PM | — | Yes | No |
| 4432p | 1 | Lotion | 8/19/08 | 1:01 PM | — | Yes | No |
| 4432q | 1 | Sanitizer | 8/19/08 | 3:00 PM | — | Yes | No |
| 4432r | 1 | Lotion | 8/19/08 | 3:01 PM | — | Yes | No |
| 4432s | 1 | End of Day | 8/19/08 | 5:00 PM | Yes | Yes | No |

4400

Data Management Module Report
⤹ 4900

| Enterprise ID # | Station ID # | User ID # | Date | Time | Facility | Wash Cycle Complete | Compliance Monitor ID # |
|---|---|---|---|---|---|---|---|
| 123456 | 111 | 11111 | 7/5/2007 | 8:00 AM | A | Y | Fed #1 |
| 123456 | 112 | 22222 | 7/8/2007 | 9:15 AM | C | Y | Fed #2 |
| 123456 | 113 | 33333 | 7/13/2007 | 8:45 AM | B | Y | State #1 |
| 123456 | 114 | 44444 | 7/16/2007 | 7:30 AM | C | N | Local #1 |
| 123456 | 115 | 55555 | 7/16/2007 | 1:20 PM | D | Y | Local #2 |

*Fig. 49*

| Geographic Location Information 5100 | Compliance Monitor Designation 5102 | Compliance Data Required 5104 | Required Reporting Frequency 5108 | Report Requirements 5112 |
|---|---|---|---|---|
| 1111 | A | Number Washes/Unit, Percent Compliant | Monthly | GGGG |
| 1111 | B | Number Washes/Employee, Percent Compliant | Weekly | HHHH |
| ... | | ... | | |

*Fig. 51*

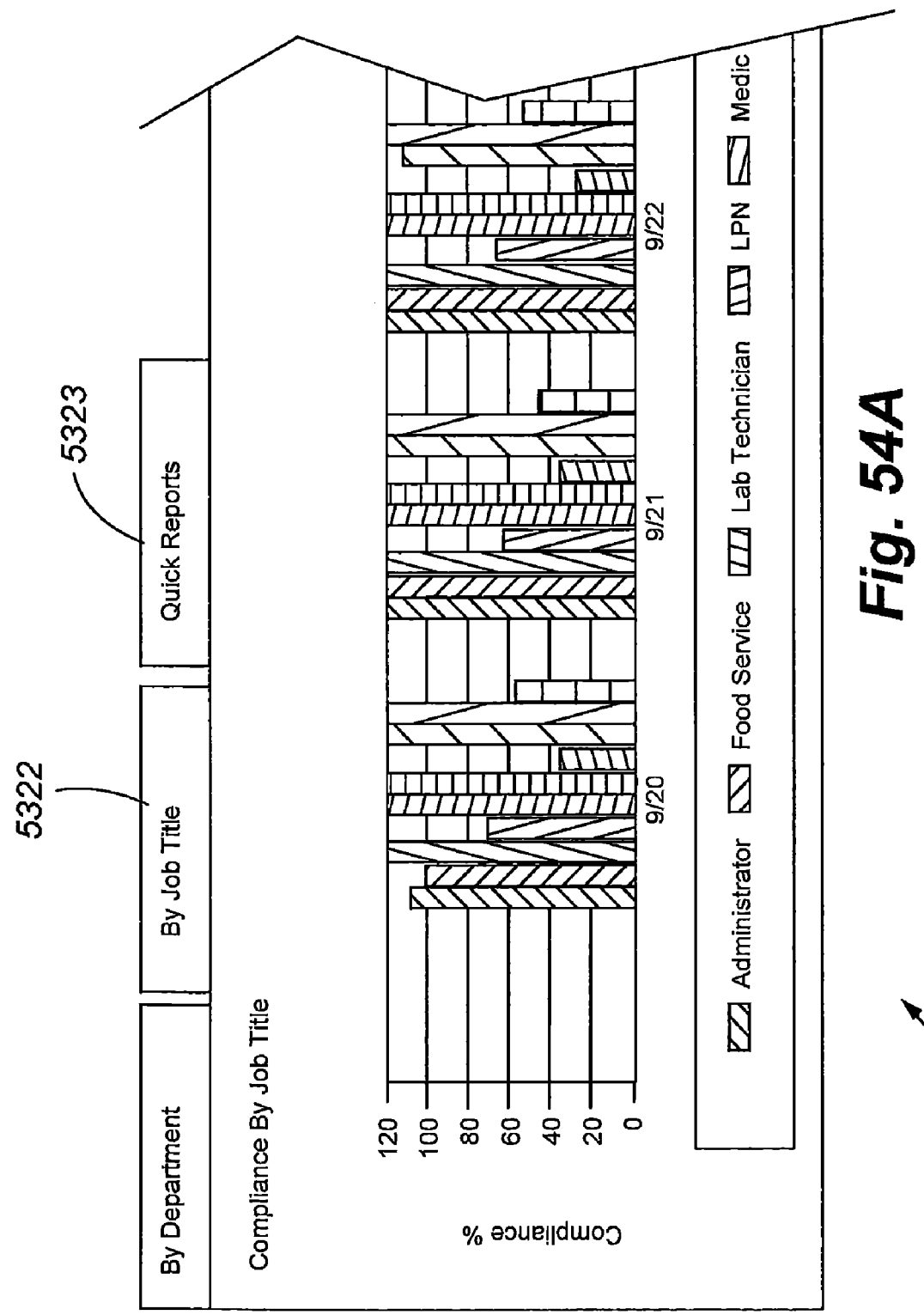

5324

Daily Departmental Compliance

| Department | Target | Washes | Compliance % |
|---|---|---|---|
| Anesthesiology1 | 25 | 26 | 104% |
| Cardiology | 25 | 19 | 76% |
| Emergency Room | 25 | 35 | 140% |
| Geriatrics | 25 | 13 | 52% |
| ICU | 25 | 26 | 104% |
| Neurology | 25 | 20 | 80% |
| NICU | 25 | 24 | 96% |
| Nutricional Services | 25 | 35 | 140% |
| Obstetrics | 50 | 23 | 46% |
| Oncology | 25 | 22 | 88% |
| Operating Room | 25 | 20 | 80% |
| Orthopedics | 25 | 26 | 104% |

/ Greater than 90% of Target

\ Greater than or equal to 75% of Target

/ Less than 75% of Target

*Fig. 55*

WASH CHAMBER FOR SURGICAL ENVIRONMENT

RELATED APPLICATIONS

The present application claims the benefit of U.S. Provisional Application Ser. No. 61/048,924, filed Apr. 29, 2008, entitled "HYGIENE COMPLIANCE FOR FOOD SERVICE ENVIRONMENT", U.S. Provisional Application Ser. No. 61/097,715, filed Sep. 17, 2008, entitled "COMPLETE HAND CARE", U.S. Provisional Application Ser. No. 61/097,723, filed Sep. 17, 2008, entitled "INGRESS/EGRESS SYSTEM FOR HYGIENE COMPLIANCE", U.S. Provisional Application Ser. No. 61/097,736, filed Sep. 17, 2008, entitled "HYGIENE COMPLIANCE", U.S. Provisional Application Ser. No. 61/097,704, filed Sep. 17, 2008, entitled "HYGIENE COMPLIANCE MONITORING", U.S. Provisional Application Ser. No. 61/058,521, filed Jun. 3, 2008, entitled "HYGIENE COMPLIANCE SYSTEM", and U.S. Provisional Application Ser. No. 61/112,120, filed Nov. 6, 2008, entitled "HYGIENE COMPLIANCE SYSTEM", which are incorporated herein by this reference in their entirety.

FIELD OF THE INVENTION

The present invention relates to automated washing systems, and more particularly, to automated washing systems comprising a way of monitoring and/or verifying user participation. Methods of providing compliance verification are also provided.

BACKGROUND

The importance of cleanliness has long been recognized, particularly in the fields of heath-care, food preparation, and laboratories, to name but a few. The practice of surgical scrubbing by surgeons and other operating room personnel is probably the epitome of efforts to cleanse the hands and forearms of persons working in sterile environments. Although manual hand-washing can appear to be effective, medical experts have concluded that automated hand-washing increases hand-washing compliance and reduces the risk of infection.

Touchless automated hand-washing devices are designed to wash the hands of the user and provide the proper amount of antimicrobial solution in a set time. Additionally, these systems diminish the deterrent effects of friction and irritation associated with frequent manual hand-washing. Notwithstanding the benefits and convenience of automated washing devices, difficulties still exist with verifying employee or staff use of the washing apparatus. Moreover, existing systems lack the ability to provide a complete washing. It would be advantageous to have a system that provides automated washing that may be operable to verify usage by the intended users. Accordingly, the present invention is directed to a system and method for providing automated washing, which may be operable to monitor compliance with one or more hygiene requirements.

In addition to the forgoing, problems also exist with spread of bacteria or other contagions throughout a facility based on the movement of persons within the facility. Accordingly, it would be desirable to have a system and/or method for tracking and enforcing hygiene requirements that accounts for movement of individuals associated with a facility. Moreover, it would be desirable to have a system and/or method for monitoring a plurality of hygiene protocols that are associated with a plurality of different locations or network enterprises.

In designing an automated cleaning system a number of features should be considered. For example, the automated cleaning system should be capable of verifying user compliance with a hygiene protocol and also capable of tracking the movements of persons associated with a facility having hygiene requirements. Moreover, the verification system should be operable for a plurality of washing stations associated with a plurality of enterprise networks. Further, the verification system should include a computer readable medium having a set of processor accessible data structures for identifying a hygiene compliance, recording and storing compliance data, and reporting and producing a data management report (including the data collected in one or more of the enterprise networks). The verification system should also include an electronic hygiene compliance verification data signal capable of being stored on a computer readable medium and including source and destination addresses, hygiene compliance information (including data regarding a movement of a person and hygiene related actions taken by the person as a consequence of the movement), an enterprise identifier, and a compliance monitor identifier.

When designing an automated cleaning system, a method to report hygiene compliance should also be provided. The method for reporting hygiene compliance should include determining a geographic location associated with a compliance monitor, determining a monitored entity identifier associated with the geographic location information, determining hygiene compliance data, providing hygiene compliance data associated with the monitored entity identifier (including data regarding a movement of a person and hygiene related actions taken by the person as a consequence of the movement), determining report requirements, and forwarding the provided hygiene compliance data to the compliance monitor.

SUMMARY

In accordance with embodiments of the present invention, a Radio Frequency Identification ("RFID") system is disclosed for use in connection with an automated hand-washing station. However, as described herein, other identifying technologies are appropriate, and such technologies are encompassed by the scope of the present invention. An example of such an alternate identifying technology is Zigbee, which is a specification for a suite of communication protocols using small, low power digital radios based on the IEEE 802.15.4-2006 standard for Wireless Personal Area Networks (WPANs). It is to be understood therefore, that RFID is used as an example and is not intended to limit the scope of the present invention.

The system is operable to record and report on user compliance with hand-washing requirements. To ensure user safety and product performance, the system has the capability to ensure that only authorized consumable solutions are used in the cleaning station. The RFID data capture capability, in conjunction with a video system, allows users to have real time feedback of their personal compliance as well as individual user focused information conveyed at the time of utilizing the cleaning station.

In accordance with one or more embodiments described herein, the user carries a RFID tag that is programmed with information specific to the individual. Upon approaching the cleaning station, a RFID reader recognizes the user's tag and records the user name, time, date, station location, and whether the cleaning event was a complete cycle. The data is stored in the readers' database until captured via various methods and transferred into a report format for the administrator. The administrator can then review the compliance statistics for the various users.

In accordance with embodiments of the invention, a washing system is provided. The washing system includes:
(a) a rotatable wash cylinder to receive an appendage of a user; and
(b) a plurality of nozzles in the rotatable wash cylinder, the plurality of nozzles to direct a cleaning fluid inwardly into an interior of the wash cylinder, wherein the depth of the wash cylinder is adjustable, whereby, in a first mode of operation, the wash cylinder has a first depth and, in a second mode of operation, the wash cylinder has a second depth, with the first depth being greater than the second depth to accommodate user appendages of differing sizes.

In accordance with embodiments of the present invention, a method is provided that includes the steps:
(a) receiving a first identifier of a first user;
(b) in response to receipt of the first identifier, positioning a wash cylinder of an adjustable depth to a first depth to accommodate a first appendage of the first user;
(c) performing a wash of the first appendage;
(d) thereafter receiving a second identifier of a second user;
(e) in response to receipt of the second identifier, positioning the wash cylinder to a second depth to accommodate a second appendage of the second user;
(f) performing a wash of the second appendage, wherein the first and second appendages have differing sizes.

In accordance with embodiments of the present invention, a method is provided that includes the steps:
(a) positioning, by at least one of a processor and a manual control, a wash cylinder to a first depth;
(b) receiving a first appendage of a first user;
(c) washing the first appendage;
(d) positioning, by the at least one of a processor and a manual control, a wash cylinder to a second depth;
(e) receiving a second appendage of a second user;
(f) washing the second appendage.

In accordance with embodiments of the present invention are directed to a system and method of monitoring compliance with a hygiene protocol. The movement of person within or otherwise associated with a facility may be tracked and hygiene requirements may be imposed based on the movement. In monitoring hygiene compliance, a number of hygiene levels may be defined that are associated with difference hygiene requirements. A hygiene level may be associated with an individual and that level may be raised or lowered based on hygiene related activity associated with the individual. An individual's hygiene level and/or his compliance with multi-level hygiene requirements may be tracked through the use of monitored hygiene stations and/or location tracking stations. These and other compliance requirements may be tracked or monitored from a remote monitoring center, or compliance data hub. The compliance data hub may be operable to monitor a plurality of hygiene protocols that are defined for a plurality of different facilities or enterprise networks.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the invention is considered to include a tangible storage medium or distribution medium and prior art-recognized equivalents and successor media, in which the software implementations of the present invention are stored.

The terms "determine", "calculate" and "compute," and variations thereof, as used herein, are used interchangeably and include any type of methodology, process, mathematical operation or technique.

The term "module" as used herein refers to any known or later developed hardware, software, firmware, artificial intelligence, fuzzy logic, or combination of hardware and software that is capable of performing the functionality associated with that element. Also, while the invention is described in terms of exemplary embodiments, it should be appreciated that individual aspects of the invention can be separately claimed.

Various embodiments of the present invention are set forth in the attached figures and in the detailed description of the invention as provided herein and as embodied by the claims. It should be understood, however, that this Summary does not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 4 is an exemplary station-use record in accordance with embodiments of the present invention;

FIG. 5A is an exemplary employee record in accordance with embodiments of the present invention;

FIG. 5B shows a set of data structures according to an embodiment of the present invention;

FIG. 7 is an exemplary compliance report in accordance with embodiments of the present invention;

FIGS. 124A-12E are additional schematic illustrations of the system shown in FIG. 9;

FIG. 29 shows an adjustable cycle cleaning station in accordance with embodiments of the present invention;

FIG. 30 shows a debris removal cylinder in accordance with embodiments of the present invention;

FIG. 37 is an exemplary multilevel hygiene protocol in accordance with embodiments of the present invention;

FIG. 38 is another multilevel hygiene protocol in accordance with alternative embodiments of the present invention;

FIG. 39 is a compliance report in accordance with embodiments of the present invention;

FIG. 40 is another compliance report in accordance with embodiments of the present invention;

FIG. 41 is still another compliance report in accordance with embodiments of the present invention;

FIG. 43 is still another hygiene protocol in accordance with embodiments of the present invention;

FIG. 44 is still another compliance report in accordance with embodiments of the present invention;

FIG. 49 is an exemplary data management module report;

FIG. 51 shows a set of data structures according to an embodiment of the present invention;

FIGS. 54A-54B is a screenshot according to an embodiment;

FIG. 55 is a screenshot according to an embodiment;

Figure 1:
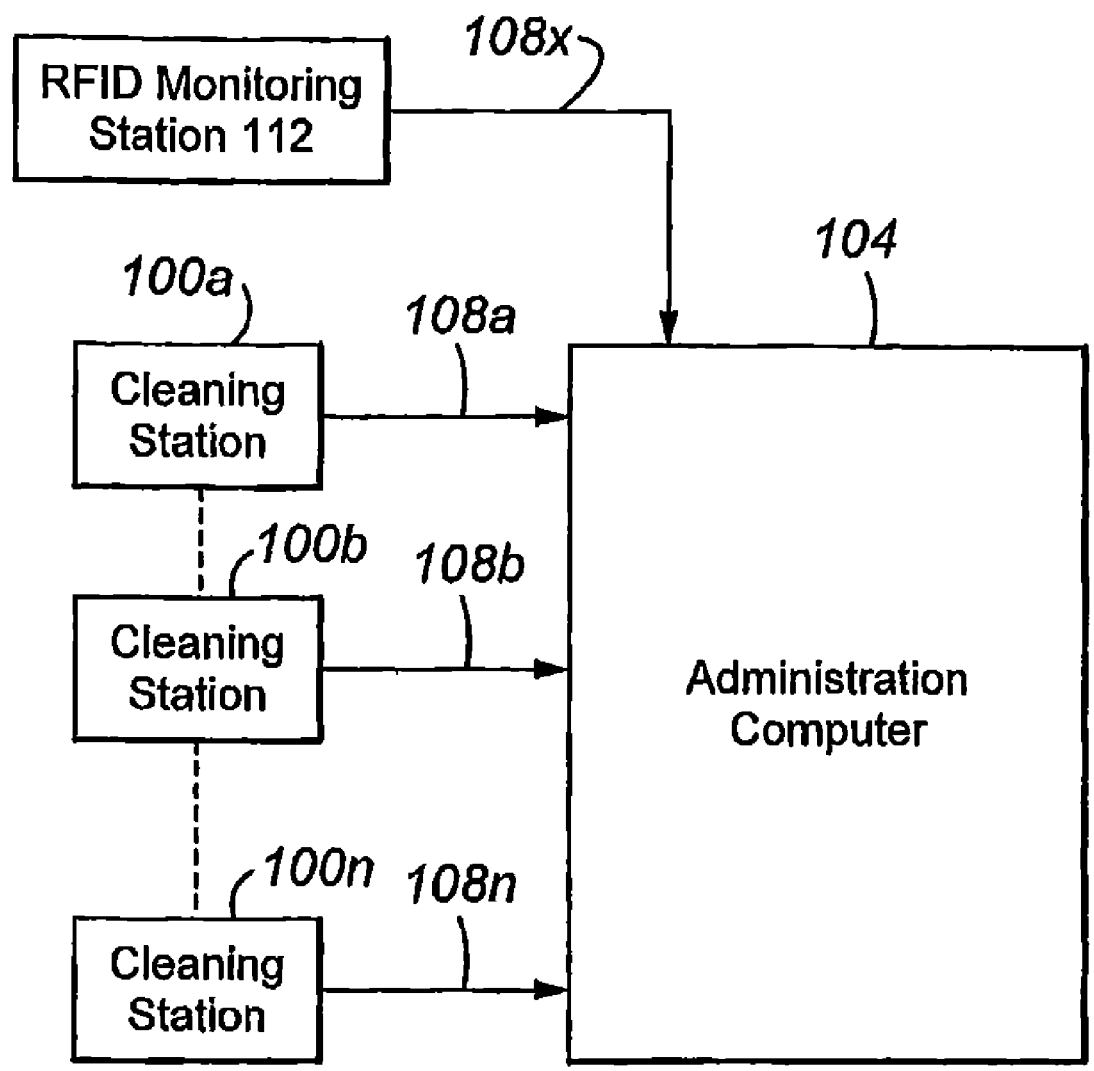
FIG. 1 is a block diagram of components that may be included in embodiments of the present invention.

The drawings are not necessarily to scale.

DETAILED DESCRIPTION

The exemplary systems and methods of this invention will be described in relation to distributed processing networks. However, to avoid unnecessarily obscuring the present invention, the following description omits a number of known structures and devices. This omission is not to be construed as a limitation of the scope of the claimed invention. Specific details are set forth to provide an understanding of the present invention. It should, however, be appreciated that the present invention may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a washing station, or collocated on a particular node of a distributed network, such as an analog and/or digital telecommunications network, a packet-switched network, or a circuit-switched network. It will be appreciated from the following description, and for reasons of computational efficiency, that the components of the system can be arranged at any location within a distributed network of components without affecting the operation of the system. For example, the various components can be located in a switch, media server, gateway, in one or more washing stations, at one or more users' premises, or some combination thereof.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the invention.

The present invention is directed to a system and method for ensuring employee compliance with washing requirements, such as hand-washing requirements. However, it is to be understood that embodiments of the present application are also applicable to other types of washing systems, including for example, boot-washing systems. In accordance with embodiments of the present invention, employee use of one or more automated cleaning stations is monitored. The cleaning stations operate to dispense one or more fluids, such as water, a cleaning fluid, such as soap, and/or a disinfectant, etc., while a person's hands are placed in a washbasin. As used herein, a "washbasin" means a structure associated with the cleaning station where the hands (or boots) are cleaned, such as one or more wash cylinders, spray areas, pans, tubs, etc. Employees may be instructed to wash their hands for a minimum amount of time that has been determined to be sufficient to provide a complete cleaning. The minimum time needed to provide a complete cleaning and/or the types of fluids, agents, and/or cleaning methods used in the automated cleaning may vary depending a variety of factors including the employee's job duties and/or his or her past noncompliance. The cleaning stations are operable to record and report data related to employee compliance with such requirements. At least some employees may not be required to wash their hands.

For purposes of discussion, the various embodiments of the present invention are discussed herein in connection cleaning an appendage of a user. However, it should be understood that the various embodiments may be used in connection with other objects. As used herein an "object" may refer to anything cleaned by the automated cleaning station. An object may be, for example, an appendage of a user, a tool, a boot, and/or an inanimate object, etc. As used herein, "inanimate object" means an object that is principally not a biological tissue, although biological matter may be associated with the inanimate object, for example, a virus, bacteria, and/or pieces of tissue on a tool.

Referring now to FIG. 1, components of a compliance system in accordance with embodiments of the present invention are illustrated in block diagram form. Shown in FIG. 1 is a plurality of cleaning stations 100a, 100b . . . 100n. The cleaning stations 100a-100n may be used by people employed at a facility that requires employees to wash their hands. Such facilities may include, for example, restaurants, food processing facilities, hospitals and laboratories. Also shown in FIG. 1 is an administration computer 104 for use by a manager or administrator of the facility. The administration computer 104 is operable to generate a compliance report as described herein. As used herein, an administration computer 104 may include a file server or other network computer operable to serve as a data collection point for data associated with cleaning stations 100a . . . 100n. Additionally, it should be understood that separate computational devices may be used to store data and to access the stored data.

The administration computer 104 communicates with the cleaning stations 100a-100n over a plurality of communication links 108a, 108b . . . 108n. The communication links may be implemented by any one of a variety of methods and may depend on the type of facility in which the cleaning stations 100a-100n are used. In particular, the communication links 108a-108n may be implemented as part of a local area network (LAN) or a wide area network (WAN). As used herein, a "communication link" does not imply a direct connection between two endpoints. As can be appreciated by one of skill in the art, a "communication link" may include a communication session having parts that are routed through various nodes of a communication network. More particularly, the communication links 108a-108n may be implemented using such protocols as Ethernet or USB. The communications links 108a-108n may be implemented as wired or wireless connections. It may be the case that the administration computer 104 is located in a separate facility from one or more of the cleaning stations 100a-100n. In this case, a distributed data network such as the Internet may form part of the communication links 108a-108n.

In accordance with embodiments of the present invention, the system 100 may include active RFID monitoring antennas or stations 112. The RFID monitoring stations are operable to read RFID tags, which may be worn by the employees of the facility. The RFID monitoring stations are additionally in communication with the administration computer 104 over communication link 108x.

Figure 2:
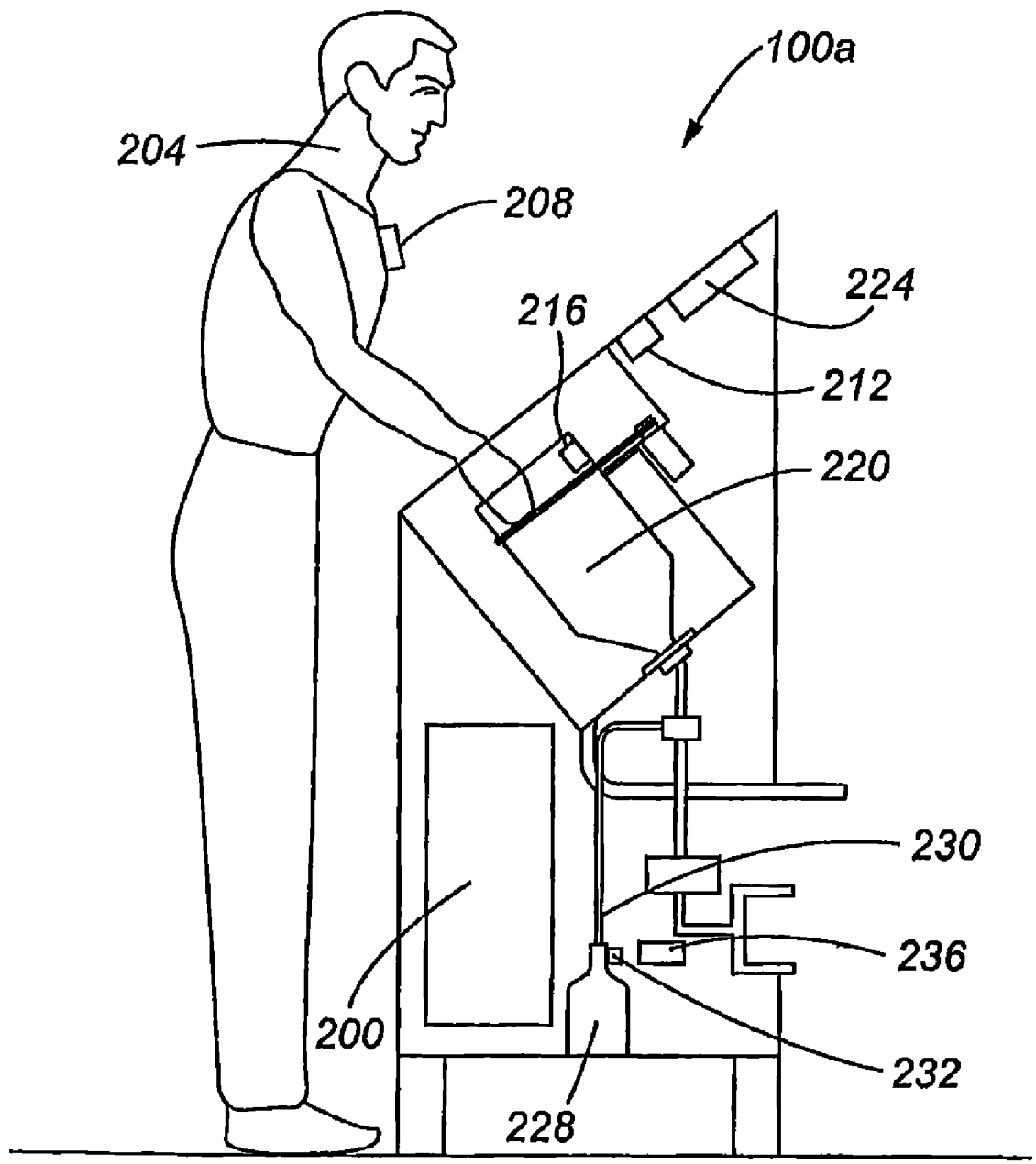
FIG. 2 is a schematic depiction of a cleaning station in accordance with embodiments of the present invention.

Referring now to FIG. 2, an exemplary cleaning station 100a is illustrated. The cleaning station 100a includes a cleaning station operations monitor 200. The cleaning station operations monitor 200 may comprise a computational device such as a general-purpose computer, controller, or ASIC that controls and coordinates the operation of the various electronic components associated with the cleaning station 100a. Additionally, the cleaning station operations monitor 200 is operable to record data associated with employee use of the cleaning station 100a and to report the data to the administration computer 104. The cleaning station operations monitor 200 may be incorporated into the cleaning station 100a or, alternatively, may be implemented as a separate computing device.

Also shown in FIG. 2 is a user 204 of the cleaning station 100a. The user 204 may be an employee or visitor who is required to wash their hands because of the nature of their work or the nature of the facility. The user 204 is shown wearing a user RFID tag 208. The user RFID tag 208 is programmed by an RFID tag programming device (not shown) with information such as an employee number that, when read, uniquely identifies the employee or user 204. The RFID tag 208 may be incorporated into an identification badge or bracelet worn by the user 204.

In accordance with embodiments of the present invention, the cleaning station 100a includes an RFID reader 212 and an optical sensor 216. The RFID reader 212 is positioned so as to be able to read the user RFID tag 208 when the user 204 is washing his or her hands at the cleaning station 100a. The RFID reader 212 may be incorporated into the cleaning station 100a or, alternatively, may be implemented as a stand-alone device. For example, the RFID reader 212 may be positioned adjacent to a cabinet associated with the cleaning station 100a. The optical sensor 216 is positioned so as to be able to sense that the hands of the user 204 are placed within the washbasin 220 in a position where they will properly receive cleaning fluids, such as water, soap and/or disinfectant as dispensed by the cleaning station 100a. The RFID reader 212 and the optical sensor 216 are in communication with cleaning station operations monitor 200, which, in turn, is operable to collect data associated with these devices. In particular, data is collected from the RFID reader 212 indicating the identity of the user 204. Additionally, the cleaning station operations monitor 200 records the length of time in which the hands of the user 204 were placed in the washbasin 220 as indicated by the optical sensor 216. In addition to RFID, other methods of identifying a user are within the scope of the present invention. In particular, a user may be identified by means of a typed password, retinal scan, voice print, palm print, fingerprint, face identification, bar coding (on an employee ID), etc.

The cleaning station 100a also includes a video display 224 positioned for viewing by the user 204 when he or she is washing his or her hands. The video display 224 may be incorporated in the cleaning station 100a or, alternatively, may be implemented as a separate device. For example, the video display 224 may be positioned on a wall in front of the user 204 as they stand at the cleaning station 100a. The video display 224 operates to display brief video segments to the user 204 while the cleaning station 100a is cleaning his or her hands. The video display 224 may be under the control of the cleaning station operations monitor 200. As the user 204 is utilizing the cleaning station 100a, administrator-selected data is transmitted to the video display 224. This information may be simple feedback to the user 204 informing them of the amount of hand washings they did in the current day, week, month, etc. In addition, there may be training programs that communicate information to the user 204, such as the risks of hand borne pathogens, to constantly remind the user 204 of the importance of hand hygiene. This system has the flexibility to provide a wide range of communications to the user 204.

Also shown in FIG. 2 is a consumables container 228 that contains a material, such as soap or disinfectant used in connection with the operation of the cleaning station 100a. Although not shown, a plurality of consumable containers 228 may be associated with a cleaning station 100a. The consumables container 228 includes a detachable connection to a consumable receptacle 230 associated with the cleaning station 100a so that the consumable container 228 may be removed and disposed of when its contents are expended. After the disposal of a used consumables container 228, a new consumables container 228 is then attached to the cleaning station 100a. In accordance with embodiments of the present invention, the consumables container 228 also includes a consumables RFID tag 232 that contains information related to the consumable container 228. A consumables RFID reader 236 associated with the cleaning station 100a reads the consumables RFID tag 232 and communicates information related to the consumables container 228 to the cleaning station operations monitor 200. Although RFID is discussed herein for use of identification of consumables, other types of identification systems may be used, such as bar codes.

Figure 3:
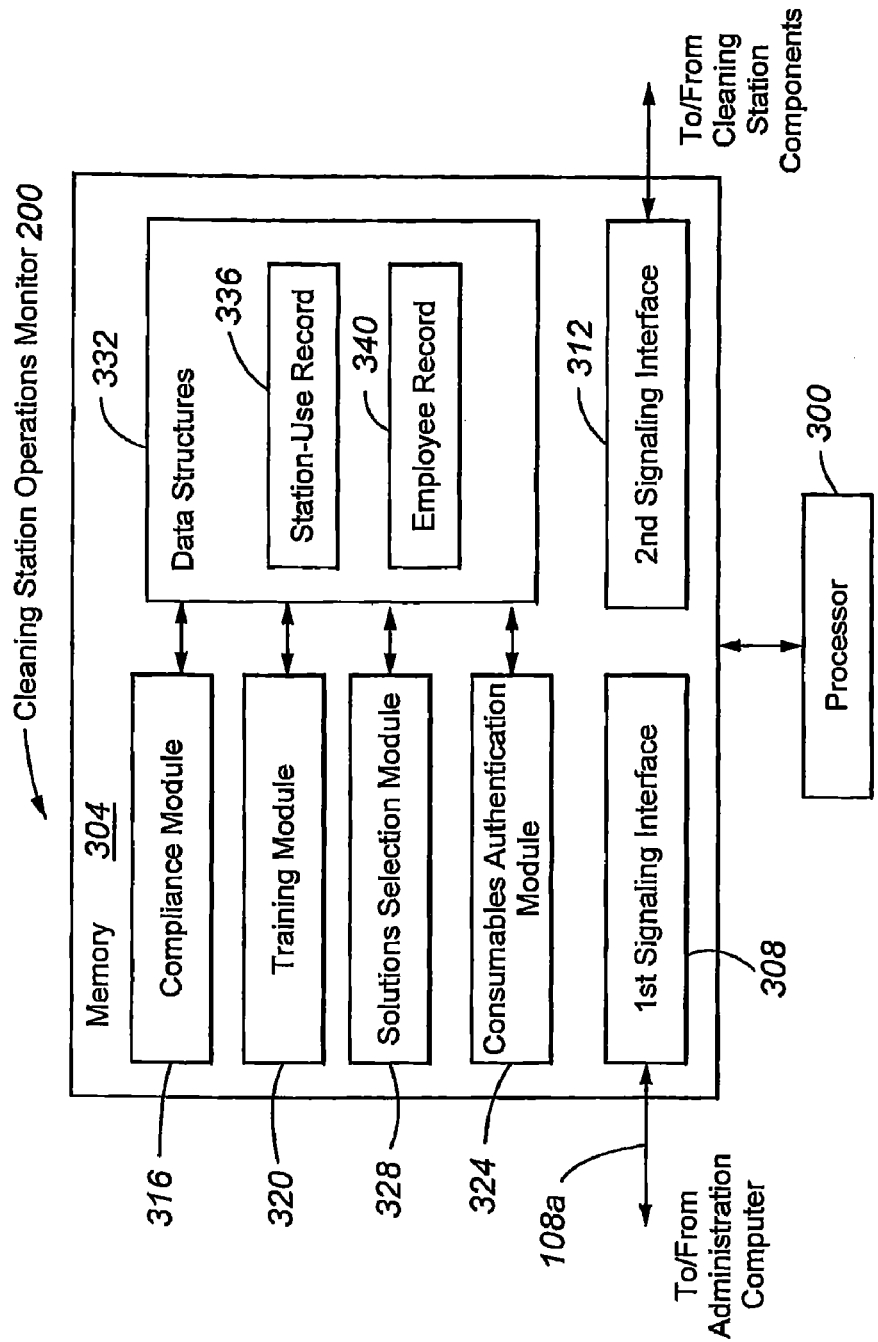
FIG. 3 is a block diagram of a cleaning station operations monitor in accordance with embodiments of the present invention.

Referring now to FIG. 3, a block diagram of components and features of the cleaning station operations monitor 200 is shown. As mentioned previously, the cleaning station monitor 200 is a computational device. Accordingly, the cleaning station operations monitor 200 includes a processor 300, a memory 304 and signaling interfaces 308 and 312 operable to communicate with external electronic and/or computational components. The first signaling interface 308 operates to communicate with the administration computer 104 over communication link 108a, as described above. The second signaling interface 312 operates to communicate with the various electronic components associated with the cleaning station 100a including the RFID readers 212 and 236, the optical sensor 216, and the video display 224. The second signaling interface 312 may be a portion of a backplane incorporated into cleaning station 100a that includes a connection to the cleaning station's 100a electronic components. Alternatively, if the cleaning station operations monitor 200 is implemented as a stand-alone computer, the cleaning station operations monitor 200 may communicate with the cleaning station's electronic components through a network or serial bus connection.

The memory 304 includes a plurality of stored program applications or modules that implement various features of a compliance monitoring system. In accordance with embodiments of the present invention, the memory 304 may include a compliance-monitoring module 316, a training module 320, a consumables authentication module 324, and/or a solutions selection module 328. Additionally, the memory 304 may include data structures 332 associated with the various modules. In accordance with embodiments of the present invention, the data structures 332 include a station-use record 336 and one or more employee records 340. The operation of the various modules and data structures is described in greater detail below.

The compliance-monitoring module 316 operates to monitor and record the activity of a plurality of users 204 of the cleaning station 100a. The process is outlined as follows. The user 204 approaches a cleaning station 100a with a RFID tag 208 on their person, which was programmed with a RFID tag programming device with the individual's name or number, and/or other pertinent data. The tag 208 is read by the RFID reader 212 when the user 204 approaches and/or begins using the cleaning station 100a. When the user 204 places his or her hands into the cleaning station washbasin 220, the optical sensor 216 initiates a cleaning cycle. If the hands of the user 204 do not stay in the washbasin 220 for the full cycle time, the optical sensor 216 will indicate in the data structure 332 that the user 204 did not have a complete cleaning. Once the user is finished using the cleaning station 100a, the data showing such items as user name, time, date, station location and/or identification, and whether the cycle was complete, etc., is stored in the data structure 332. The stored data is later accessed by the administration computer 104 in connection with the generation of a compliance report.

An exemplary station-use record 336 having data associated with a plurality of users 204 is shown in FIG. 4. In accordance with embodiments of the present invention, an entry in the station-use record 336 may include an employee name 400 indicating who used the cleaning station 100a, a time stamp 404 indicating when the cleaning cycle was initiated, a duration 408 indicating how long the user 204 kept his or her hands in the washbasin 220, the date 412, and a compliance indicator 416 specifying whether or not the user 204 kept his or her hands in the washbasin 220 for the required time. As an example, the station-use record shown in FIG. 4 indicates that on May 21, 2006 Janet Smith met the hand-washing requirement by completing a cleaning cycle that was initiated at 8:00.00 A.M. and that lasted for 10 seconds. In an alternative embodiment, the station-use record 336 may contain only raw data such as the time 404, date 412 and duration 408 of the cleaning cycle while determinations related to compliance requirements are made by a separate module running on the administration computer 104.

The compliance-monitoring module 316 may also operate to monitor hand-washing requirements that are specific to each employee. Some employees may have stricter hand washing requirements than others at the same facility. For example, a hospital emergency room may employ both surgeons and social workers. As can be appreciated, the surgeons will be required to wash their hands more frequently and more thoroughly than the social workers. Accordingly, the compliance-monitoring module 316 may access employee records to determine the type, concentration, and/or amount of cleaning fluid to be dispensed for a particular employee. Additionally, employee records may contain other hand washing compliance data that is specific to each employee such as the amount of time and/or frequency that an employee is required to wash his or her hands. Washing requirements may also depend on an employee's history of compliance with his or her washing requirements. For example, an employee may be required to wash his or her hands more thoroughly if his or her previous hand washings were incomplete or hand not been wash for some period of time.

Embodiments of the present invention may include a training module 320. In accordance with at least one embodiment of the present invention, the training module 320 operates to transmit educational information to the user 204 while the cleaning cycle is running via sound and/or a visual source, such as a video display 224. The information may comprise segments equal in duration, or slightly longer or shorter in duration than the cleaning cycle. For example, the segments may contain information regarding hand hygiene in a series of segments lasting approximately 10-15 seconds. In accordance with at least one embodiment of the present invention, the employee record 340 portion of the data structure 332 keeps track of the user 204 and knows the sequence of training segments so each time a user 204 uses the cleaning station 100a, the next pertinent training segment will display on the video display 224.

In accordance with at least one embodiment of the present invention, the training module 320 may access the employee record 340 to provide custom designed content in conjunction with the user's 204 needs/requests. Accordingly, as one possible alternative to educational/training content, entertainment content specific to the user's 204 preferences may be displayed. Here, other information is conveyed to the user, such as news (e.g., weather, breaking stories, current events, stock prices, etc.) and sports information. The training module 320 may, therefore, accommodate specific requests to convey information of interest to the user. In at least one embodiment of the present invention, the information conveyed to the user may be anything other than information about a cleaning station function parameter (e.g., water pressure, soap level, etc.). That is, content other than information about the cleaning station operating parameters so that the user is interested in staying at the cleaning station for an entire wash cycle.

The training module 320 may give feedback to the user 204 through the video display 224, including such information as their hand-washing statistics over a given period of time. For example the administrator of a facility may want to encourage system usage by conveying one or more compliance statistics, and/or informing a user 204 that the user 204 has won a prize by having high marks for compliance with the hand-washing protocol. Accordingly, the employee record 340 may keep track of data associated with user 204, and this data may be accessed by the training module 320 to inform the user 204 in real time, and/or the administrator in a subsequent report, as to compliance statistics. Additionally, the video display 224 may be used to provide notices, such as for upcoming meetings and events that are pertinent to all staff or to a specific person.

The solutions selection module 328 may determine which solution is to be used with each individual user 204. For example, one user 204 may have an allergy to the standard solution, so the system is programmed to automatically use a different and appropriate solution when this user 204 is identified through their RFID tag 208. Information related to user allergies may be contained in the employee record 340.

An exemplary employee record 340 for use in connection with both the training module 320 and the solutions selection module 328 is shown in FIG. 5A. In accordance with embodiments of the present invention, an entry in the employee record 340 may include the employee name 500, hand-washing 504 statistics associated with employee, current training segment 508 to be viewed by the employee, the employee's preferred entertainment content 512, and/or a listing of the employee's allergies 516. As an example, the employee record shown in FIG. 5A indicates that Bill Forbes is in 97% compliance with the hand-washing requirement, has currently viewed seven training modules, prefers to watch the news while washing his hands, and has an allergy to cleaning solution A.

In accordance with embodiments of the present invention, an employee record may include a lookup table that indicates a particular cleaning protocol that is to be applied to a particular employee. An exemplary lookup table 520 is shown in FIG. 5B. The lookup table 520 includes a plurality of employee identifiers 524 and, for each employee identifier, a corresponding employee type indicator 528 and cleaning protocol identifier 532. The employee identifier 524 is commonly an RFID or suitable wirelessly readable identification code. The employee type indicator 528 commonly references the job responsibilities and/or title/position of the identified employee. For example, in a caregiver application a "1" might refer to a nurse, a "2" to an imaging technician, a "3" to a doctor, and a "4" to a member of the janitorial staff. Alternatively or in combination, the particular individuals may be identified by a key code including a name or a job description. The cleaning protocol identifier 532 refers to the particular cleaning protocol to be used for the corresponding identified employee. Typically, each cleaning protocol has a corresponding set of cleaning medium to be used, medium application duration, and wash duration. For example, cleaning protocol identifier "1" may require a ChlorHexidine Gluconate ("CHG") wash, a "2" either a CHG wash or alcohol towelette or wipe, and a "3" a CHG wash followed by an alcohol wipe. Examples of other sanitizing solutions that may be used individually or collectively in cleaning protocol(s) include quaternary ammonium solutions. In one configuration, the cleaning protocol identifier is further varied based upon the location of the corresponding washing station, which is readily determined from the station identifier. A washing station in a highly hygiene sensitive area, such as an operating room, may provide a more demanding cleaning protocol than a station at a less hygiene sensitive area, such as a nursing station. In some cases, the cleaning protocol identifier may indicate that no cleaning is required. For example, the data structures of FIG. 5B show that, for employee type "4", the protocol identifier has a value of "0", or no cleaning is required.

It should be understood that the data fields associated with the exemplary employee record 340 discussed above and shown in FIG. 5A and the lookup table 520 shown in FIG. 5B are by way of illustration and not limitation. A particular employee record 340 may include other fields such as, for example, a user's department, an auto-assigned system identification number, a RFID number, a user identification number, one or more contact telephone numbers, and/or a contact email address. As can be appreciated, the choice of data fields used in a particular employee record 340 will vary depending on the context and the requirements that are particular to each use of the present invention.

In accordance with embodiments of the present invention, the employee record 340 may be an instance of a global employee record maintained centrally at the administration computer 104. Accordingly, the administration computer may periodically access and/or update a plurality of instances of employee records 340 associated with each cleaning station 100*a*-100*n* in order to maintain a comprehensive employee record. Alternatively, at least a portion of the employee use record 340 or data described herein as being associated with the employee use record 340 may be stored in the RFID tag 208 worn by the user 204. For example, a list of the user's 204 allergies may be stored in his or her RFID tag 208 and read by the RFID reader 212 when the user 204 washes his or her hands.

Embodiments of the present invention may include operation of a consumables authentication module 324 that operates to recognize when a non-authorized solution is introduced into the system. The consumables container 228 and/or a receptacle or fitting associated with the cleaning station 100*a* for receiving the consumables container 228 may be mechanically designed to discourage introducing non-authorized solutions to the system. In accordance with embodiments of the present invention, the consumables container 228 includes a consumable container RFID tag 232 that is recognized by the RFID reader 236 as an approved solutions container. If the consumables container 228 is withdrawn from the cleaning station 100*a* and reinstalled, the RFID reader 236 will recognize the tag as invalid and warn the user 204 through the video display 224 and/or the administrator through the administration computer 104 that this is not acceptable and potentially void the product warranty. Alternatively, or in addition thereto, an option is available where the cleaning station 100*a* will stop functioning at the direction of the consumables authentication module 328 until a proper consumables container 228 with a valid RFID tag 232 is inserted into the cleaning station solution receptacle 230. In yet another possible alternative and/or in addition to the options provided above, the known number of doses or applications of the consumable material may be associated with a valid RFID tag 232 and monitored by the consumables authentication module 328 so that once the number of applications is reached (and thus the consumable expended) the cleaning station 100*a* cannot be used until another valid consumables container 228 is installed. For example, say that one consumables container 228 contains enough cleaning fluid for approximately 500 hand-washing cycles. Once the cleaning station 100*a* has administered approximately 500 hand-washing cycles using a particular consumables container 228, then this container will no longer be operable with the cleaning station 100*a*. This prevents the consumable container 228 from being removed, refilled with a non-approved cleaning fluid, and then reattached for use with the cleaning station 100*a*. Such forced compliance for use of the proper consumables provides compliance regulators and/or administrators confidence that, for example, the approved disinfectants are being applied to the users 204 hands with each cleaning or use.

In addition to RFID, other methods and/or systems may be used to identify the consumables container 228. In particular, the consumable container 228 may be identified by a bar code and bar code reader. Moreover, the present invention may include modules that perform other functions such as collecting and reporting maintenance data; reporting information on the last recorded information transfer; and/or reporting the cleaning station's name, type, IP address and current software version.

Figure 6:
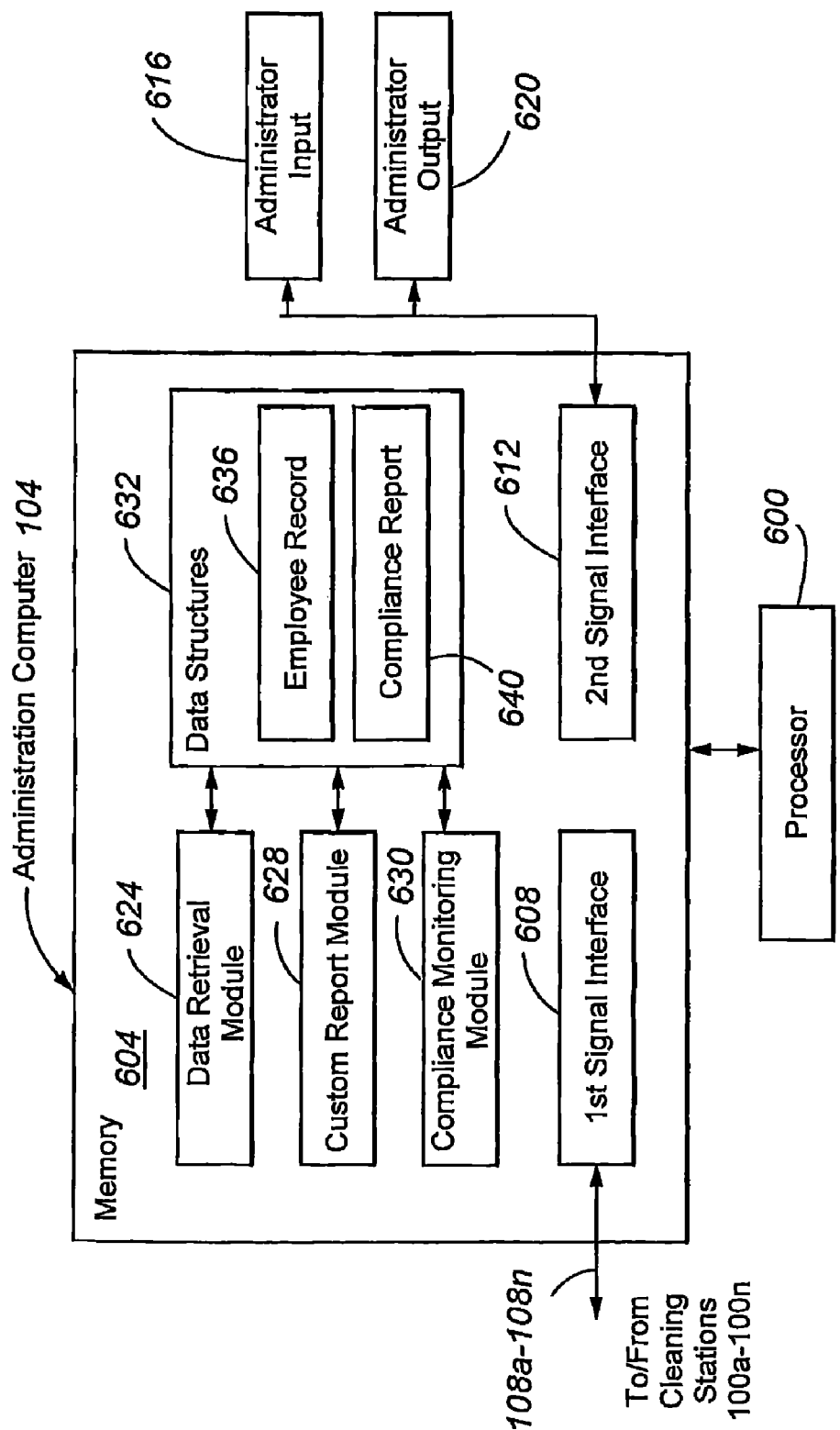
FIG. 6 is a block diagram of an administration computer in accordance with embodiments of the present invention.

Referring now to FIG. 6, a block diagram showing components and features of the administration computer 104 is illustrated. Administration computer 104 includes a processor 600, a memory 604 and signaling interfaces 608 and 612 operable to communicate with external electronic and/or computational components. The first signaling interface 608 operates to communicate with the cleaning stations 100*a*-100*n* over communication links 108*a*-108*n*, as described above. The second signaling interface operates to communicate with the various input 616 and output 620 devices associated with the administration computer 104. The input device 616 may be, for example, a keyboard or a mouse. The output device 620 may be, for example, a monitor or a printer.

The memory 604 includes a plurality of stored program applications or modules that implement various features of a compliance monitoring system. In accordance with embodiments of the present invention, the memory 604 may include a data retrieval module 624, custom report module 628, and a compliance monitoring module 630. Additionally, the memory 604 may include data structures 632 associated with the various modules. In accordance with embodiments of the present invention, the data structures 632 may include an employee record 636 and/or a compliance report 640. As can be appreciated by one of skill in the art from the disclosure herein, the memory 604 may include database structures implemented using suitable database software (such as SQL Server Express).

The data retrieval module 624 operates to retrieve data associated with cleaning stations 100a-100n. Such data may include data related to cleaning station usage and/or employee specific data. The data may be contained in a cleaning station-use record 336 and/or an employee record 340 associated with a cleaning station 100a-100n. Additionally, the data retrieval module 624 may operate to maintain a global employee record 636 as described above.

The custom report module 628 operates to generate the compliance report 640. The compliance report is generated from data contained in each station-use record 336 associated with cleaning stations 100a-100n. An exemplary compliance report is shown in FIG. 7. In accordance with embodiments of the present invention, an entry in the compliance report 640 may include an employee name 700, time stamp 704 indicating when a cleaning cycle was initiated, the date 708 of the cleaning cycle, the location 712 where the cleaning cycle took place, and a compliance indicator 716 specifying whether or not the user 204 met the compliance requirement. As an example, the compliance report shown in FIG. 7 indicates that on May 21, 2006 Janet Smith met the hand-washing requirement by completing a cleaning cycle that was initiated at 8:00.00 A.M. at cleaning station A. As noted, compliance reports may include data pertaining to user statistics. Alternatively, or in addition to reports comprising user statistics, reports may be generated that are directed to the consumables, such as soap and disinfectants.

The compliance report 640 may be generated at different time intervals and may be grouped based on different criteria. For example, the compliance report may be generated daily, weekly, monthly, yearly, et cetera. Moreover, the compliance report 640 may be generated that are grouped by individual or station.

Figure 8:
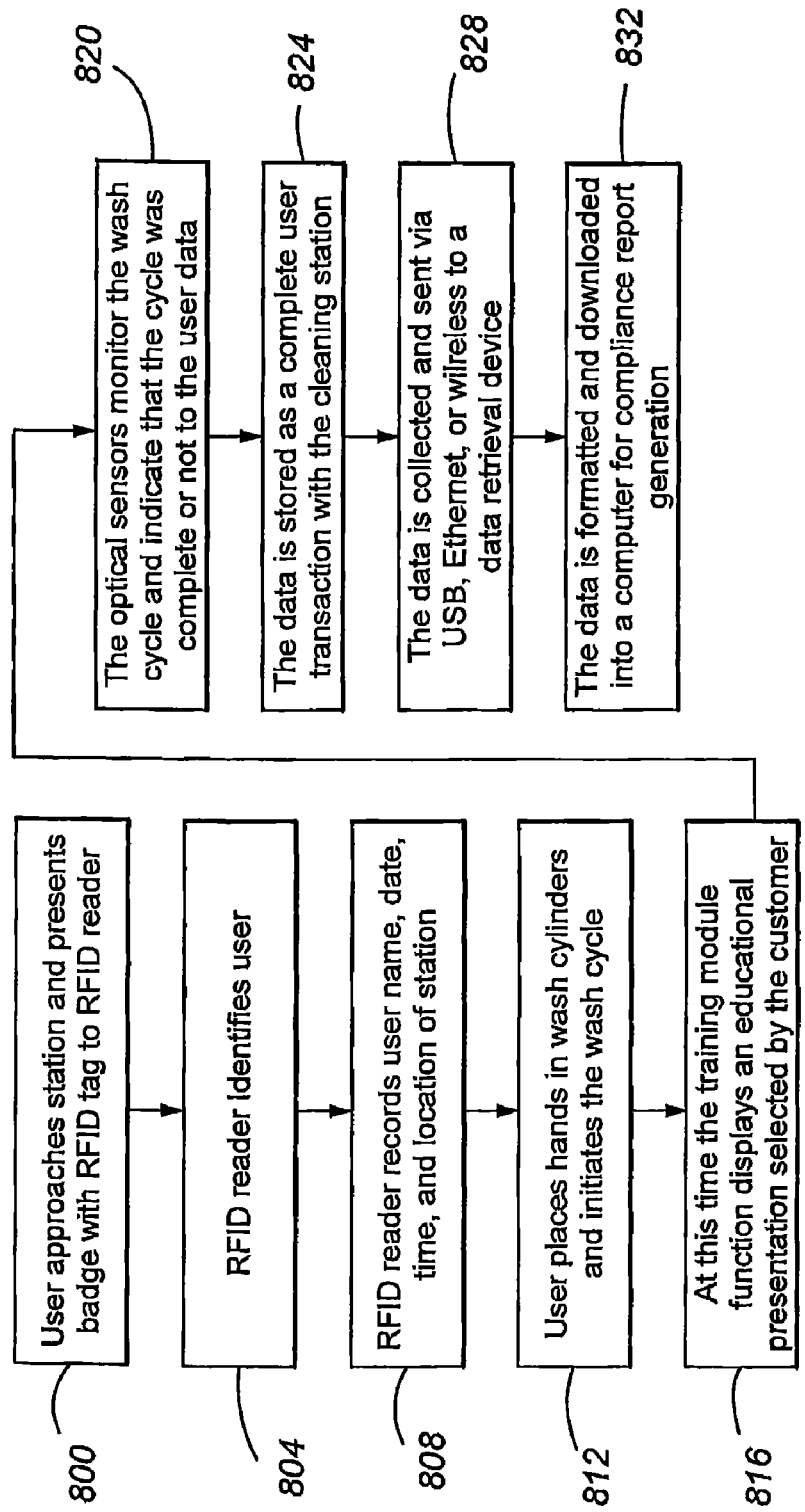
FIG. 8 is a flow chart depicting aspects of a method of monitoring hand-washing compliance in accordance with embodiments of the present invention.

In accordance with embodiments of the present invention, FIG. 8 shows a block diagram illustrating the steps of a method of monitoring a compliance requirement. Initially, at step 800 a user 204 approaches a cleaning station 100a and presents a badge having a RFID tag 208 to an RFID reader 212. At step 804 the RFID tag 208 is read and the user 204 is identified. At step 808 the user's 204 name, the date, the time, and the location of the cleaning station 100a are recorded. At step 812 a cleaning cycle is initiated when the user 204 places her or his hands in position to be washed. During the wash cycle, at optional step 816, the user 204 is provided with educational or entertainment content through the video display 224. At step 820 the wash cycle is completed and data is recorded including the duration of time the user 204 allowed his or her hands to be washed. At step 824 the transaction is completed and recorded. At step 828, data is collected from the cleaning stations 100a-100n over the communication links 108a-108n. In particular, data may be routed to a central collection point or FTP folder. Finally, at step 832, the collected data is used to generate a compliance report 640. Additional steps associated with the method may include: monitoring proper use of consumables; warning that an improper consumables container 228 has been installed; warning that a consumables container 228 is empty or nearly empty based on the number of uses since being installed; and warning that none or more users are failing to meet compliance requirements.

The present invention may be operable to track movements within a facility and/or actions taken by those located at a facility. This and other hygiene protocol monitory features are achieved through the operator of the compliance monitoring module 630. In tracking movements within a facility, the present invention is operable to track movement of both persons and objects. Additionally, embodiments of the present invention may be used to approximately track the movement of a contagion through a facility. In tracking the actions of those at a facility, the present invention is operable to track hygiene related activates that may lead to the introduction and/or spread of a contagion in a facility.

In location tracking, the present invention may define a hierarchical range of hygiene levels. Each level is assigned a number and the higher the number the more stringent the corresponding hygiene requirements. The lowest level or level 1 may specify no particular hygiene requirements. Levels above level 1 may define progressively more stringent hygiene requirements. As can be appreciated, a particular facility, such as for example, a food service establishment may have only two hygiene levels. In particular, level 1 may specify no particular hygiene requirements and level 2 may specify that a hand-washing is required. Alternatively, level 1 could have the highest hygiene requirements and levels higher than 1 (e.g. level 2) correspond to progressively lower hygiene requirements. A facility, such as for example, a hospital, may define higher level requirements that include more thorough hand-washing as well as boot-washing. Additionally, higher hygiene levels may include frock hygiene requirements.

Figure 9:
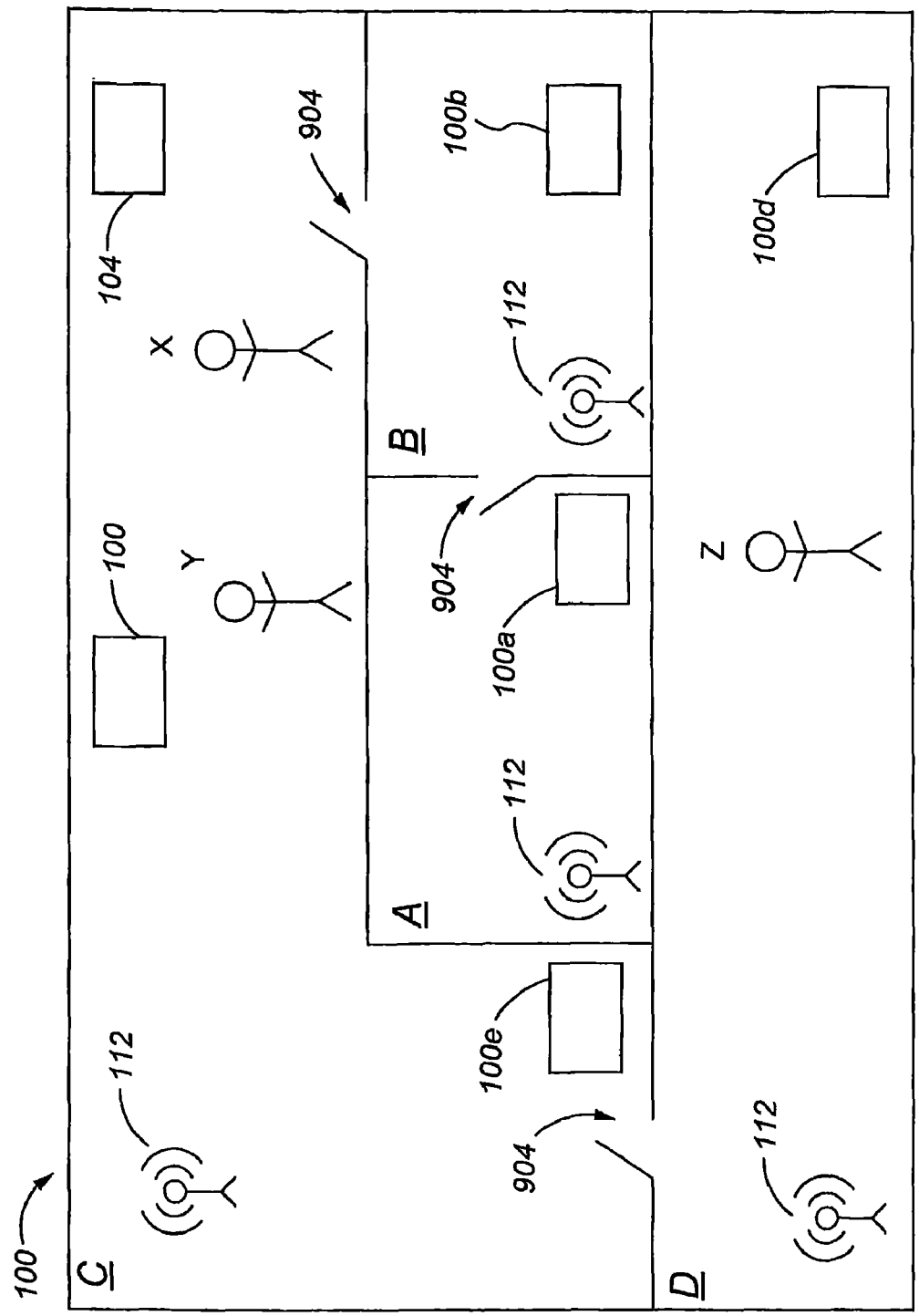
FIG. 9 is a schematic illustration of a hygiene compliance system in accordance with embodiments of the present invention.

An example of a multi-level hygiene level assignment will now be described with reference to FIG. 9. FIG. 9 is an illustration of facility having a number of different areas. The different areas A, B, C and D may correspond to different rooms and/or sections of the facility. In accordance with embodiments of the present invention, different areas correspond to different hygiene levels. For the facility shown in FIG. 9, area A is assigned a hygiene level of 1, area B is assigned a hygiene level of 2, area C is assigned a hygiene level of 3 and area D is assigned a hygiene level of 4. For example, in the instance that the facility shown in FIG. 9 is a hospital, area A might correspond to a bathroom. Similarly, area B might correspond to a waiting area, area C might correspond to a staging area, and area D might correspond to a surgery wing. As can appreciated, on or more doors or gates 904 provide a means for passing between area. The facility shown in FIG. 9 additionally includes a number of hygiene stations, such as for example, the automated cleaning station 100, shown in FIG. 2. The facility also includes an administration computer 104 and a number of RFID monitoring stations.

In accordance with embodiments of the present invention, the concept of hygiene levels may be further used to define a "hygiene status" which is associated with a particular individual. An individual's hygiene status is defined by two numerical values, which together indicate whether or not the individual is in fact or potentially in violation of a facility's hygiene protocol. The first numerical value indicates the current level of hygiene attained by the individual. As used herein, this numerical value is referred to as the individual's "hygiene radius." The second numerical value indicates the minimum hygiene level required by the area in which the individual is currently located. As used herein, the second numerical value is referred to as the individual's "working radius." Here, it should be understood that "hygiene radius" and "working radius" do not correspond to physical distances. Instead, "hygiene radius" and "working radius" correspond to numerical values that when compared with each other give an indication of an individual's hygiene status. Specifically, when an individual's hygiene radius falls below his or her working radius, a "hygiene radius violation" occurs. The consequences of a hygiene radius violation are described in detail below.

Figure 10A:
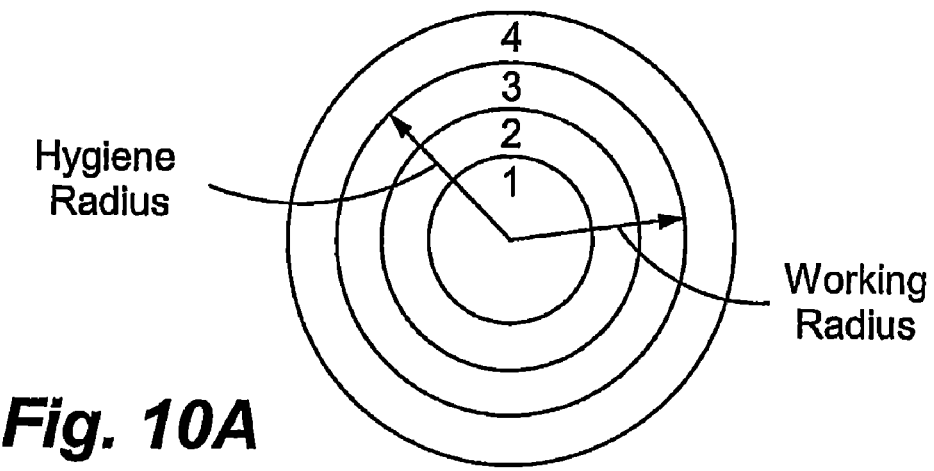
FIGS. 10A-10D are schematic representations of hygiene status in accordance with embodiments of the present invention.
Figure 10B:
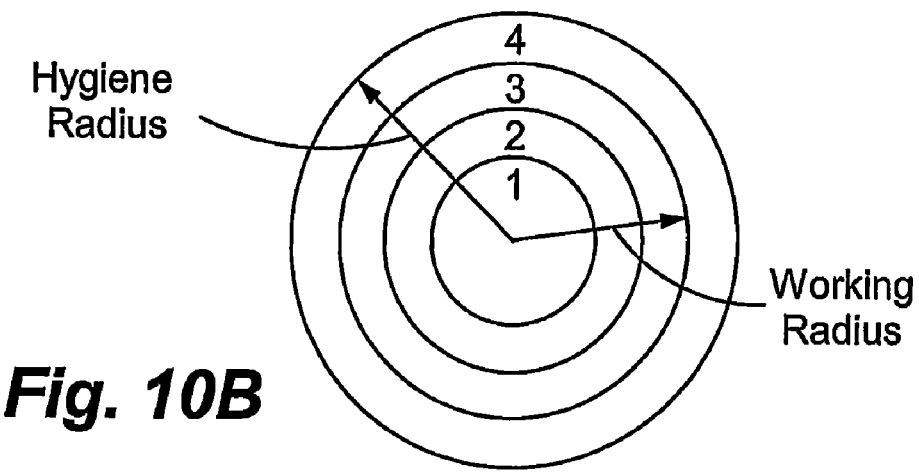
Figure 10C:
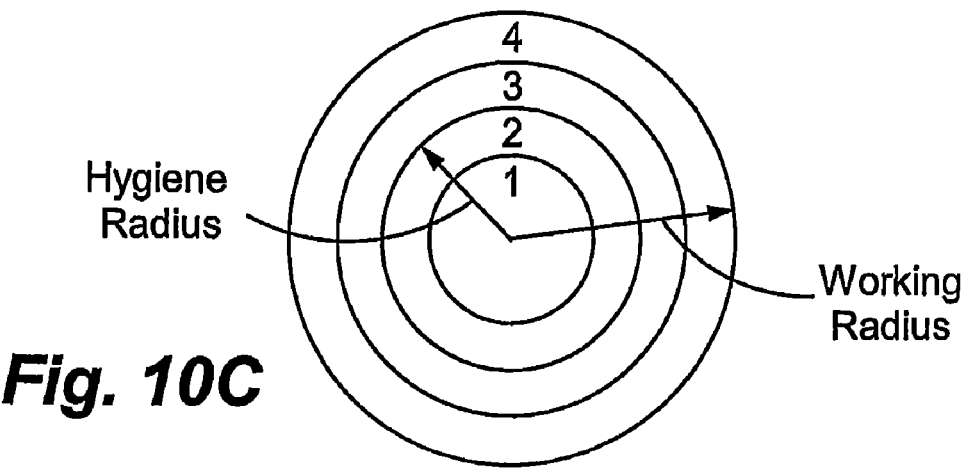
Figure 10D:
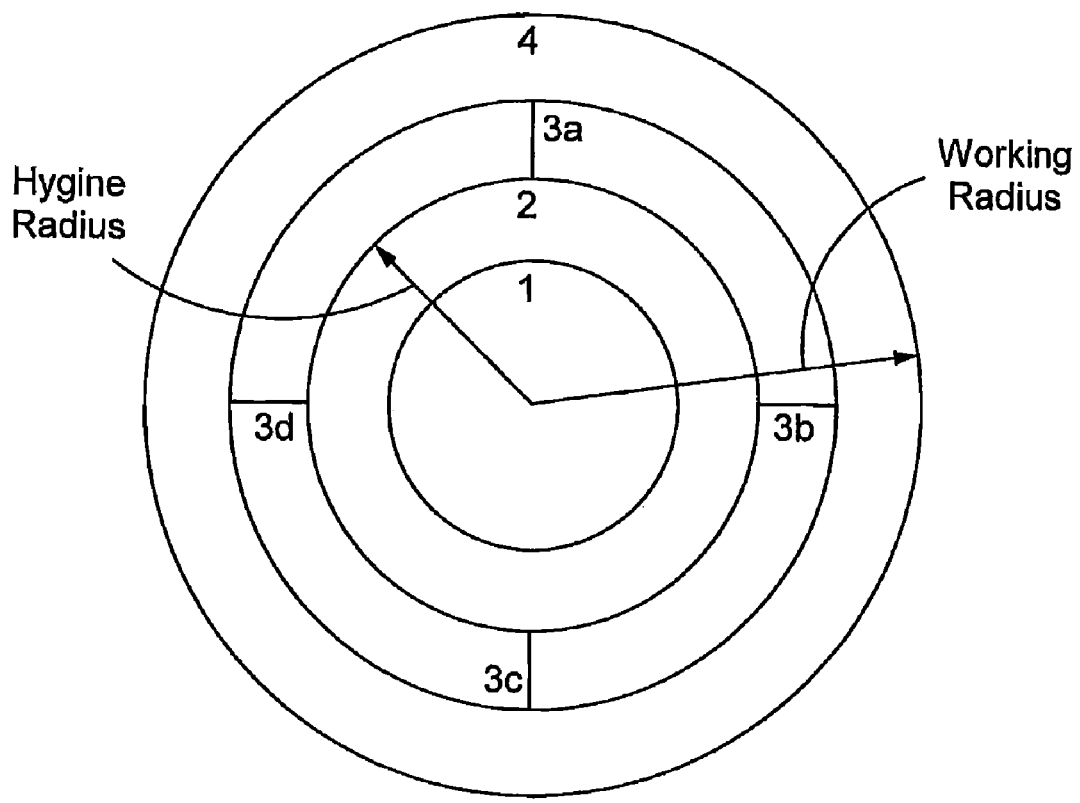

By way of illustration, FIG. 9 includes three individuals or persons, who are located within the facility. Person X is located in area C, person Y is located in area C and person Z is located in area D. In accordance with embodiments of the present invention, each of the persons will have a hygiene status by virtue of their location and current hygiene level. The above-described hygiene status scheme will now be described with reference to persons X, Y and Z. Additionally, reference is made to FIGS. 10A-10C, which include a visual representation of the hygiene status of persons X, Y and Z, respectively. Conceptually, a hygiene status in accordance with embodiments of the present invention may be understood as two radii superimposed on a set concentric circles, which represent the various hygiene levels that may be defined for a particular facility. FIGS. 10A-10C include four concentric circles corresponding to the four hygiene levels defined for the exemplary facility shown in FIG. 9.

FIG. 10A shows a visual representation of the hygiene status of person X, who is shown in FIG. 9. As can be seen in FIG. 10A, person X currently has a hygiene radius of 3 and a working radius of 3. Typically, it is the case that a person's hygiene level does not exceed the hygiene level of the room in which the person is working. More particularly, the hygiene radius does not typically exceed the working radius. Compare this to FIG. 10B, which is a visual representation of the hygiene status of person Y. As can be seen in FIG. 10B, person Y currently has a hygiene radius 4 and a working radius of 3. Having a hygiene radius greater than a working radius may be only a temporary situation. In particular, exposure to contagions, contaminants and/or other elements within the zone may occur which would degrade the hygiene radius value to 3 or more specifically, down to the current level of the zone in which person Y is located. Turning now to FIG. 10C, wherein a hygiene status for person Z is shown. The hygiene status depicted in FIG. 10C includes a hygiene radius of 2 and a working radius of 4. The situation depicted in FIG. 10B indicates a hygiene radius violation. In accordance with embodiments of the present invention, a number of sub levels may be defined with a particular hygiene level. These sub levels are non hierarchical with respect to each other. This embodiment of the present invention is illustrated in FIG. 2D.

Whether or not a hygiene radius violation is tolerated, will depend on the particular hygiene protocol implemented by a facility. Under a more stringent hygiene protocol, a hygiene radius violation may lead to a hygiene protocol violation. As used herein, a "hygiene protocol violation" indicates that the person is out of compliance with the facility's hygiene protocol and in embodiments of the present invention, which provide a monitoring of the facility's hygiene performance, the individual's hygiene protocol violation will be recorded.

Within a more stringent hygiene protocol, different degrees of stringency may be defined. For instance, a hygiene protocol violation may occur only after a predetermined time from which a hygiene radius occurred. Alternatively, a hygiene radius violation may immediately result in a hygiene protocol violation. In still other instances, a facility may force an individual to have the required hygiene level prior to entry into a particular hygiene zone. Here, a hand washing station may be provided in the near the boundary between hygiene zones. This hand-washing station may be electronically coupled to a door, which provides ingress into the higher-level hygiene zone, as described in greater detail below.

In contrast to the more stringent hygiene protocols defined above, a looser hygiene protocol may be defined. Here, a hygiene radius violation may be tolerated. In particular, a hygiene radius violation is not raised to a hygiene protocol violation. Instead, in response to a hygiene radius violation, an individual may simply be made aware of the fact that a hygiene related action is required or recommended.

Under any particular hygiene protocol, one or more action (s) may be taken to remedy a hygiene radius violation. For instance, the individual may be instructed or required to wash his hands. Alternatively, the individual may be instructed to wash one or more articles of clothing, such as a boot or frock. In accordance with yet another alternative embodiment of the present invention, the individual may be locked out from using facility related equipment and/or a designated work station or area. For instance, if the individual is working in a food service environment, that person's food prep station may be mechanically locked out and/or logically (e.g. by software disable). In that regard, the individual will be physically prevented from accessing any food items. In some instances, a warning may be given. This warning indicates to the individual that a hygiene radius violation has been detected or encountered. The individual may then have a certain limited time to remedy the hygiene radius violation by taking such steps as washing his or her hands. If the individual fails to address the hygiene radius violation, the hygiene radius violation may then be raised to a hygiene protocol violation. In other instances, a lower than required hygiene radius will not be tolerated. Here, once a hygiene radius violation occurs, a protocol violation will immediately occur.

In response to a hygiene radius violation, an individual may perform a hygiene related action and as a consequence have his or her hygiene radius upgraded. As a result of having his hygiene radius upgraded, it may no longer be the case that his hygiene radius is lower than his working radius. Accordingly, the hygiene radius violation may be cleared.

As mentioned above, a hygiene radius violation corresponds to the situation wherein an individual's hygiene radius is below his or her working radius. As can be appreciated, this situation can be brought about by changes in either an individual's hygiene radius or changes in the individual's working radius. In some instances, a change in an individual's working radius can impact the individual's hygiene radius. It should be noted however, that the reverse is not the case. Specifically, a change in an individual's hygiene radius will not impact the individual's working radius. An individual's working radius simply corresponds to the required hygiene level for the area in which he or she is located. These concepts are explained in more detail with reference to FIG. 11A through FIG. 11D, which show a schematic of the facility shown in FIG. 9.

Figure 11B:
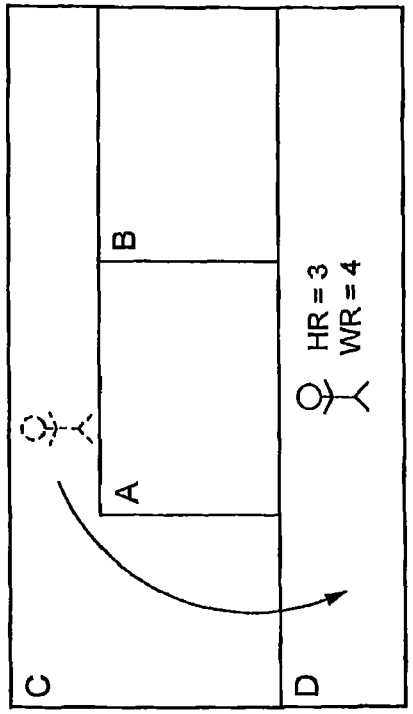
FIGS. 11A-11D are schematic illustrations of the system shown in FIG. 9.
Figure 11D:
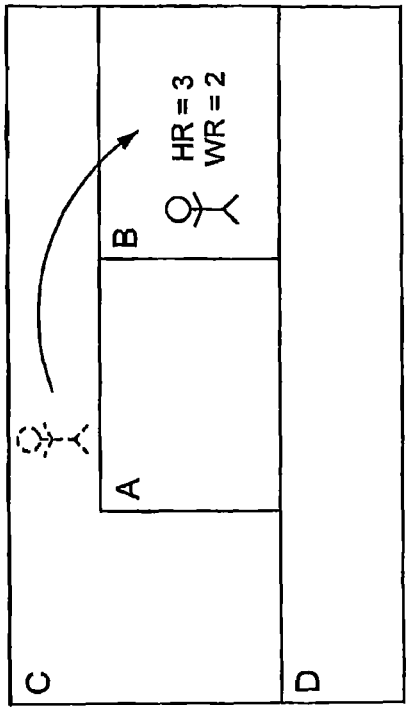
Figure 11A:
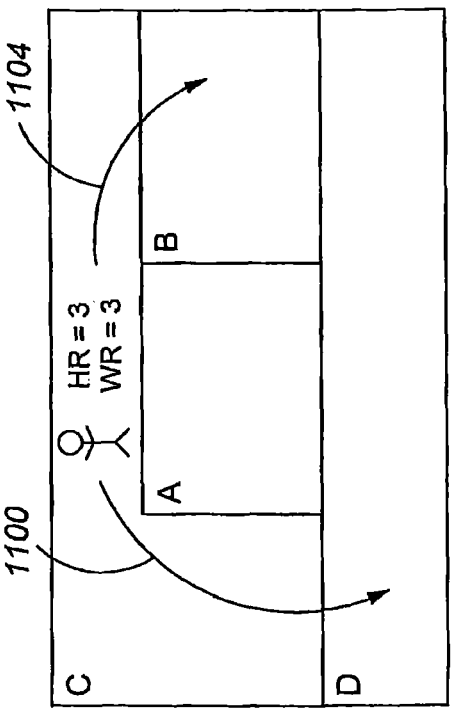

As shown in FIG. 11A, person X is located in area C. As shown in the figure, his hygiene radius is 3 and his working radius is 3. If the individual leaves the area in which he is currently located, his hygiene status may be affected. In FIG. 11A, there are shown two possible paths person X may take in leaving area C. Arrow 300 indicates leaving zone C and entering zone D. Arrow 304 indicates leaving zone C and entering zone B.

As shown in FIG. 11B, person X takes the path indicated by arrow 1100 from the zone C into zone D. As indicated in the figure, when in zone D the individual's hygiene radius remains at 3, while his or her working radius is raised to 4. This is the case because the individual had a previous hygiene level of 3 and entered into a working area having a hygiene level of 4. Having not yet undergone or performed hygiene related action, his hygiene radius remains constant. As his hygiene radius is now less than his working radius, which corresponds to a hygiene radius violation.

The hygiene radius violation depicted in FIG. 11B resulted from a change in an individual's working radius, with no corresponding change in his hygiene radius. As the individual crossed into a higher level hygiene zone, a hygiene radius violation occurred. In particular, the individual's working radius value was increased while his hygiene radius remained constant, thereby resulting in a higher working radius than hygiene radius, and consequently in a hygiene radius violation.

Figure 11C:
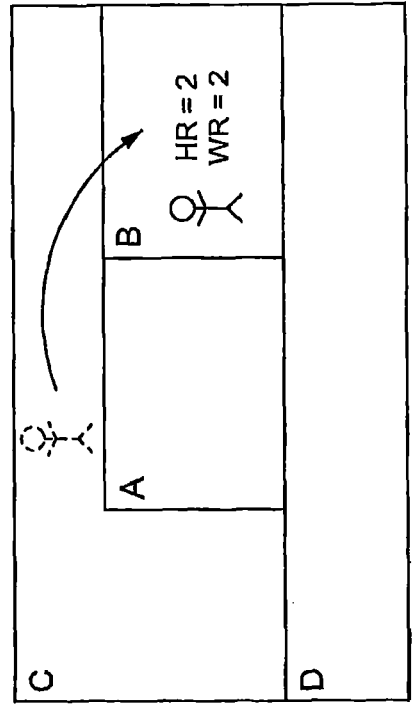

In FIG. 11C, person X takes the path indicated by arrow 1104 into zone B. As zone B is at a lower hygiene level than zone C, this movement by the person X does not involve a hygiene radius violation. As shown in FIG. 11C, person X, upon entry into zone B, has a hygiene radius of 2 and a working radius of 2. The situation depicted in FIG. 11C is one embodiment of the present invention, which corresponds to the requirement that a hygiene radius immediately be downgraded once a lower level hygiene zone is entered. The requirements imposed on the individual may vary depending on the hygiene protocol implemented by the facility.

In FIG. 11D, person X takes the path indicated by arrow 1104 into zone B. As shown in FIG. 11D, person X, upon entry into zone B, does not have his hygiene radius immediately downgraded. Here, person X has a hygiene radius of 3 and a working radius of 2. The situation depicted herein is one embodiment of the present invention, which corresponds to the situation where immediate downgrading of the hygiene radius is not required. As used herein, this situation is referred to a "contingent downgrade" of a hygiene radius.

Here, the downgrading of an individual's hygiene radius value may be contingent on a number of factors. For instance, the downgrading of the individual's hygiene radius may be dependent on the amount of time spent in a particular hygiene zone. Alternatively, downgrading of the hygiene radius may be contingent on the individual's contact with one or more objects located within the contamination zone.

Figure 12C:
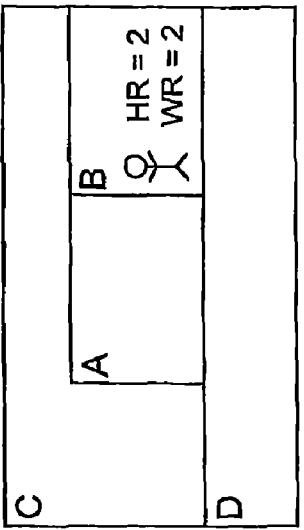
Figure 12B:
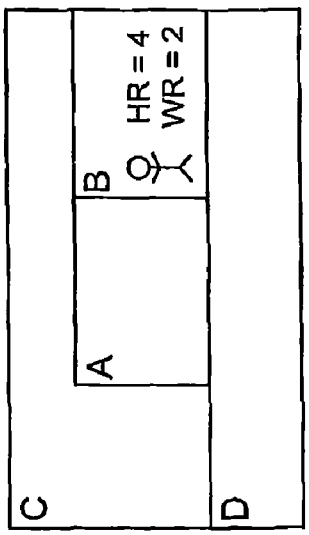
Figure 12A:
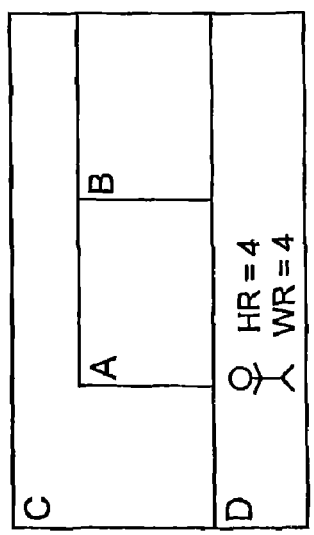
Figure 12E:
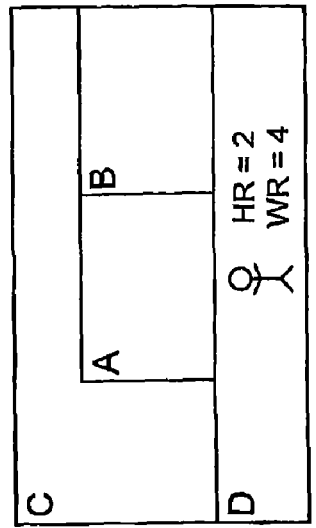
Figure 12D:
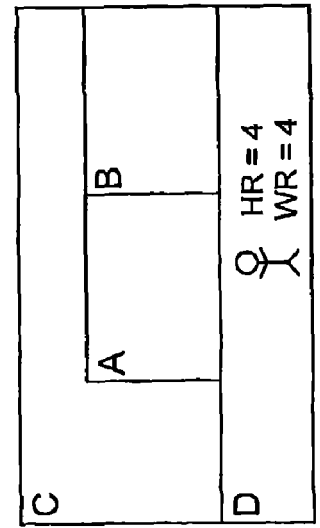

Turning now to FIGS. 12A-12E, the concept of contingent downgrade of the hygiene radius value is further illustrated. Specifically, FIGS. 12A-12E illustrate the concept of time dependent contingent downgrade of a hygiene radius. As shown in FIG. 12A, an individual is located in area D. Here, the individual has a hygiene radius of 4 and a working radius of 4. In FIG. 12B, the individual moves from area D into area B. Here, the downgrading of the individual's hygiene radius is contingent on the amount of time spent in the lower level hygiene zone. Accordingly, the individual's hygiene radius value initially remains at 4, while his working radius is lowered to 2. As shown in FIG. 12C, the individual very quickly returns to area D. Here, the individual's hygiene radius remains at 4 upon his return to the area D. Alternatively, the individual may decide to remain in zone B for an extended period of time. This situation is shown in FIG. 12D. Here, the prolonged exposure to zone B results in a downgrading of the individual's hygiene radius to a value of 2, or, equivalently, to the same value as is in effect in the area in which he is located. FIG. 12E indicates the situation where the individual eventually returns to the area D after having been in area B for an extended period of time. Crossing into level 4 results in his working radius being raised to level 4. Having not yet performed a hygiene action, his hygiene radius value remains at level 2. Accordingly, a hygiene radius violation occurs.

It should be understood that the situation depicted in FIGS. 12A-12E corresponds to a looser hygiene compliance protocol. The situation is not necessarily inappropriate, it is just an illustration of a particular situation that may meet the needs of a particular facility.

Figure 13A:
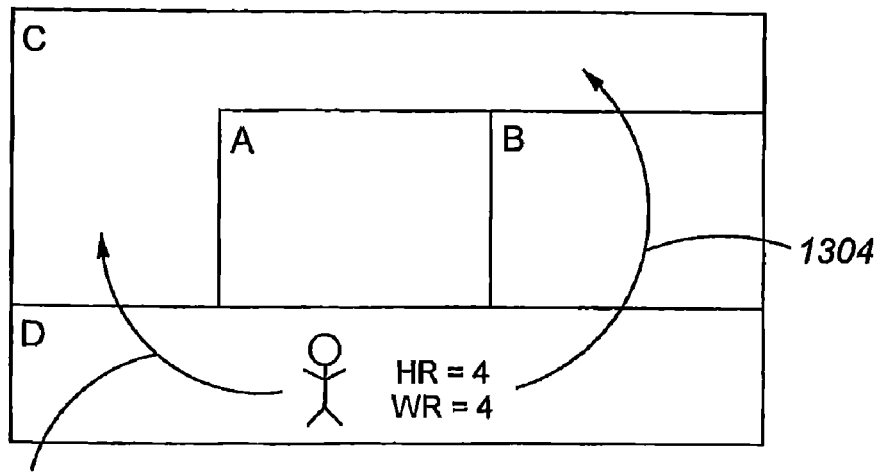
FIGS. 13A-13C are additional schematic illustrations of the system shown in FIG. 9.
Figure 13B:
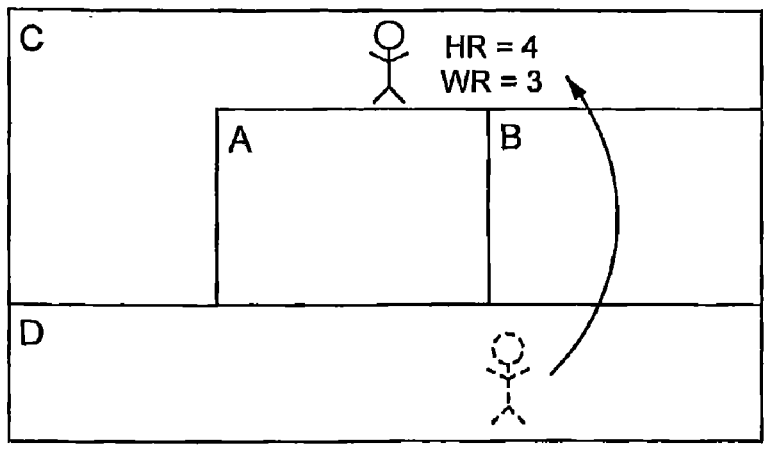
Figure 13C:
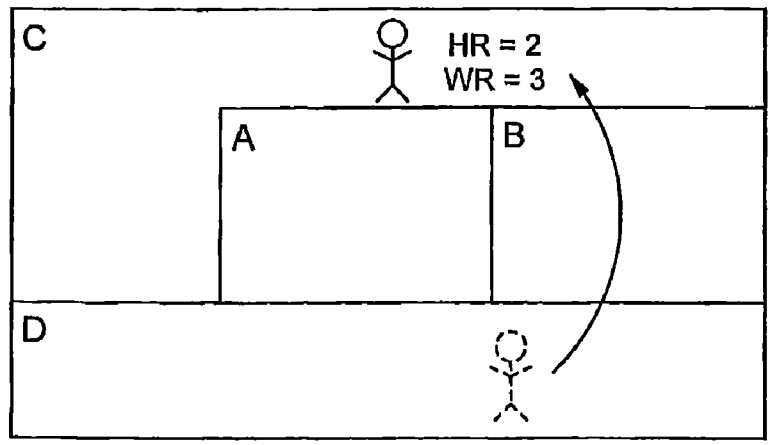

As shown in FIGS. 13A-13C, using contingent downgrading of hygiene radius values may allow an individual to transition through a lower level hygiene area, provided the individual does not remain in that lower level hygiene area for an extended period of time. Referring to FIG. 13A, an individual can be seen located in area D. As shown in FIG. 13A, the individual may take two different paths into zone C. The first path indicated by arrow 1300 takes the individual directly into area C. The path indicated by arrow 1304 takes the individual into the area C by way of passing through area B. As can be appreciated, the path indicated by arrow 1300 will not result in a hygiene radius violation. In particular, the individual has a hygiene radius of 4 and is entering into a lower level hygiene area, namely a hygiene area requiring hygiene level of 3. In contrast, the result of taking the path indicated by arrow 1304 may result in different actions being taken depending upon the facility's hygiene compliance protocol. In particular, if contingent hygiene radius downgrading is allowed, then an individual may be allowed to transition through the area B, without adversely affecting his hygiene radius value. This situation is depicted in FIG. 13B. Alternatively, if contingent hygiene radius downgrade is not allowed, then the individual will not be allowed to transition through area B without adversely affecting his hygiene radius value. This situation is depicted in FIG. 13C. In FIG. 13B, the individual arrives in area C with a hygiene radius value of 4, and in FIG. 13C, the individual arrives in C with a hygiene radius value of 2.

The above discussions of the present invention address the situation wherein a hygiene radius downgrade and/or a hygiene radius violation occurs as a result of movement of an individual through a facility. Monitoring of such a situation is illustrated in the flow chart shown in FIG. 14, which shows the operation of the compliance monitoring module 630.

Figure 14:
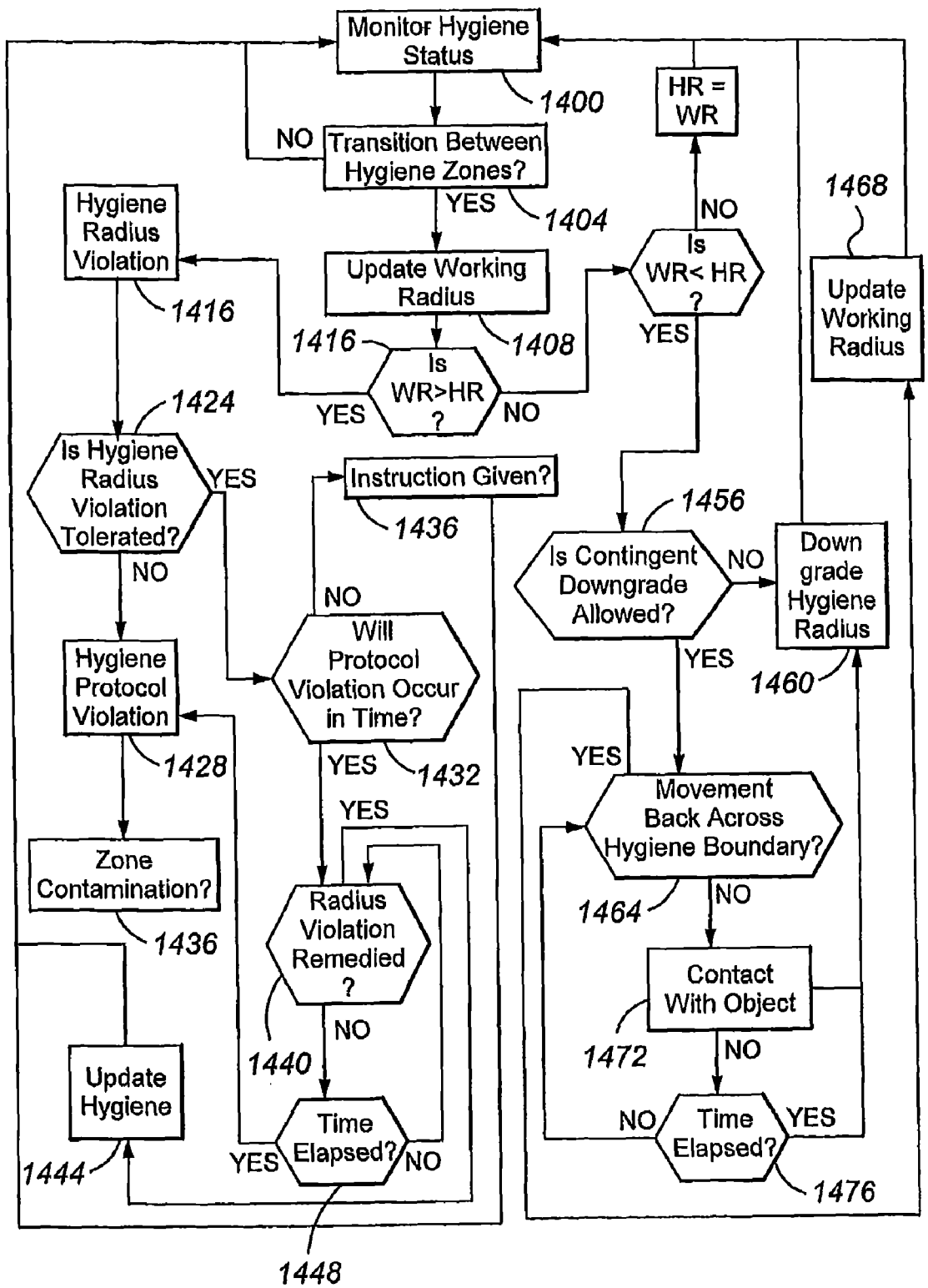
FIG. 14 is a flow chart illustrating a hygiene monitoring method in accordance with embodiments of the present invention.

Referring now to FIG. 14, at step 1400, a hygiene status of one or more individuals is monitored. At step 1404, a transition between hygiene zones is detected. If no detection of a transition between hygiene zones occurs, step 1400 again follows. If a transition between hygiene zones occurs, step 1408 follows.

At step 1408, the working radius of the individual who transitioned between hygiene zones is updated. In particular, the hygiene level for the zone in which the individual is currently located is given as the individual's hygiene radius.

In step 1412 which follows step 1408, a determination is made as to whether the individual's working radius is greater than his hygiene radius. If the individual's working radius is greater than his hygiene radius, step 1416 follows. Alternatively, if the individual's working radius is not greater than his hygiene radius, step 1420 follows.

At step 1416, a hygiene radius violation occurs or is issued. At step 1424, a determination is made as to whether the hygiene radius violation is tolerated. If they hygiene radius is not tolerated, step 1428 follows. Alternatively, if the hygiene radius violation is tolerated, step 1432 follows.

At step 1428, a protocol violation occurs. Specifically, the hygiene radius violation is raised to the level of a protocol violation. This may or may not lead to a zone contamination, which is indicated in step 1436 and which is discussed in greater detail below.

Turning now to step 1432, wherein the hygiene radius violation may be tolerated. At step 1432, a determination is made as to whether a protocol violation will occur in time. If no protocol violation will occur, step 1436 follows. Here, one or more instructions may be given in order to advise the individual of his hygiene radius violation. Alternatively, the hygiene radius violation may be recorded. Regardless of the actions taken at step 1436, the method proceeds therefrom to step 1400, where again hygiene status is monitored.

Turning now to step 1440, wherein the facility's hygiene protocol specifies that a hygiene protocol violation will occur in time if the hygiene radius violation is not remedied. Accordingly, at step 1440 a determination is made as to whether the hygiene radius violation has been remedied. In remedying a hygiene radius violation, an individual may undergo or perform one or more hygiene related activities such as hand-washing, boot-washing and/or frock washing. If at step 1440 the hygiene radius violation is remedied, step 1444 will follow. If, at step 640, the hygiene radius violation is not remedied, step 1448 will follow.

Referring now to step 1444, wherein the individual has remedied his or her hygiene radius violation. At step 1444, the individual's hygiene radius will be updated. In particular, as a result of the hygiene related actions taken by the individual, his hygiene radius will be raised to an appropriate level. Following step 1444, the method will then proceed to step 1400, wherein hygiene status is again monitored.

Turning now to step 1448, wherein an individual has not taken steps to remedy the hygiene radius violation. In step 1448, a determination is made as to whether the allotted time for remedying the situation or remedying the hygiene radius violation has expired. If the time has not elapsed, step 1440 again follows step 1448, wherein the hygiene radius violation is continually monitored. If, in step 1448 the time has in fact elapsed, step 1428 will follow. As described above, in step 1428, a protocol violation occurs or is issued as a result of the protocol violation. In step 1436, a zone contamination may occur which is described in greater detail below.

Turning now to step 1420, wherein it was determined that the working radius was not greater than the hygiene radius. At step 1420, a determination is made as to whether the working radius is less than the hygiene radius. If the working radius is not less than the hygiene radius, step 1452 follows. At step 1452, it is the case that the hygiene radius equals the working radius or, equivalently, the individual has transitioned across hygiene zones and that transition did not result in a change in the individual's working radius.

Step 1456 will follow step 1420 if it is the case that the working radius is less than the hygiene radius. At step 1456, a determination is made as to whether contingent downgrade of the hygiene radius is allowed. If contingent downgrade is not allowed, step 1460 will follow. Alternatively, if contingent downgrade is allowed, step 1464 will follow.

In step 1460, a contingent downgrade is not allowed. In step 1460, the individual's hygiene radius is immediately downgraded. In particular, the individual's hygiene radius is made equal to the working radius or rather the hygiene level in which the individual is located. Step 1400 follows step 1460. In particular, after the hygiene radius has been downgraded, the system continues to monitor hygiene status.

In step 1464, a contingent downgrade is allowed. At step 1464, a determination is made as to whether the individual has moved back across the hygiene boundary from where he came. If in fact the individual has moved back across the hygiene boundary, step 1468 follows. If the individual remains within the current hygiene zone, step 1472 follows.

In step 1468, the individual has moved back across the hygiene boundary. In step 1468, the individual's working radius is updated accordingly. In particular, his working radius is assigned to the working radius associated with the previous hygiene zone from which he came. Following step 1468, the method proceeds again to step 1400 wherein a hygiene status is monitored.

Turning to step 1472, wherein the individual has not moved back across the hygiene boundary. In step 1472, which is an optional step, it is determined if the individual has come in contact with an object in the lower level hygiene zone. If the individual has come in contact with an object in the lower level hygiene zone, step 1460 follows. If the individual has not come in contact with an object in the lower level hygiene zone, step 1476 follows.

As described above in step 1460, the individual's hygiene radius is downgraded. Here, this downgrading of the hygiene radius is a result of the individual's contact with one or more objects in the lower level hygiene zone.

Turning now to step 1467, a determination is made as to whether the allowed time has elapsed. Specifically, the allowed time is the time an individual is allowed to remain in a lower level hygiene zone without his hygiene radius being downgraded. If the time has elapsed, step 1460 follows. Alternatively, if the time has not elapsed, step 1464 follows. As described above, step 1460 leads to the downgrading of the hygiene radius and continued monitoring, whereas step 1464 leads to the continued monitoring of the individual without yet downgrading his hygiene radius.

Figure 15:
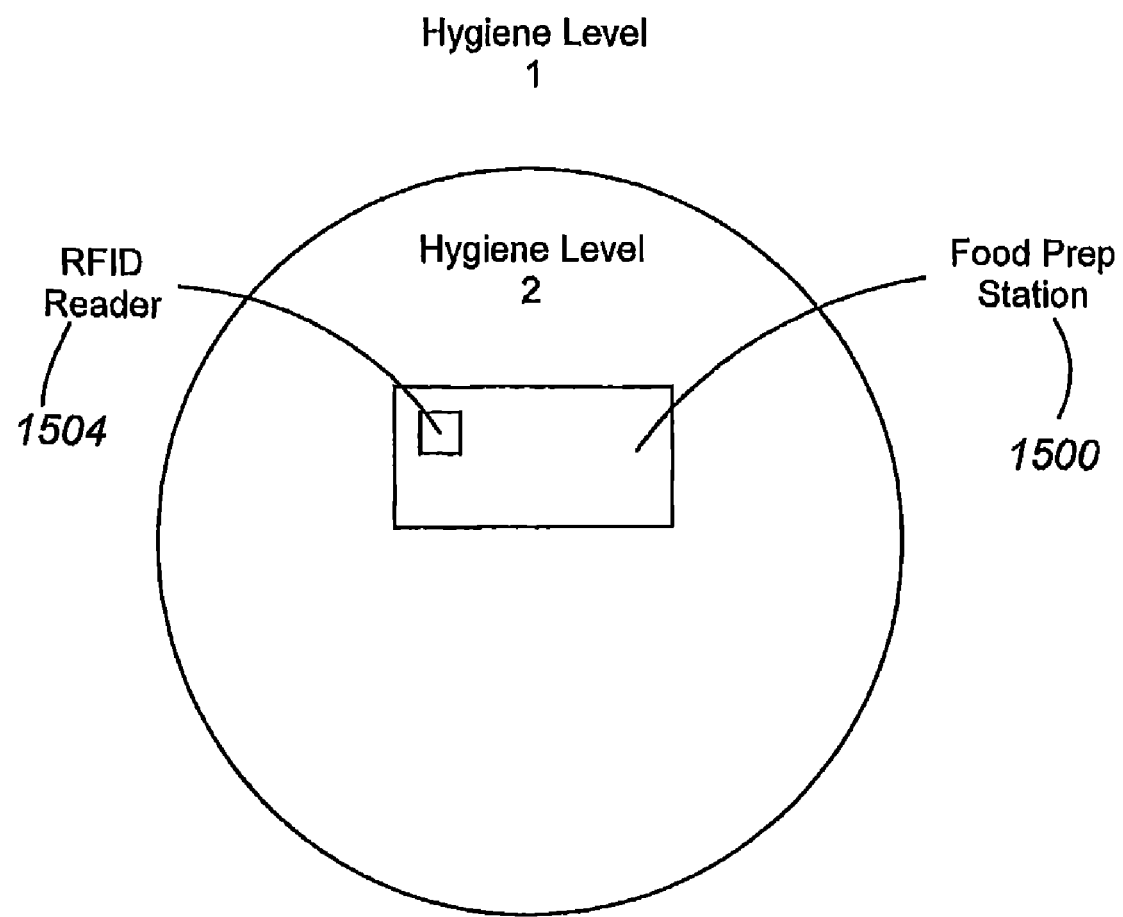
FIG. 15 is an illustration of a particular allocation of hygiene levels in accordance with embodiments of the present invention.

In the above discussions, boundaries between hygiene zones are considered to coincide with certain walls within a facility. However, it should be understood that the present invention does not require this to be the case. For instance, in accordance with embodiments of the present invention, an individual may be considered to have crossed a boundary between hygiene zones when that individual moves beyond the range of a particular RFID reader. This may be the case, for example, for a person who is working at food prep station. Here, a RFID reader may be associated with the food prep station and may be operable to read an RFID tag associated with the person provided that the person does not exceed a certain distance from the food prep station. FIG. 15 shows the allocation of hygiene levels for this exemplary food prep station. As shown if FIG. 15, the area in the immediate vicinity of the food prep station 1500, or, equivalently the range of the RFID reader 1504 is assigned to a hygiene level of 2. The entire area outside of the range of the RFID reader is assigned to a hygiene level of 1.

With this assignment of hygiene levels, the operation of the compliance monitoring module 630 can be understood with reference to FIG. 14. At step 1400, the individual's hygiene status is monitored. With reference to FIG. 15, this would include the individual working and/or located at the food prep station. As described above, the individual leaves his food prep station and exceeds the range of the RFID reader 1500 which is associated with the food prep station. Referring to FIG. 14, this transition between hygiene zones is detected at step 1404. Accordingly, at step 1408, the individual's hygiene radius is updated. In particular, as he is transitioned from a hygiene zone having a level of two into a hygiene zone having a level one, his hygiene radius is changed from two to one.

In step 1412, a determination is made as to whether his working radius is greater than his hygiene radius. It should be noted at this point that as the individual came from a hygiene zone having a hygiene level of 2, it is assumed that the individual's current hygiene radius upon crossing the boundary between hygiene zones is 2. Accordingly, at step 1412, it is determined that the individual's working radius is not greater than his hygiene radius.

At step 1420 it is determined that the individual's working radius is less than his hygiene radius. Accordingly, step 1456 follows. At step 1456, a determination is made as to whether contingent downgrading is allowed. As described above, this is not the case for the particular hygiene protocol which is in place. Accordingly, step 1460 follows. At step 1460, the individual's hygiene radius is downgraded. More particularly, the individual's hygiene radius is assigned to the hygiene level in which he is located. Specifically, the individual is given a hygiene radius value of 1. After step 1460, the method proceeds to 1400, wherein the individual's hygiene status is again monitored.

The monitoring continues until the point as described above wherein the individual returns to his food prep station. Here, at step 1404, a transition between hygiene zones is again detected. Accordingly, at step 1408, the individual's working radius is updated. More particularly, the individual's hygiene radius is assigned to the hygiene level in which he is currently located. With reference to FIG. 15, this corresponds to assigning the individual a working radius of 2.

At step 1412, a determination is again made as to whether the individual's working radius is greater than his hygiene radius. In this instance, it is the case that the individual's working radius is greater than his hygiene radius. Specifically, his working radius is at a level of 2 and his hygiene radius is at a level of 1. Accordingly, step 1416 follows.

At step 1416, a hygiene radius violation occurs. From step 1416, the method may proceed as described above and will depend on the particular hygiene protocol in place at the facility. As is described above, this may include giving instructions to the individual to remedy his hygiene status and/or mechanically locking out the individual's work station pending a hygiene related action.

The hygiene monitoring system 100 is described above mainly in connection with a facility that defines multiple hygiene zones. However, it should be understood that the hygiene monitoring system 100 may be used in connection with a facility that defines only two hygiene zones, namely a hygienic area and a non-hygienic area. Once such facility was described in connection with FIG. 15. In the instance that only two hygiene levels are defined, a hygiene radius may be defined in terms of boolean values rather than a range of numerical values.

In accordance with embodiments of the present invention, a hygiene radius violation may lead to a zone contamination. As used herein, a "zone contamination" refers to the situation wherein the required hygiene level for a particular zone has been violated. This may lead to a further downgrading of other individuals' hygiene radii who may be located within the contaminated zone. Additionally, alerts may be issued to require a zone remediation. In particular, the zone must be cleaned and/or disinfected prior to the removal of the alert and/or the removal of the indication of a contaminated status.

Figure 16A:
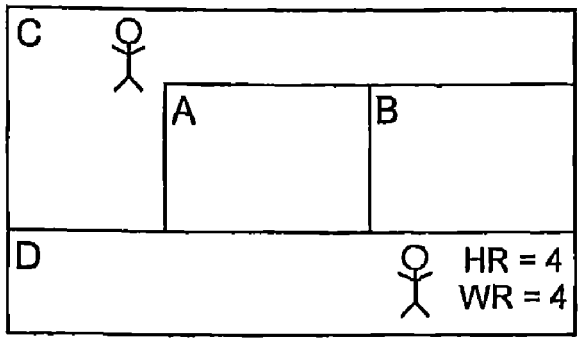
FIGS. 16A-16B are additional schematic illustrations of the invention shown in FIG. 9.
Figure 16B:
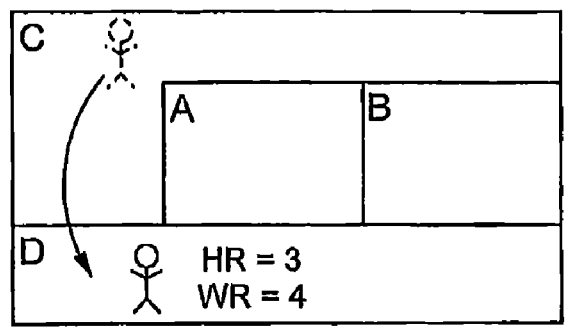

Turning now to FIG. 16A and FIG. 16B, zone contamination is illustrated. In particular, an individual who is located in area C enters into the area D. If this transition is made without the individual raising his hygiene radius value to 4, then a zone contamination may occur. If the facility's hygiene protocol so stipulates, this zone contamination may occur immediately as the individual enters into the higher level hygiene area. Alternatively, the zone contamination will occur after a predetermined amount of time has elapsed. As a result of a zone contamination, any individuals within the contaminated zone will have their hygiene radius values downgraded. In this regard and as a result, each individual so downgraded will thereby encounter a hygiene radius violation. The facility may respond to a zone contamination in a number of ways. In particular, a zone remediation procedure may be initiated wherein the contaminated zone is decontaminated.

Figure 17A:
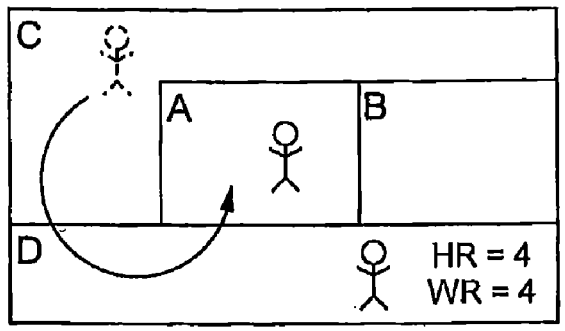
FIGS. 17A-17B are additional schematic illustrations of the invention shown in FIG. 9.
Figure 17B:
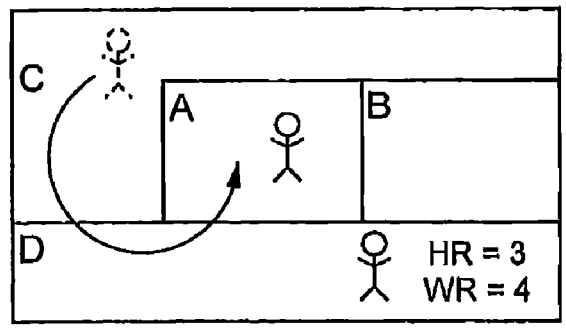

Turning now to FIGS. 17A and 17B, the concept of zone contamination is further illustrated. Whether or not a zone contamination occurs may depend on the length of time in which the individual having a lower than required hygiene value remains in the higher level hygiene zone. FIG. 17A depicts the situation where immediate zone contamination is required and FIG. 17B indicates the situation when contingent zone is allowed. In FIG. 17A, the individual travels from zone C to zone B by way of zone D. Here, if the individual makes this transition in a sufficiently fast amount of time, zone contamination will not occur and individuals within the zone will not have their hygiene radius values downgraded. Alternatively, as depicted in FIG. 17B, if contingent zone contamination is not allowed, the individual's transit through the zone will result in zone contamination regardless of how fast the transition occurs. Here, any individuals within the contaminated zone will have their hygiene radius values downgraded, specifically downgraded 3, or equivalently, the hygiene level of the person who caused the zone contamination.

Figure 18A:
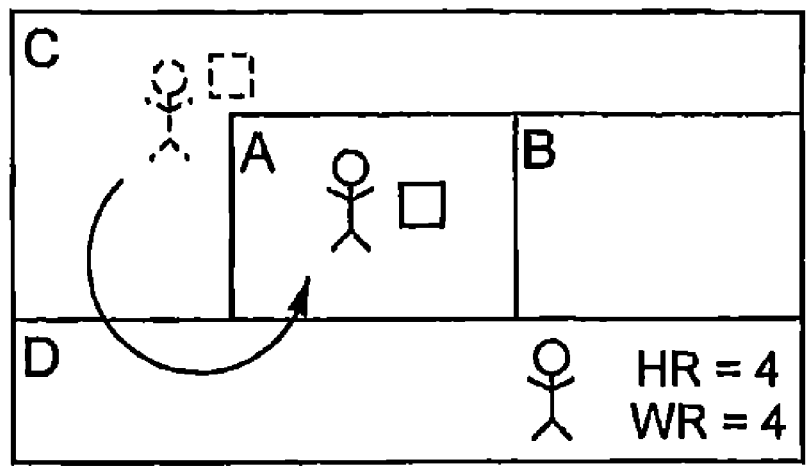
FIGS. 18A-18B are additional schematic illustrations of the invention shown in FIG. 9.
Figure 18B:
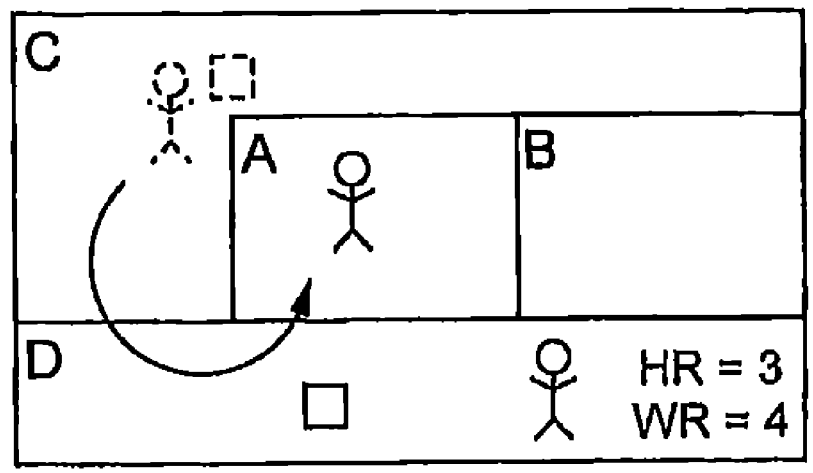

Turning now to FIGS. 18A and 18B, as shown herein an individual carries an object from C through zone D and into zone B. If contingent zone contamination is allowed, this does not necessarily result in a zone contamination. However, it may be the case that the individual leaves behind the object in zone D, and leaves zone D to enter zone B. Here, the object which came from the level 3 area may result in a zone contamination provided that it is left there for a sufficient amount of time. As shown in FIG. 18B, the zone contamination results in a downgrading of individuals within the zone or individual's hygiene radiuses who are located within the zone.

Figure 19:
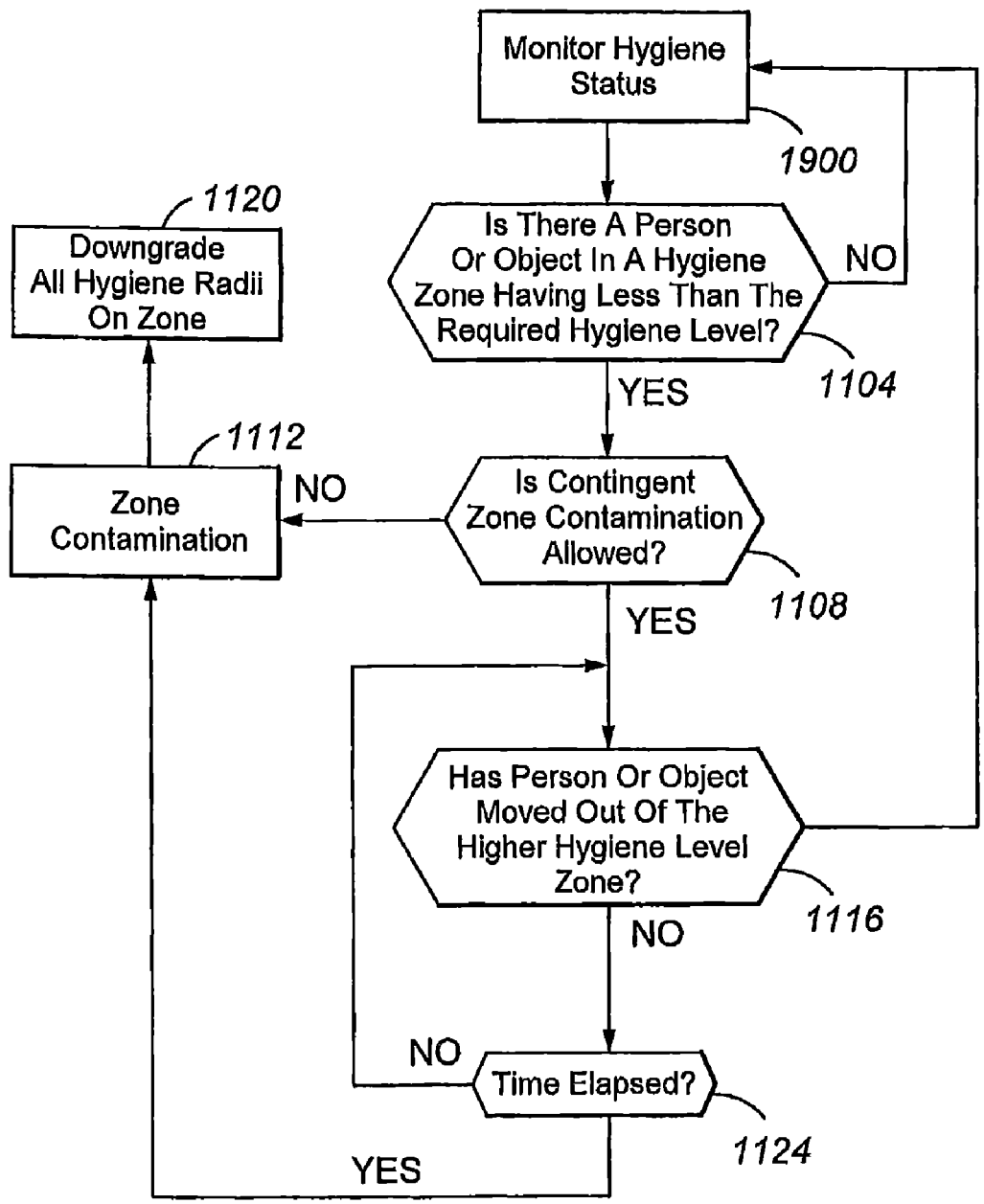
FIG. 19 is a flow chart showing yet another hygiene monitoring method in accordance with embodiments of the present invention.

The above discussions of the present invention address the situation wherein a zone contamination occurs as a result of a hygiene protocol violation. This aspect of the present invention is summarized in the flow chart shown in FIG. 19. At step 1900, hygiene status is monitored. At step 1904, a determination is made as to whether there is a person or object in the monitored hygiene zone having less than the required hygiene level. If this is not the case, step 1900 again follows. If this is the case, step 1908 follows. In step 1908, a determination is made as to whether contingent zone contamination is allowed. If contingent zone contamination is not allowed, step 1912 follows. If contingent zone contamination is allowed, step 1916 follows.

Turning to step 1912, wherein contingent zone contamination is not allowed. If this is the case at step 1912, a zone contamination occurs. As a result of the zone contamination, step 1920 follows, wherein all individuals within the contaminated zone have their hygiene radii downgraded. Here, it is additionally noted that the facility may take additional steps to remediate zone contamination, specifically initiating procedures to cleanup and/or decontaminate the contaminated zone.

Turning to step 1916, wherein contingent zone contamination is allowed. At step 1916, a determination is made as to whether the person or object has moved out of the higher-level hygiene zone. If the person has moved out of the higher level hygiene zone, step 1900 follows, wherein hygiene status is continually monitored. If the person has not moved out of the higher-level hygiene zone, step 1924 follows.

At step 1924, a determination is made as to whether the allotted time has expired. Specifically, a determination is made as to whether the time in which a person or object is permitted to remain in a higher level hygiene zone. If the time has expired, step 1912 follows. If the time has not expired, step 1916 follows.

As described in detail above, at step 1912 a zone contamination occurs. Herein the zone contamination occurs as a result of the individual remaining within the higher level hygiene zone or a longer than permitted period of time.

Figure 20A:
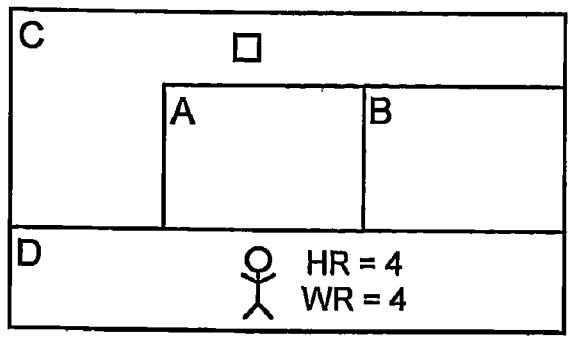
FIGS. 20A-20D are additional schematic illustrations of the invention shown in FIG. 9.
Figure 20B:
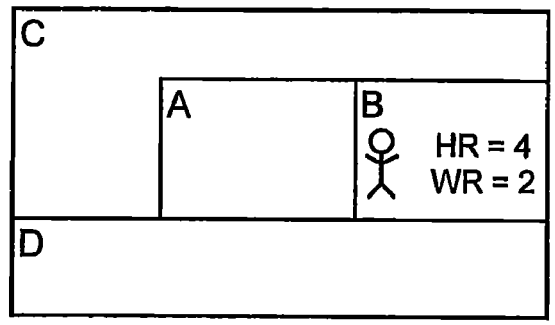
Figure 20C:
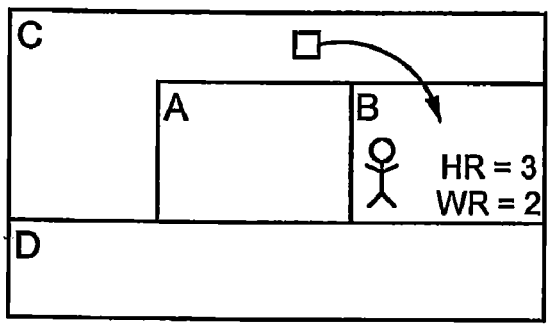
Figure 20D:
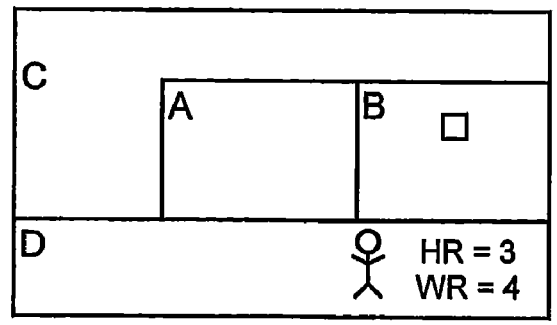

Referring now to FIG. 20A-D, a situation is illustrated involving contingent downgrade of radius values and contingent contamination zones. As shown in FIG. 20A, an individual is in the area D. The individual has a hygiene radius value of 4 and a working radius of 4. As shown in FIG. 20B, the individual transitions into area B, here as contingent downgrade is allowed, the individual's hygiene radius remains at a value of 4 for a particular time. Additionally, it is noted that the individual's working radius is at a level 2, as he is in area B. FIG. 20C shows the situation wherein an object is moved from the area C into area B. Here, it may be the case then that the individual comes in contact with the object from area C but not in contact with any object in area B in which he is presently located. Here, he may then encounter a downgrade in his hygiene radius value to a value of 3 while in a zone having a hygiene level of 2. Accordingly, he may then be able to enter zone C from area B without encountering a hygiene radius violation while not being able to reenter the area D without encountering a hygiene radius violation. FIG. 20D illustrates the radius violation that occurs upon entry into area D. This situation is shown to illustrate the point that objects may be moved into zones having lower level hygiene levels and thereby not cause a contamination but may lead to the downgrading of an individual's hygiene radius who has a higher level radius and is required by the lower hygiene level area in which he is located.

As can be appreciated from the discussion herein, a hygiene radius violation can lead to a protocol violation. Specifically, this may be the case if the individual is required to remedy his hygiene radius violation by undergoing or performing a hygiene related action and the individual does not comply with that requirement. Here, a protocol violation may result from the hygiene radius violation. This in turn may lead to a zone contamination. Specifically, an individual with a lower than required hygiene level is located in a higher-level hygiene zone. As a result, a zone contamination may occur. As a result of the zone contamination, individuals within the contaminated zone may then have their hygiene radius values downgraded. Then, as their working radius values remain the same, a hygiene radius violation is encountered. If the individuals having downgraded hygiene radius values enter or leave the zone in which they are located, they may or may not enter into a hygiene zone that would result in a further violation of the hygiene protocol.

Figure 21A:
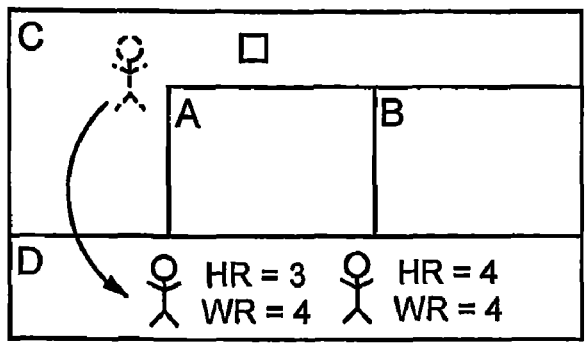
FIGS. 21A-21D are additional schematic illustrations of the invention shown in FIG. 9.
Figure 21B:
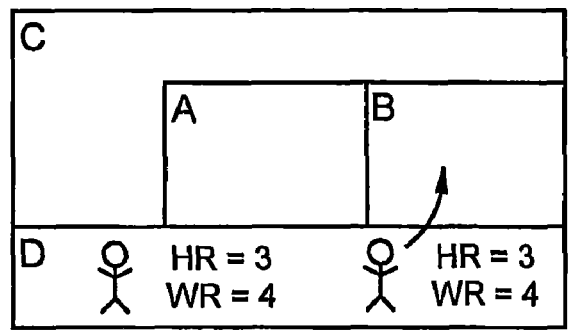
Figure 21C:
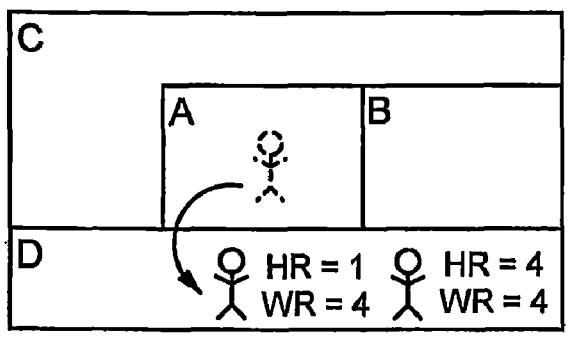
Figure 21D:
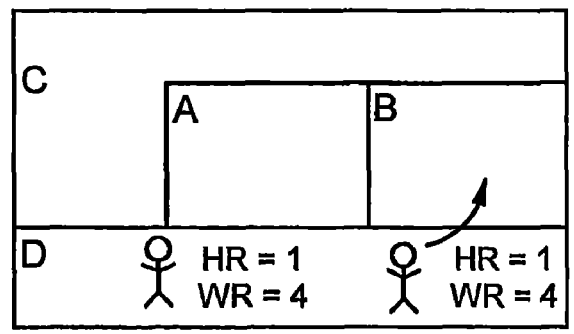

This situation is depicted in FIGS. 21A-21D. As shown in FIG. 21A, an individual transitions from area C into area D. As a result, a zone contamination occurs. As a result of the zone contamination, individuals within the zone have their hygiene radius values downgraded to 3. A similar but yet quite different situation is illustrated in FIG. 21C. In FIG. 21C, an individual transitions from the area A into area D. Here, a more severe contamination occurs whereby individuals within the contaminated area have their hygiene radius values decreased to level 1. In the former situation, wherein individuals have a hygiene radius value of 3, these individuals may transition into area C without negative consequences with respect to the hygiene protocol (FIG. 21B). Specifically, they are entering into a level 2 area while having a hygiene level of 3. In contrast, the latter situation, wherein the individuals have a hygiene level of 1, these individuals may not transition into area B without negatively impacting the facility's hygiene protocol (FIG. 21D). Specifically, as their hygiene radius values are at 1, entering into a hygiene area of level 2 will result in a further hygiene radius violation. In turn, this may lead to yet another hygiene protocol violation and additionally yet another zone contamination.

As can be appreciated, this situation illustrated in FIG. 21D may multiply to the point where a catastrophic facility wide protocol violation occurs. In accordance with embodiments of the present invention, an individual's ID tag or other device displays his or her hygiene radius. In this way, the individual may use this knowledge of his hygiene radius in determining whether or not his crossing a boundary between hygiene zone will lead to further contamination.

A number of events as described herein may result in an individual's hygiene radius being downgraded. One such event is illustrated in FIG. 11C. This particular event includes the crossing of a boundary between areas within the facility by the individual whose hygiene radius is downgraded as a result of the boundary crossing. Another such situation is illustrated in FIG. 16B. This particular event involves a zone contamination that results from an individual having a lower than required hygiene level crossing a boundary between hygiene zones and thereby causing others to have their hygiene radii downgraded. Additionally, non-zone factors may lead to the downgrade of a hygiene radius. For instance, a facility may require a thorough hand washing at particular time periods throughout the day. If an individual fails to comply with this hand-washing requirement, his or her hygiene radius may be downgraded. Moreover, it should be appreciated that one or more aspects of the present invention, such as, the mechanical lockout of work stations, the requirement for hand washing, and the giving of hand washing advice may be done without reference to the hygiene radius and the working radius values as described herein.

The above explanations of the present invention are given in the context of facility that has a range of different hygiene levels. As described above, the different hygiene levels may be maintained using various automated cleaning stations. Automated cleaning stations operate to dispense one or more fluids, such as water, a cleaning fluid, such as soap, and/or a disinfectant, etc., while a person's hands are placed in a washbasin. As used herein, a "washbasin" or "wash chamber" means a structure associated with the cleaning station where an appendage, such as a hand (or foot/boot) are cleaned, such as one or more wash cylinders, spray areas, pans, tubs, etc. Individuals, such as employees of a laboratory, food service related industry, or health care facility, may be instructed to wash their hands for a minimum amount of time that has been determined to be sufficient to provide a complete cleaning. In situations where hand (or boot) washing is required, or because of personal preferences, the user may be required to use (or otherwise desire to use) an automated cleaning station that incorporates a wash cylinder.

Figure 22:
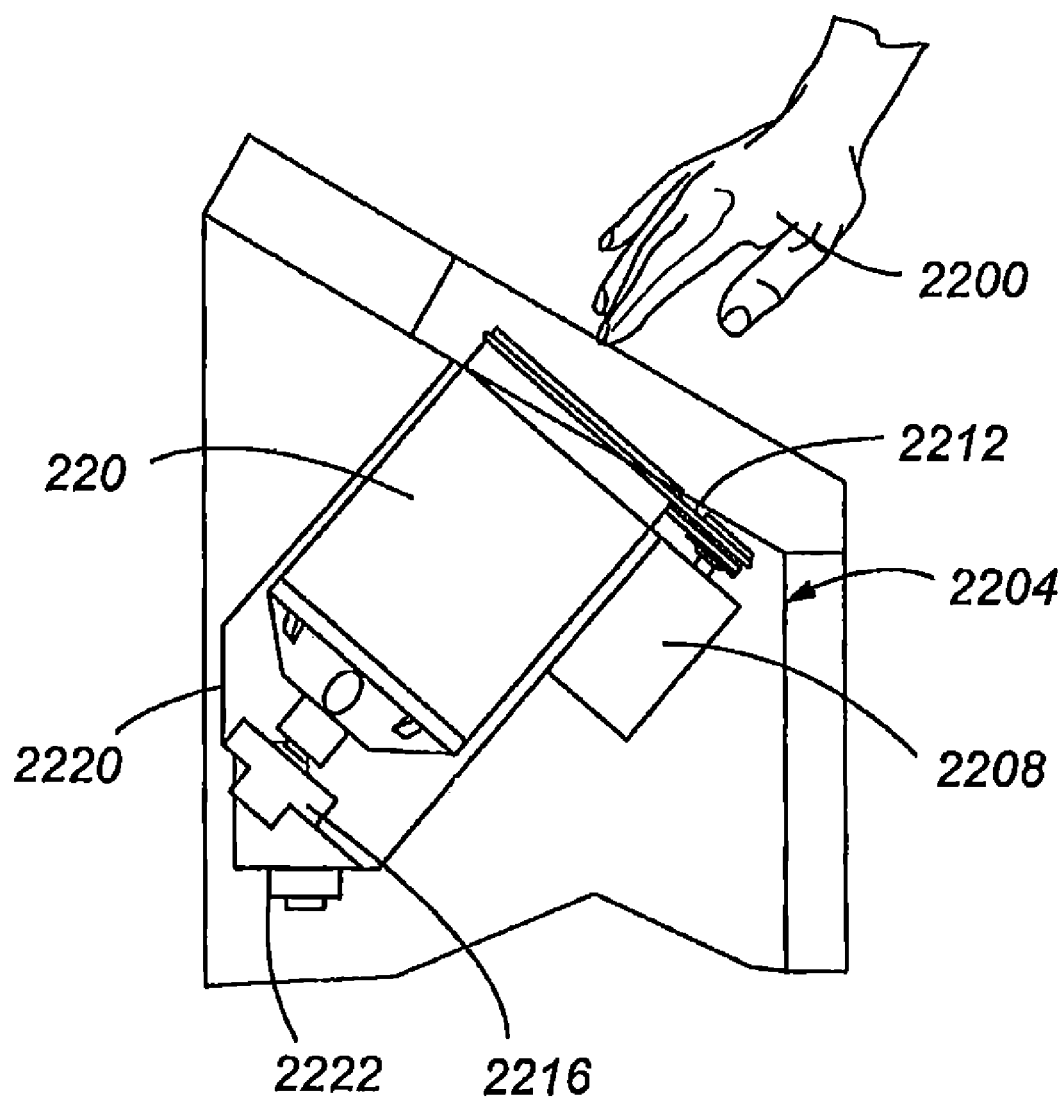
FIG. 22 is a close up of the device shown in FIG. 2.

Referring now to FIG. 22, a close-up view of the exemplary automated cleaning station 100a is depicted. FIG. 22 provides a view of part of the exemplary automated cleaning station 100a used by an employee whose hand 2200 is being placed in position to be washed. One wash basin 220 and other components associated with the cleaning station 100a can be seen in FIG. 22. The wash basin 220 may be associated with a drive assembly 2204 including a drive mechanism 2208 and a drive belt 2212. The drive assembly 2204 operates to rotate the wash basin 220 when the automated cleaning station 100a is in use. As the wash basin 220 rotates, a plurality of nozzles (not shown) disposed on the interior of the wash basin 220 spray water and/or cleaning fluid onto the hand 2200. The wash basin 220 is interconnected to a seating assembly 2216 that provides the wash basin 220 with a mounting within a receiving basin 2220. The receiving basin 2220 receives spent water and/or cleaning fluid that drains out of the wash basin 220 after use in connection with washing or rinsing the hand 2200. The spent fluid then exits through the basin drain 2222 towards the sewer or other disposal system.

FIG. 22 depicts one type of hygiene station that may be used in connection with embodiments of the present invention. In addition, the present invention may employ other varieties of automated hygiene stations that allow individuals to attain a variety of hygiene levels. (The various hand-hygiene stations described below may or may not be used in combination with the location tracking scheme set forth above.) For example, in a facility that defines only two hygiene levels, a hand-sink or an automated hand-washing station may be sufficient to meet a facility's needs. The following sets forth additional cleaning stations that may be used.

Figures 23, 24, 25:
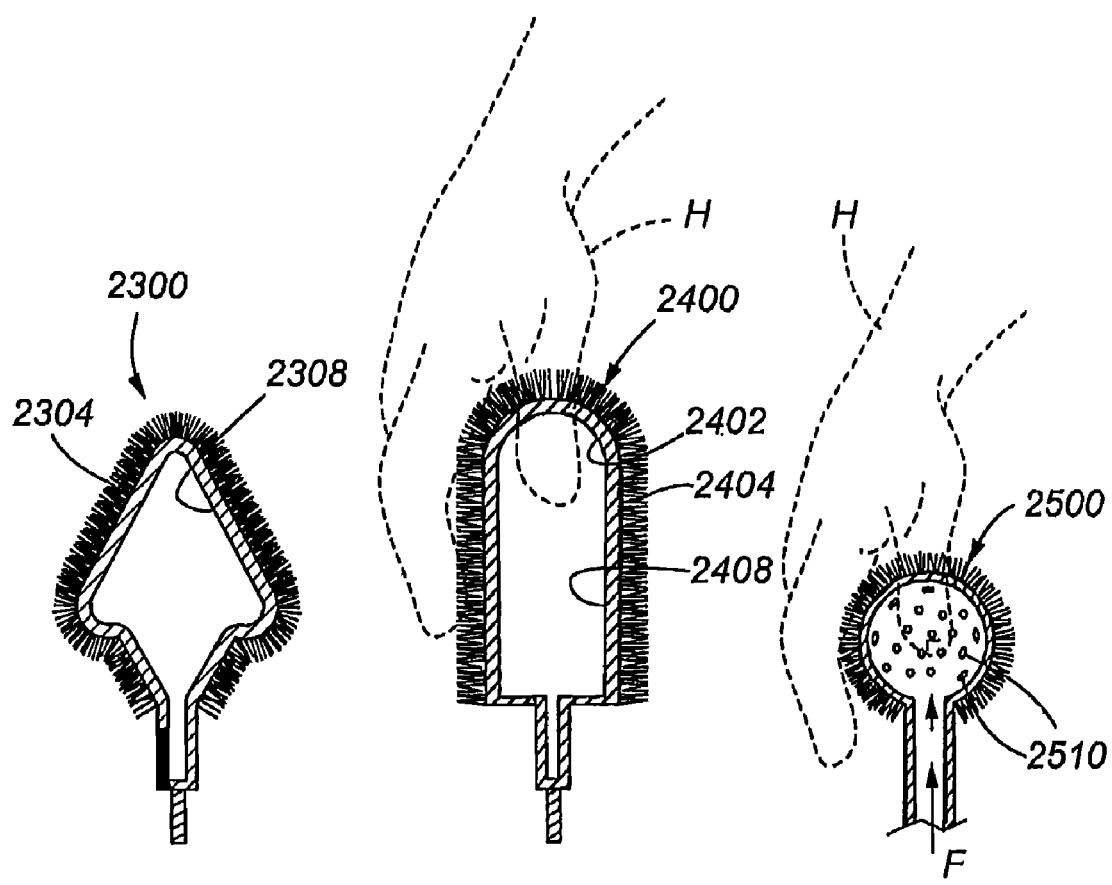
FIG. 23 is an end brush in accordance with embodiments of the present invention.
FIG. 24 is an alternative end brush in accordance with embodiments of the present invention.
FIG. 25 is yet another alternative end brush in accordance with embodiments of the present invention.

Embodiments of the present invention include of a hygiene station that includes a "scrub cylinder" having a brush disposed at the end of the wash basin or cylinder 220. Referring now to FIGS. 23-25, and in accordance with embodiments of the present invention, a series of various end brushes are illustrated for use with cleaning station 108. The end brushes are generally configured to include a distal end for facilitating interconnection to the interior distal end of the cylinder 220, such as by a threaded connection. The threaded connection or structure adjacent the threaded connection may include a sealing device such as an o-ring for preventing or limiting water and/or cleaning fluids from passing through the interconnection opening.

Referring now to FIG. 23, a conical-shaped brush 2300 is shown. Conical-shaped brush 2300 is configured for placement within the distal end of the cylinder 220. Conical-shaped brush 2300 features bristles 2304 that are located on the exterior of the conical body 2308. The conical-shaped brush 2300 is suited for allowing a user to contact his or her fingers, fingertips, finger nails, and/or palms with bristles 2304.

Referring now to FIG. 24, a cylindrical-shaped brush 2400 is shown, wherein the cylindrical-shaped brush 2400 is also configured for placement within the distal end of the cylinder 220. The cylindrical-shaped brush 2400 includes a semispherical portion 2402 at is first end, and a way (e.g., a threaded post, reverse threaded post, etc.) of interconnecting the brush to the cylinder 220 at its second end. Cylindrical-shaped brush 2400 also features bristles 2404 that are located on the exterior of the cylindrical body 2408. The cylindrical-shaped brush 2400 is suited for allowing a user to contact his or her fingers, fingertips, finger nails, and/or palms with bristles 2404.

Referring now to FIG. 25, a spherical-shaped brush 2500 is shown, wherein the spherical-shaped brush 2500 is also configured for placement within the distal end of the cylinder 220. The spherical-shaped brush 2500 includes features similar as those described above for the conical-shaped brush 2300 and the cylindrical-shaped brush 2400. In addition, the spherical-shaped brush 2500 includes openings 2510, where the openings 2510 may comprise orifices or nozzles for projecting a flow F of cleaning fluid to the hand H of the user 204 during a cleaning cycle, and/or for releasing disinfectant to sanitize the brush itself. Although not shown, the conical-shaped brush 2300 and the cylindrical-shaped brush 2400 may also include openings 2510, where the openings 2510 may comprise orifices or nozzles for projecting a flow F of cleaning fluid to the hand H of the user 204 during a cleaning cycle, and/or for releasing disinfectant to sanitize the brush itself.

Figure 26:
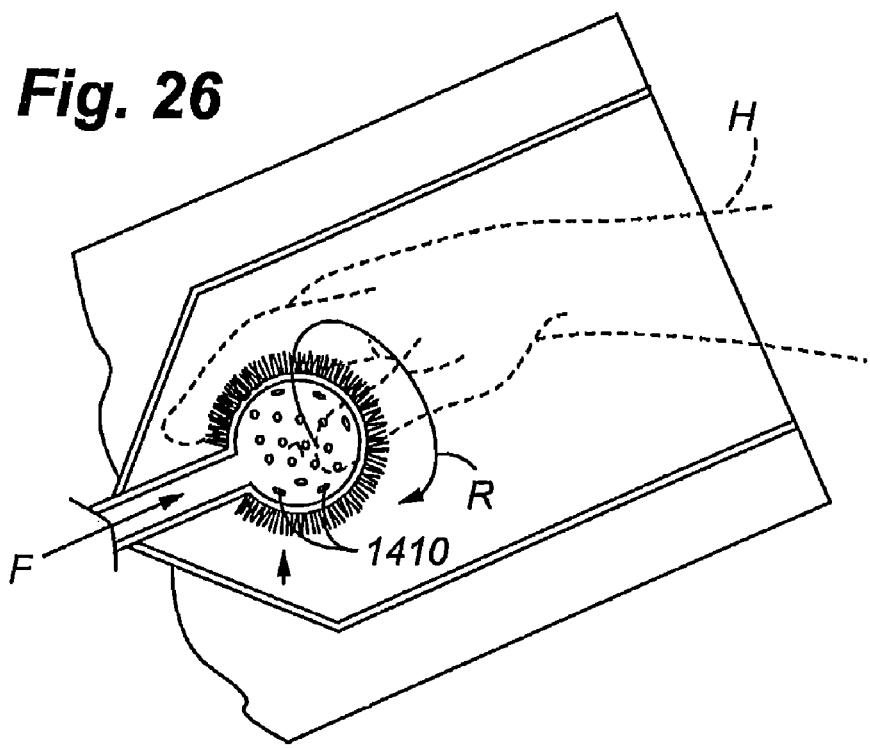
FIG. 26 is a scrub cylinder in accordance with embodiments of the present invention.

In accordance with at least one embodiment of the present invention, FIG. 26 is a depiction of a cylinder with a spherical-shaped brush 2500 attached to the bottom of the cylinder 2000, wherein the brush 2500 includes flow-through disinfectant nozzles or openings 2510 that will constantly clean the brush.

Figure 27:
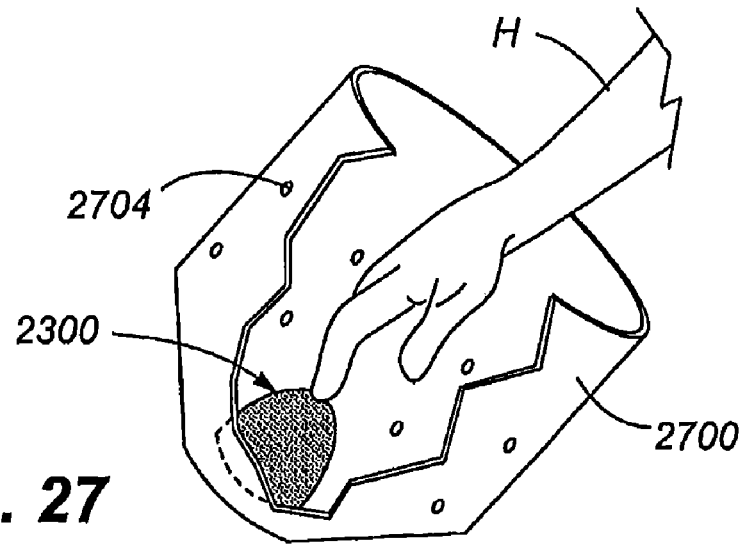
FIG. 27 is an alternative scrub cylinder in accordance with embodiments of the present invention.

FIG. 26 and FIG. 27 depict how various versions of how a debris removal cylinder may be used to clean the fingers and fingertips with the components that may be included in embodiments of the present invention. In use, the user inserts their hand H into the cylinder 220 and the cleaning station 100a automatically initiates a cleaning cycle by reading the presence of the user's hand H within the cylinder 220, such as by an optical sensor 216 shown in FIG. 2. Referring now to FIG. 27, rotating cylinder 2700 is shown with conical-shaped brush 2300. As shown in FIG. 27, the user may advance their hand H to contact the conical-shaped brush 2300. Nozzles 2704 dispense cleaning fluids to the hand during the cleaning cycle.

Figure 28A:
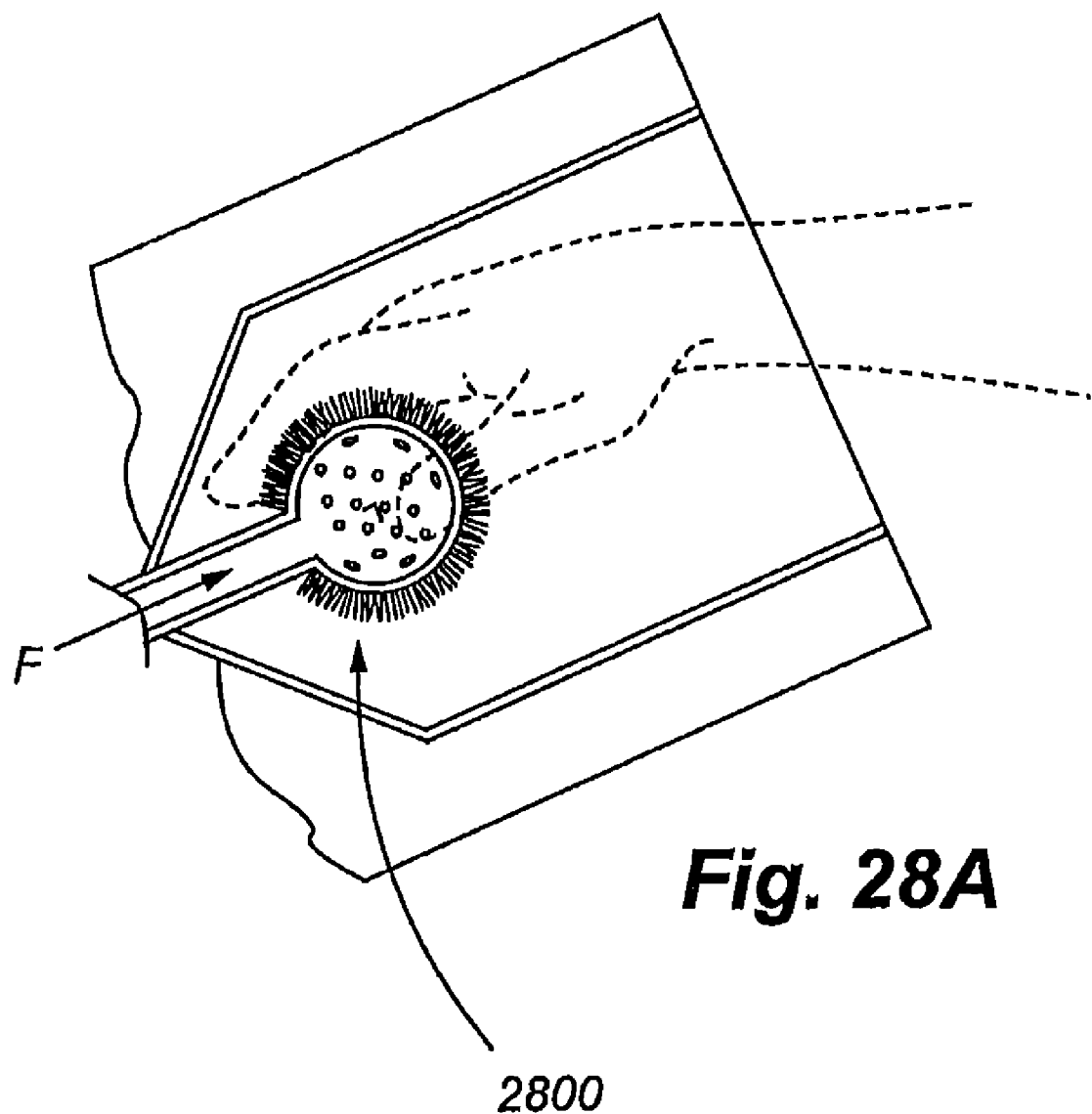
FIGS. 28A-28C show cylinders of different sizes in accordance with embodiments of the present invention.
Figure 28B:
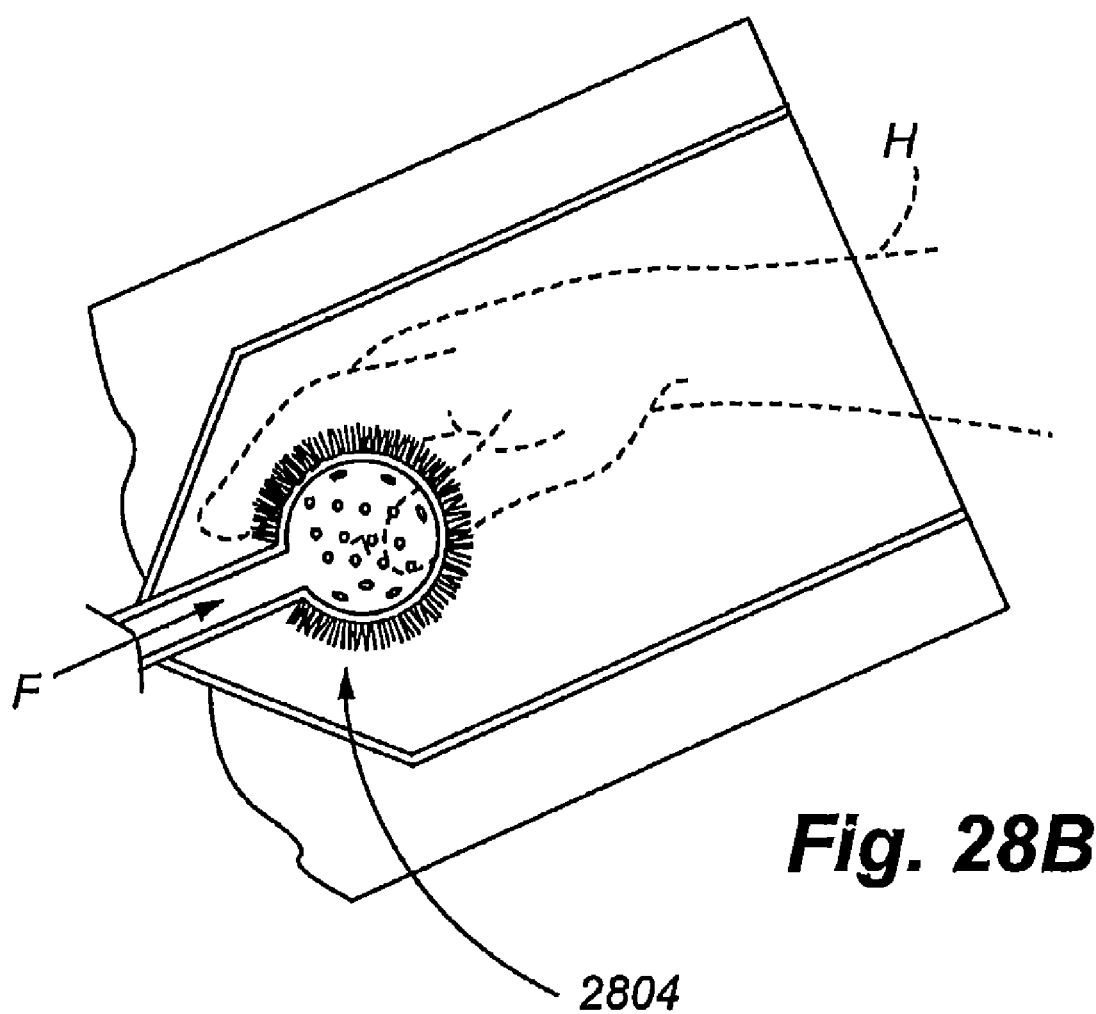
Figure 28C:
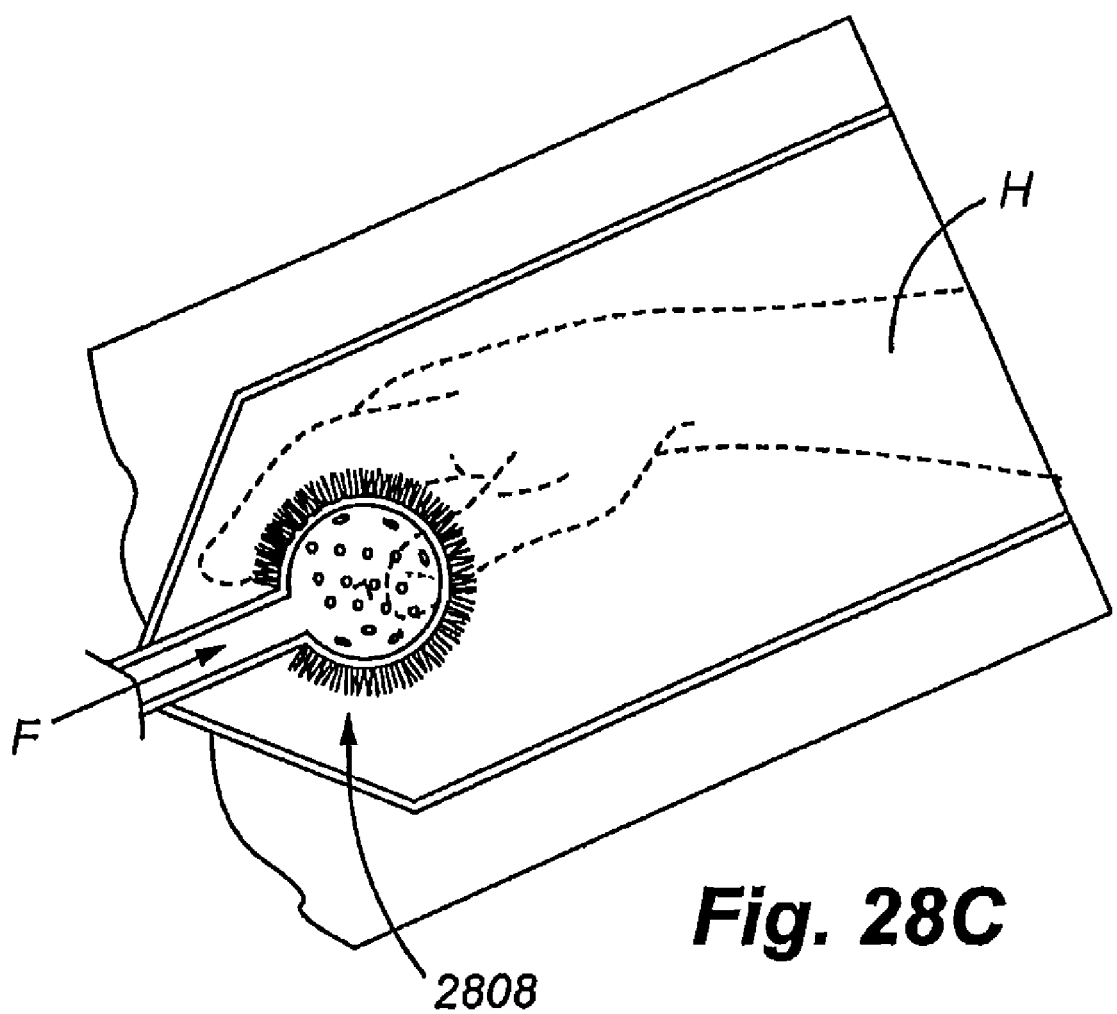

Embodiments of the present invention include of a hygiene station that includes am enlarged or variable length cylinder. FIGS. 28A-C show wash cylinders of various length. FIG. 28A shows a cylinder 2800 of shorter length. FIG. 28A shows a cylinder 2804 of medium length. FIG. 28A shows a cylinder of longer length 2808. This automated cleaning station includes a cylinder that is long enough to deliver cleaning fluid to the hands, wrists, forearms and upper arms of person. The enlarged cylinder may be deep enough to accommodate a person having arms of above-average length. The cylinders shown in FIGS. 28A-C include distal end brushes. It should be understood, however, that cylinders of variable length may be used that do not include distal end brushes.

Embodiments of the present invention include of a hygiene station that includes an adjustable cycle automated cleaning station. An adjustable cycle cleaning station is shown in FIG. 29. The adjustable cycle automated cleaning station 2900 includes a range of cleaning cycles that provide a variety of different cleaning levels. The adjustable cycle automated cleaning station includes control panel 2904, which can be used to apply different cleaning cycles may having different HSG or soap concentrations, different cycle durations, etc. By allowing a user to define different cycle parameters, a range of cleaning cycles can be achieved. Additionally, a variety of different spray patterns may be used. For example, the adjustable cycle automated cleaning station 2900 may be operable to produce a pulsed spray pattern. Here, one or more pumps 2908 may be used to achieve a pulsed spray pattern. Additionally, the automated cleaning station may employ a drying cycle to provide a more thorough hygiene cycle. Here, the hands remain in the cylinder and air is forced through the cylinders and onto the hands.

The automated cleaning station shown in FIG. 29 also includes an optional third cylinder in the form of fingertip cleaning cylinder 2912. As shown in FIG. 30, fingertip cleaning cylinder 2912 preferably comprises a cylinder with a brush element located at its distal end for cleaning the fingertips of the user. The fingertip cleaning cylinder 2912 preferably rotates and spins circular end brush 3004. Circular end brush 3004 is preferably detachably attached using a quick change fitting, such as a threaded coupling or other mechanism, and may include disinfecting nozzles of its own as described above. In accordance with at least one embodiment, a plurality of nozzles 3008 within the cylinder wall 3012 direct fluids toward the fingers and fingertips of the user. A cleaning station may include one or more dedicated debris removal cylinders, and/or it may comprise cylinders with friction enhancing structures such as brushes for removal of particulates, substances and biological matter.

Embodiments of the present invention include of a hygiene station that includes a "surgical scrub automated cleaning station." A surgical scrub cleaning station may include a combination of the above-described hygiene stations. Specifically, the surgical scrub cylinder may be an enlarged cylinder and may include a nail brush at the bottom of the cylinder. Additionally, a removable nail pick may be associated with the cleaning station. The surgical scrub cylinder automated cleaning station is operable to accommodate any variety of arm length. Here, a person must be allowed to reach the nail brush at the bottom of the cylinder, while at same time having his or her arm sufficiently deep in the cylinder to provide coverage of the upper arms. As can be appreciated, a relatively shorter cylinder length would allow any arm length to reach the nail brush, but not provide upper arm coverage for a longer arm. Similarly, a relatively longer cylinder would provide any arm length with upper arm coverage, but not allow a relatively shorter arm to reach the nail brush at the bottom of the cylinder.

Figure 31:
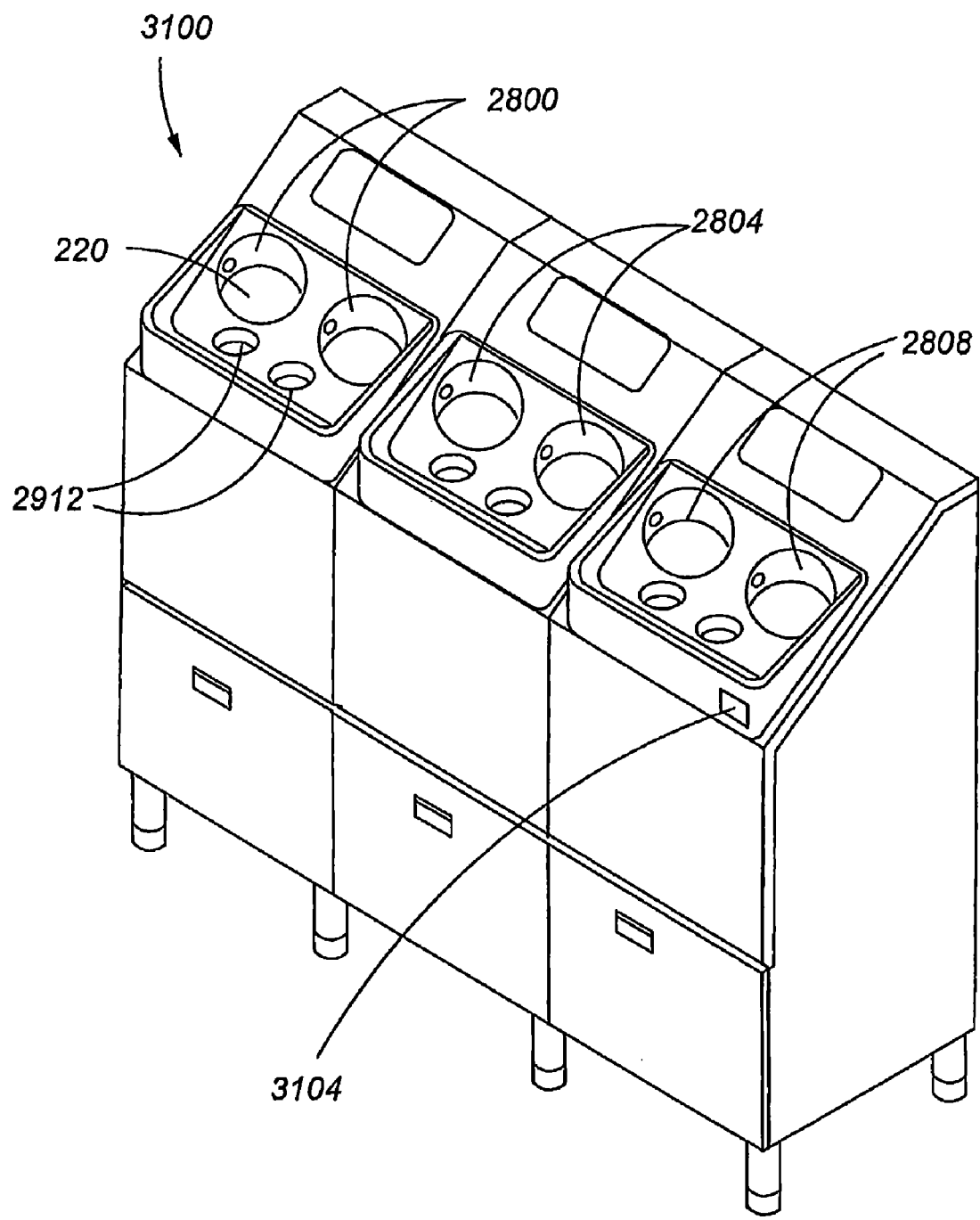
FIG. 31 shows a surgical scrub automatic cleaning station in accordance with embodiments of the present invention.

Accordingly, the surgical scrub cylinder may employ one of a number of designs that accommodate a variety of arm lengths. In one embodiment, a surgical scrub automated cleaning station 3100 includes multiple cylinders of different length, as shown in FIG. 31. The surgical scrub automated cleaning station shown in FIG. 31 includes two small shorter length cylinders 2800, such as the one shown in FIG. 28A; two medium length cylinders 2804, such as the one shown in FIG. 28B; and two larger cylinders 2808, such as the one shown in FIG. 28C. The three sets of cylinders are disposed next to each other and are each accessible at any given time. Additionally, the surgical scrub automated cleaning station includes a replaceable nail pick 3104.

Figure 60:
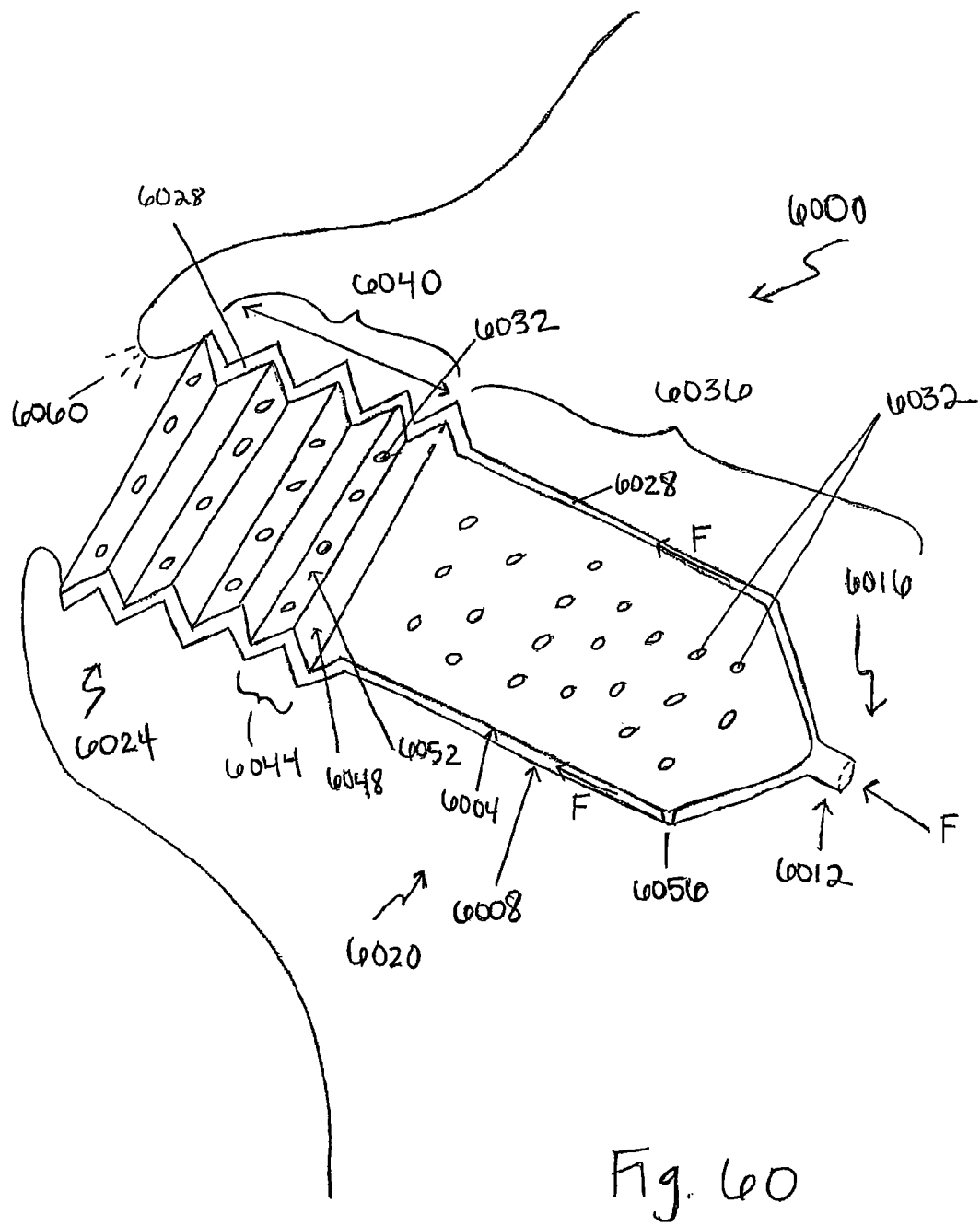
FIG. 60 shows a wash chamber for use in a surgical environment in accordance with embodiments of the present invention.

Referring specifically now to FIG. 60, another alternative embodiment of the surgical scrub automated cleaning station having adjustable depth/length is shown. More specifically, the surgical scrub automated cleaning station includes a rotatable, extendible, and retractable accordion cylinder 6000 to accommodate a variety of arm lengths. The accordion surgical scrub cylinder 6000 may be integrated into to the above described hygiene stations. The accordion cylinder 6000 may include an inner accordion wall 6004 and an outer accordion wall 6008. In the embodiment shown, water or other cleansing composition, such as chlorhexidine gluconate, is directed into the accordion cylinder 6000 via a fluid inlet 6012. The fluid inlet 6012 may be positioned near an inner portion 6016 of the accordion cylinder 6000. One skilled in the art will appreciate that the fluid inlet may be positioned at any point along the length of the accordion cylinder 6000. For example, the fluid inlet may be positioned at a middle portion 6020 or outer portion 6024 of the accordion cylinder 6000.

Once the fluid has passed through the fluid inlet 6012, the fluid F travels through the annular cavity 6028 positioned between the inner accordion wall 6004 and the outer accordion wall 6008. The inner accordion wall 6004 may also include a plurality of nozzles 6032. The nozzles 6032 may be positioned along both a cylindrical section 6036 and accordion section 6040 of the accordion cylinder 6000. The nozzles 6032 may include various types of nozzles, such as straight, angled, or canted nozzles, etc. in order to maximize cleansing and reduce splash-back. One of skill in the art will appreciate that the nozzles 6032 may also be configured in many different nozzle patterns, such as a linear array or helical configuration depending on the desired flow pattern. The outer accordion wall 6008 retains the fluid and maintains the necessary fluid pressure inside the cylinder to compensate for centrifugal forces and to ensure that the fluid is ejected out of the nozzles 6032 at a desired velocity.

The accordion section 6040 may be interconnected to the housing or other portion of the surgical scrub cleaning station. The accordion section 6040 of the accordion cylinder 6000 may also be made of a variety of materials that are capable of repeated compressing and expanding, such as a natural or synthetic rubber or other elastomer. The accordion section 6040 is flexible and foldable. That is, the accordion section 6040 is capable of compressing and expanding depending on the depth/length of the accordion chamber 6000 necessary to accommodate a particular arm length. In one embodiment, the accordion section 6040 is adapted to expand so that a user may insert and wash up to substantially his or her elbows. In a preferred embodiment, the accordion section 6040 is capable of allowing the accordion cylinder 6000 to expand and travel up to about 3-12 inches so that a user may wash his or her hands (including the digital, inter-digital, and webbed areas), forearms, and up to substantially the elbows.

The accordion section 6040 may be configured such that each fold 6044 of the accordion section 6040 has two adjacent faces, a first face 6048 and a second face 6052. In a preferred embodiment, the first face 6048 of a fold 6044 does not include any nozzles and the second face 6052 of a fold 6044 includes a plurality of nozzles 6032. In a more preferred embodiment, when the accordion portion 6024 is compressed the second face 6052 is folded against the first face 6048 such that the nozzles 6032 on the second face 6052 are obstructed/prohibited from ejecting fluid into the surgical scrub cylinder. However, when the accordion portion 6024 is expanded, the plurality of nozzles 6032 on the second face 6052 are exposed and allowed to eject fluid into the surgical scrub cylinder. One skilled in the art will appreciate that any number of devices/mechanisms may be used to ensure that fluids do not exit from nozzles 6032 on the accordion section 6040 when the accordion section 6040 is compressed. One skilled in the art will also appreciate that any number of devices/mechanisms may be used to ensure that fluids are permitted to flow out of the nozzles 6032 on the accordion section 6040 when the accordion section 6040 is expanded.

As the fluid travels along the length of the accordion cylinder 6000 through the annular cavity 6028, fluid may be ejected into the accordion cylinder 6000 through the plurality of nozzles 6032 interconnected to the inner accordion wall 6004.

In one embodiment, the fluid drains out of the accordion cylinder 6000 via an outlet 6056. In one embodiment, the outlet 6056 is positioned near the inner portion 6016 of the accordion cylinder. In a preferred embodiment, the outlet 6056 is positioned such that the fluid exiting the cylinder exits in a substantially vertical direction. That is, in a preferred embodiment, the fluid exiting the accordion chamber 6000 exits approximately orthogonal or perpendicular to a horizontal plane. One skilled in the art will appreciate that the outlet 6056 may be configured in a variety of ways, for example as a drain hole, a slot, or a valve, The outlet 6056 may also interconnect to the cleaning station via piping, tubing, hosing, or other means designed for the fluid conveyance in order to transport the fluid from the accordion cylinder 6000 to an outlet or other fluid exit. The outlet drain may be positioned in a variety of other positions, including those depicted in preceding embodiments.

The surgical scrub automated cleaning station may also include a light 6060 near the outer portion 6024 of the accordion cylinder 6000. The light 6060 illuminates the entrance of the accordion cylinder. Therefore, the accordion cylinder 6000 is visually inviting and unintimidating. In addition, the surgical scrub automated cleaning station may also include an interior light (not shown) that illuminates the interior of the accordion cylinder. By illuminating the interior portion of the accordion cylinder 6000, a user may visually inspect the interior of the wash chamber before and/or during a wash cycle and his or her hands and lower arms during cleaning to confirm debris removal.

The surgical scrub automated cleaning station may also include brushes (not shown) having with RFID technology such that a RFID reader may recognize the brush and limit the number of washings for the brush (e.g., only allow the brush to be used once), thereby insuring that a sterile brush is used with every surgical scrub wash cycle.

Figure 61:
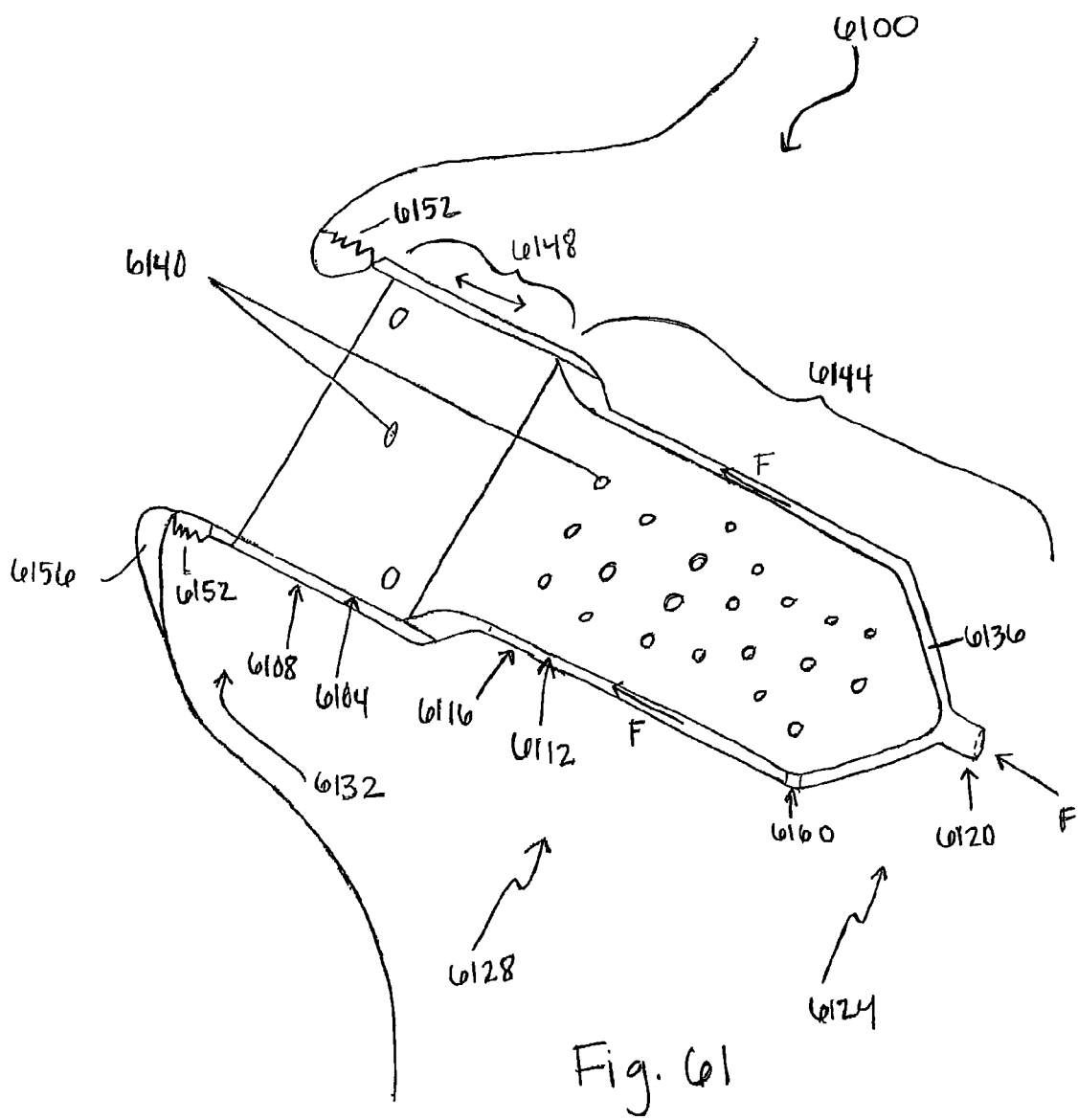
FIG. 61 shows another embodiment of a wash chamber for use in a surgical environment.

Referring specifically now to FIG. 61, yet another alternative embodiment of the surgical scrub automated cleaning station having adjustable depth/length is shown. More specifically, the surgical scrub automated cleaning station includes a telescopic cylinder 6100 that may accommodate a variety of arm lengths. The telescopic surgical scrub cylinder 6100 may be integrated into to the above described hygiene stations. The telescopic cylinder 6100 may include an inner telescoping wall 6104 and an outer telescoping wall 6108 interconnected to an inner cylindrical wall 6112 and an outer cylindrical wall 6116. In the embodiment shown, water or other cleansing composition, such as chlorhexidine gluconate, is directed into the telescoping cylinder 6100 via a fluid inlet 6120. The fluid inlet 6120 may be positioned near an inner portion 6124 of the telescopic cylinder 6100. However, one of skill in the art will appreciate that the fluid inlet 6120 may be positioned at any point along the length of the telescopic cylinder 6100. For example, the fluid inlet may be positioned at a middle portion 6128 or outer portion 6132 of the telescopic cylinder 6100.

Once the fluid has passed through the fluid inlet 6120, the fluid F travels through the annular cavity 6136 positioned between inner cylindrical wall 6112 and the outer cylindrical wall 6116 and between the inner telescoping wall 6104 and the outer telescoping wall 6108. The inner cylindrical wall 6112 and the inner telescoping wall 6104 may also include a plurality of nozzles 6140. The nozzles 6140 may be positioned along both a cylindrical section 6144 and telescoping section 6148 of the telescopic cylinder 6100. The nozzles 6140 may include various types of nozzles, such as straight, angled, or canted nozzles, etc. in order to maximize cleansing and reduce splash-back. Moreover, one of skill in the art will appreciate that the nozzles 6140 may also be configured in many different nozzle patterns, such as a linear array or helical configuration depending on the desired flow pattern. The outer cylindrical wall 6116 and the outer telescoping wall 6108 retain the fluid and maintain the necessary fluid pressure inside the cylinder to compensate for centrifugal forces and to ensure that the fluid is ejected out of the nozzles 6140 at a desired velocity.

The telescoping section 6148 of the telescopic cylinder 6100 may be configured such that it is capable of repeated shortening and lengthening. That is, the telescoping section 6148 is capable of sliding out over the cylindrical section 6144 so that the length/depth of the telescopic cylinder 6100 is lengthened/elongated. Therefore, the telescoping cylinder 6100 is capable of having an adjustable length and accommodating different arm lengths. In one embodiment, the telescoping section 6148 is adapted to expand so surgeons having different arm lengths may insert their hands and forearms (up to their elbows) into the telescopic cylinder 6100 in order to wash and prepare for surgery. In a preferred embodiment, the telescoping section 6148 is capable of allowing the telescopic cylinder 6100 to lengthen approximately 6 inches. One skilled in the art will appreciate that any number of devices/mechanisms may be included to ensure that the cylindrical portion 6144 and the telescoping portion 6148 properly telescope and slide in and out of one another.

The telescoping section 6148 may be configured such that when the telescopic cylinder 6100 is in an unextended or shortened position the nozzles 6140 on the telescoping section 6148 are blocked by the cylindrical section 6144. Alternatively, the telescoping section 6148 may be configured such that when the telescopic cylinder 6100 is in the unextended/shortened position, the nozzles 6140 on the telescoping section 6148 align with the nozzles on the cylindrical section 6144 so that the nozzles 6140 on the telescoping section 6148 are not obstructed and fluid is ejected through the aligned nozzles and into the telescopic cylinder 6100.

Figure 63:
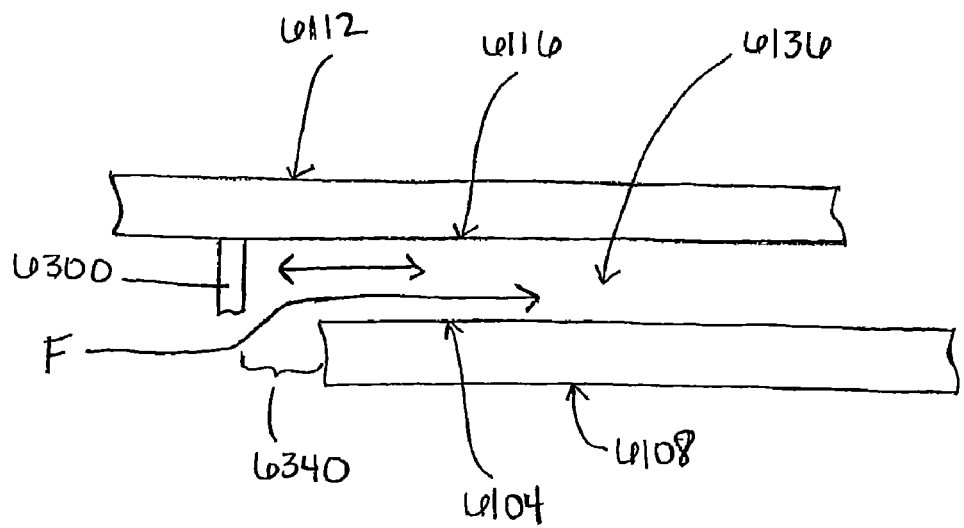
FIG. 63 shows the cross section of an annular channel of one embodiment of the telescopic wash cylinder for use in a surgical environment.
Figure 64:
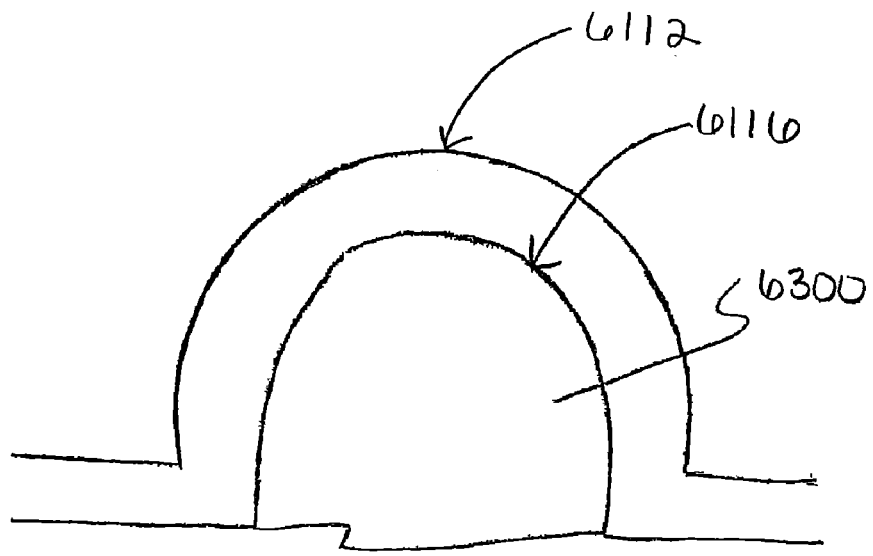
FIG. 64 shows an end view of the sealing member and channel.

A cross section of the annular cavity 6136 at the interface of the cylindrical portion 6144 and telescoping portion 6148 is shown in FIGS. 63 and 64. The configuration assumes that a number of mating discrete channels in both the telescoping and cylindrical portions 6148 and 6144 provide fluid to nozzles in both the telescoping and cylindrical portions. A sealing member 6300 may be moveably connected to the annular cavity 6136. The movable and translational sealing member 6300 is interconnected to either the cylindrical walls or the telescoping walls. The sealing member 6300 of a preferred embodiment is capable of forming a waterproof seal, such as using a gasket at the intersection of the member 6300 and wall 6112. Thus, when the telescoping cylinder 6100 telescopes (expands/compresses) the sealing member 6304 travels with a telescoping component such that the fluid is prevented from traveling to the untelescoped portion of the telescopic cylinder 6100. The fluid flow from a first channel in the cylindrical portion to a mating second channel in the telescoping portion is denoted by the letter "F" and directional arrow. During movement, the size or cross-sectional area of the opening 6340 between the sealing member 6300 and end of the surface 6108 increases or decreases with extension and retraction of the telescoping portion, respectively. In this manner, fluid flows from the cylindrical portion 6144 to the telescoping portion 6148 notwithstanding movement therebetween.

Referring back to FIG. 61, as the fluid "F" travels along the length of the telescopic cylinder 6100 through the annular cavity 6136, fluid may be ejected into the telescopic cylinder 6100 through the plurality of nozzles 6032 interconnected to the inner telescoping wall 6104 and inner cylindrical wall 6112.

In one embodiment, the fluid drains out of the telescopic cylinder 6100 via an outlet 6160. In one embodiment, the outlet 6160 is positioned near the inner portion 6120 of the telescopic cylinder. In a preferred embodiment, the outlet 6160 is positioned such that the fluid exiting the cylinder exits in a substantially vertical direction. Moreover, one skilled in the art will appreciate that the outlet 6160 may be configured as a drain hole, slot, valve, etc. The outlet 6160 may also interconnect to the cleaning station via piping, tubing, hosing, or other means designed for the fluid conveyance in order to transport the exiting fluid from the telescopic cylinder 6100 to an outlet or other fluid exit.

The telescoping section 6148 may be interconnected to the housing or other portion of the surgical scrub cleaning station. In a preferred embodiment, the telescoping section 6148 may be interconnected to an extendible and retractable rubber baffle 6152 interconnected to the housing of the surgical scrub cleaning station. The rubber baffle 6152 acts as a protective device for users. The rubber baffle 6152 serves as a barrier so that a user's hands and/or forearms do not contact the interface between the rotating telescoping cylinder and the stationary wash station. In one embodiment, the rubber baffle 6152 may also extend over some portion of the opening of the telescopic cylinder 6100 (not shown). In this embodiment, the rubble baffle 6152 acts as a splash guard and prevents fluid from escaping from the telescopic cylinder 6100 and expands or contracts in width in response to expansion and contraction of the telescopic portion 6148. Therefore, embodiments of the surgical scrub cylinders may include a rubber baffle 6152 to enhance user safety and prevent undesirable splash back.

Embodiments of the surgical scrub cleaning stations may also include a drip tray 6156. The drip tray 6156 is capable of containing any fluid escaping from a wash cylinder, such as the telescopic cylinder 6100. The drip tray prevents the floor from becoming wet and potentially unsafe. One of skill in the art will appreciate that ensuring the area surrounding a hygiene station remains dry is important in a surgical environment. For example, in a hospital surgery wing or emergency room, surgeons, doctors, nurses, and other hospital personnel likely need to prepare a patient for treatment quickly. As such, it is imperative that hospital personnel can quickly and readily comply with hygiene requirements (i.e. use a surgical scrub cleaning station) and move the patient to the appropriate area without slipping or falling on a wet surface. Fluid from the lower arm of a surgeon, for example, drains into the drip tray at the elbow of the surgeon (when the elbow is held above the drip tray 6156 and the arm is bent upwardly).

The telescopic cylinder 6100 may also include a series of brushes (not shown) that can be inserted and removed from the telescopic cylinder 6100 after use. The surgical scrub cleaning station may also utilize RFID technology that allows for specific user settings and further does not allow a specific brush to be used more than once.

Figure 62:
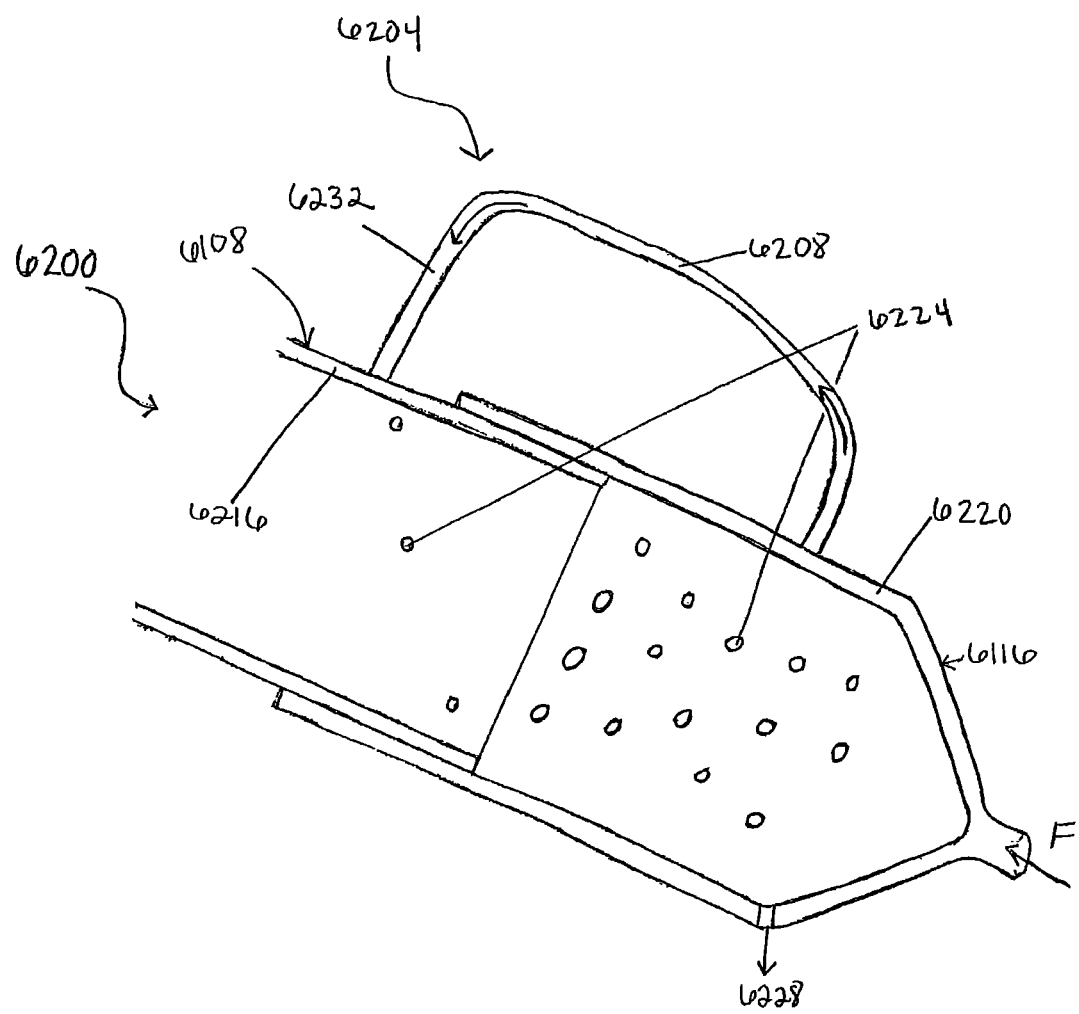
FIG. 62 shows another embodiment of a wash chamber for use in a surgical environment.

Referring now to FIG. 62, an alternative embodiment of the telescopic cylinder 6200 is shown. More specifically, the telescopic cylinder 6200 telescopes in the opposite configuration than that shown in FIG. 61. That is, the inner and outer cylindrical walls 6116 and 6112 telescope and slide over the inner and outer telescoping walls 6104 and 6108.

In addition, FIG. 62 shows an alternative fluid conveyance structure 6204. The fluid conveyance structure 6204 of a telescopic cylinder is shown in a daisy-chain configuration. The fluid conveyance structure 6204 of a preferred embodiment includes a fluid conveying conduit 6208. The fluid conveying conduit may include a hose, a tube, a pipe, or other suitable device for conveying fluid. The fluid conveyance structure of the daisy chain configuration includes at least one fluid conveyance conduit 6208 that is interconnected to a first set of fluid-conveying channels in the annulus defined by cylindrical wall 6116 and a second set of fluid conveying channels in the annulus defined by telescoping wall 6108. Both the first and second sets of channels provide pressurized fluid to the nozzles 6224. As such, the fluid is able to travel from the annular space 6220 (between the inner and outer cylindrical walls 6112 and 6116), into and through the inlet fluid conveyance channel 6208, and then exit into the annular space 6216 (between the inner and outer telescoping walls 6104 and 6108). Once in the annular spaces 6220 and 6216 the fluid F may be ejected through a plurality of nozzles 6224 into the telescopic cylinder 6200. Additional links of the daisy chain may be provided such that additional positions along the length of the telescopic cylinder are interconnected. The fluid F may exit the telescopic cylinder 6200 via an outlet 6228. The outlet 6228 is shown positioned at an inner portion of the telescoping cylinder 6200; however, one of skill in the art will appreciate that the outlet 6228 may be positioned at any point along the length of the telescoping cylinder that is capable of providing adequate drainage for the telescopic cylinder 6200.

In a still further embodiment of the present invention, the fluid conveyance structure may be configured as a nozzle inlay in which the nozzle inlay interconnects the inner cylindrical and telescoping walls to a plurality of nozzles. In addition to the fluid conveyance structures discussed above, one of skill in the art will appreciate that any suitable mechanism may be used to provide fluid to the nozzles.

With respect to any of the surgical scrub wash cylinders, the inner walls are preferably designed to rotate about a rotational axis so that when in use. In a preferred embodiment, the inner walls are capable of rotating 360 degrees about some rotational axis. The rotation of the inner walls of a surgical scrub wash cylinder provides enhanced cleaning to the hands and forearms.

In yet another alternative embodiment, the surgical scrub automated cleaning station includes a plurality of cylinders having different lengths that may be rotated into position. Here, a person selects a cylinder size and that cylinder is rotated into position such that it may be accessed through the top opening in the automated cleaning station. In this way, the surgical scrub automated cleaning station may accommodate any arm length.

One of skill in the art will also appreciate that embodiments of the surgical scrub wash cylinders may be oriented the opposite direction from that shown in FIGS. 31 and 60-62. That is, the user may reach upwards to insert his or her hands into the wash cylinder rather than downwards as shown. In the upward orientation, a fluid outlet or drain hole/slot may be provided at the outer portion of the wash cylinder (near the housing of the wash station). In this orientation, one skilled in the art will appreciate that a more robust splash-guard may be provided to further ensure that an unacceptable amount of fluid does not escape from the wash cylinder.

The surgical scrub cleaning stations may be made of stainless steel. Moreover, the surgical scrub cleaning stations may be self-standing or wall mounted. In a preferred embodiment, the surgical scrub wash cylinders are positioned at a predetermined angle for ease of ingress and egress and to ensure adequate drainage. The surgical scrub wash cylinders may be further positioned to minimize splash back. Depending on the hygiene requirements imposed for a surgical scrub, the surgical scrub cleaning stations may have single or multiple cycles of soap injection. The surgical scrub cleaning stations may also have system sterilization cycle after each cleaning cycle to ensure that the wash cylinder is sterile before each use. The surgical scrub cleaning station may also include visual confirmation of the wash cycle progress.

Embodiments of the surgical scrub wash cylinders of the present invention may also include brushes designed specifically to clean the subungual (or below the fingernail) portions of the hand. In a preferred embodiment, the brushes are designed to be attached and removed from the inner portion of the cylinders. In a more preferred embodiment, the brushes are disposable to ensure that sterile brushes are used during each wash and the brushes are equipped with an identification system, such as RFID technology, to ensure that sterile brushes are used for each use of the wash cylinder.

The fluid used in some embodiments of the surgical scrub wash stations is preset to a certain temperature and controlled electronically by the wash station. In addition, the surgical scrub wash stations may provide visual injection confirmation that the soap/disinfectant/cleansing composition has been injected into the cylinder. Similarly, the soap/sterile liquid may be interconnected to the surgical scrub wash stations via disposable, single use soap cartridges, thus ensuring the every user receives a sterile liquid/soap. However, in other embodiments, the soap/sterile liquid may be interconnected to the surgical scrub wash stations via bulk dispensing means, such as one gallon container.

Embodiments of the surgical scrub wash stations include RFID technology for compliance monitoring. For example, a surgical scrub wash station may include soap monitoring to ensure the correct soap is used and/or to signal that a soap replacement is needed. Similarly, a surgical scrub wash station may include brush monitoring to ensure that sterile brushes are used and/or to signal that a brush replacement is necessary.

Surgical scrub wash stations of the present invention may also include additional options such as, seismic mounting anchors, a redundant power source, and air curtain to minimize splash, an on-board water tank to ensure consistent temperature and water supply, or water pressure controlled by an auxiliary pump to ensure desired efficacy.

In one configuration, the positional setting of the telescoping portion relative to the cylindrical portion is set automatically in response to sensed user identifier, such as RFID. A processor in the cleaning station senses the user's identifier and positions or repositions automatically the telescoping portion to a length that accommodates the length of the user's lower arm. This can provide enhanced levels of user convenience and satisfaction compared to a (completely) manually positioned or positionable telescoping portion. In the automated configuration, the telescoping portion is positioned by a new user using automatic controls, the settings are saved and linked or related to the user's profile or identifier, and the position of the telescoping portion is thereafter automatically determined using the user's identifier.

In addition to providing upper arm coverage and a nail brush, the surgical scrub cylinder may employ additional features that provide enhanced or higher level hand washing. In particular, the surgical scrub cylinder may provide a drying cycle or a pulsed flow of cleaning fluid. Wash cycle parameters may be adjusted depending on the hygiene requirements. A self-cleaning cycle may be performed after each cylinder use. The nail brush or brush may be replaced after each use. In some cases, the automated cleaning station may be automatically shut-down pending a self-cleaning or brush replacement. Automatic shut-down of the cleaning station may be imposed after each use or after a predetermined number of uses.

It should be appreciated that the foregoing cleaning stations can be considered extensions or modifications to the basic cleaning station illustrated in FIG. 2. Accordingly, any of the above described cleaning stations may additionally include such components as RFID reader 212, for use in reading RFID tags 208; optical sensor 216; cleaning station operations monitor 200; and video display 224.

Figure 32:
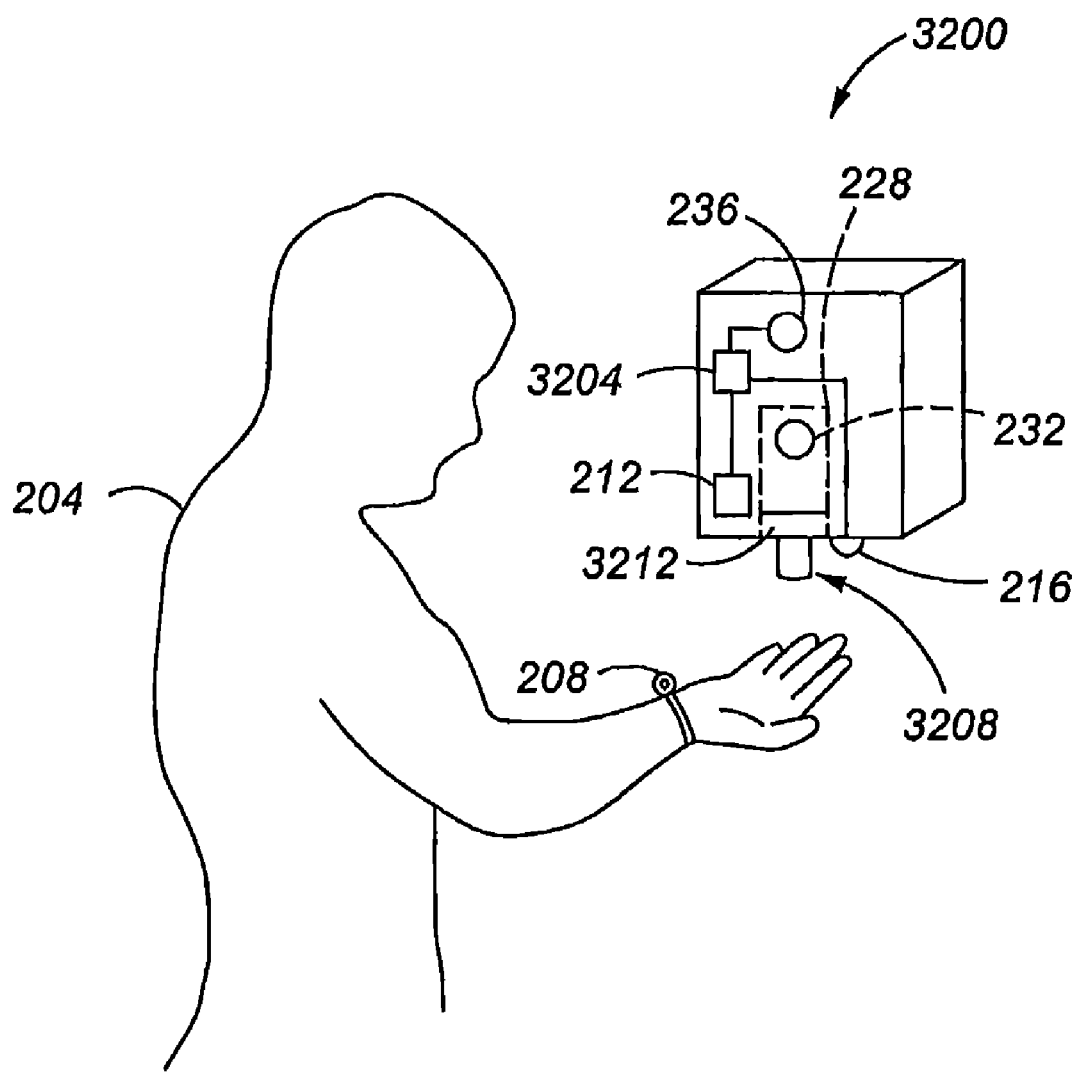
FIG. 32 shows a monitored hand sanitizer in accordance with embodiments of the present invention.

Referring now to FIG. 32, an exemplary sanitizer dispenser 3200 is illustrated. The sanitizer dispenser 3200a includes a sanitizer dispenser operations monitor 200. The sanitizer dispenser operations monitor 200 is a computational device such as a general purpose computer, controller, or ASIC that is operable to record data associated with employee use of the sanitizer dispenser 100a and to report the data to the administration computer 104. The sanitizer dispenser operations monitor 200 may be incorporated into the sanitizer dispenser 100a (if an automated dispenser) or, alternatively, may be implemented as a separate computing device.

Also shown in FIG. 32 is a user 204 of the sanitizer dispenser 100a. The user 204 may be an employee or visitor who is required to use a sanitizer because of the nature of their work or the nature of the facility. The user 204 is shown wearing a user RFID tag 208. The user RFID tag 208 is programmed by an RFID tag programming device (not shown) with information such as an employee number that, when read, uniquely identifies the employee. The RFID tag 208 may be incorporated into an identification badge or bracelet worn by the user 204.

In accordance with embodiments of the present invention, the sanitizer dispenser 100a includes an RFID reader 212. The RFID reader 212 is positioned so as to be able to read the user RFID tag 208 when the user 204 is obtaining sanitizer at a sanitizer dispenser 100a. The RFID reader 212 may be incorporated into the sanitizer dispenser 100a or, alternatively, may be implemented as a stand-alone device. For example, the RFID reader 212 may be positioned adjacent to the sanitizer dispenser 100a.

In a separate aspect of the present invention, the sanitizer dispenser 100a may optionally include a use verifier, such as an optical sensor 216 positioned so as to be able to sense whether the user 204 actually positioned at least one of their hands for properly receiving a dose of sanitizer. For example, a battery powered optical sensor 216 may be placed adjacent a plunger 218 that is depressed by the user 204 to obtain sanitizer from the sanitizer dispenser 100a. Alternatively, the optical sensor 216 may serve as both a use verifier and as a trigger for the sanitizer dispenser. For example, in touchless sanitizer dispensers the optical sensors 216 serve to trigger the sanitizer dispenser to deliver a dose of sanitizer by an electric pump or atomizer. For such sanitizer dispensers, the optical sensor 216 may also serve as the optical sensor for monitoring the position of the user's hands and reporting to the administration computer 104 whether, and optionally for how long, the person actually held their hand(s) to receive a dosage of sanitizer, and thus, that the person was not just located near the sanitizer dispenser 100a. Alternatively yet, other ways of monitoring whether the sanitizer dispenser 100a has been used are also within the scope of the invention. For example, as those skilled in the art will appreciate, the plunger 218 or other dispensing device associated with the sanitizer dispenser 100a may include a trip/cycle indicator (not shown) for registering whether the plunger 218 was actually depressed or otherwise triggered.

The RFID reader 212 and the optical sensor 216 (if present) are in communication with sanitizer dispenser operations monitor 200, which, in turn, is operable to collect data associated with these devices. More particularly, data is collected from the RFID reader 212 indicating the identity of the user 204. Additionally, if the sanitizer dispenser 100a includes a use verifier, such as an optical sensor 216, data from the use verifier is also collected by the sanitizer dispenser operations monitor 200. As those skilled in the art will appreciate, in addition to RFID, other magnetically, optically, and/or electronically readable user identifiers are within the scope of the present invention. In particular, a user may be identified by way of a typed password, retinal scan, voice print, palm print, fingerprint, face identification, bar coding (on an employee ID), etc.

Also shown in FIG. 32 is a consumables container 228 that contains the sanitizing material, such as an alcohol gel. In accordance with at least one embodiment of the present invention, the consumables container 228 may optionally include a detachable connection to a consumable receptacle 230 associated with the sanitizer dispenser 100a so that the consumable container 228 may be removed and disposed of when its contents are expended. After the disposal of a used consumables container 228, a new consumables container 228 is then attached to the sanitizer dispenser 100a. In accordance with one or more embodiments of the present invention, the consumables container 228 also includes a consumables RFID tag 232 that contains information related to the consumable container 228. A consumables RFID reader 236 associated with the sanitizer dispenser 100a reads the consumables RFID tag 232 and communicates information related to the consumables container 228 to the sanitizer dispenser operations monitor 200. In one embodiment of the present invention, the RFID reader 212 can also serve as the consumables RFID reader 236 so that two separate readers are not need. However, two separate readers could be used. In addition, although RFID is discussed herein for use of identification of consumables, as noted herein other types of identification systems may be used, such as bar codes. Thus, for example, if RFID is used to identify the user, and a bar code is used to identify the consumables, or vice-versa, two separate readers may be needed.

Figure 33:
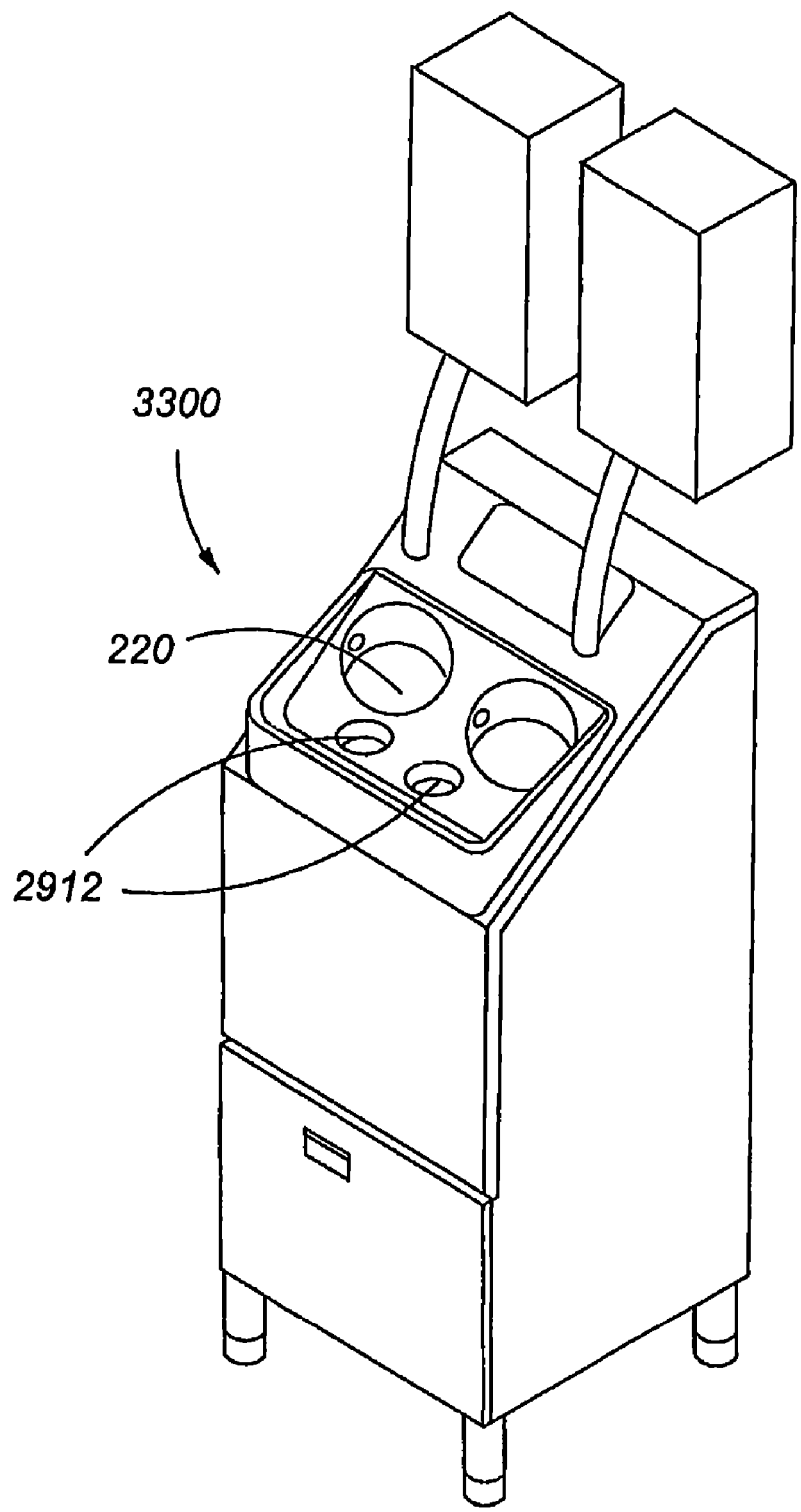
FIG. 33 shows a complete hand care station in accordance with embodiments of the present invention.

Another example of a higher-level hygiene station that may be used is the "complete hand care" automated cleaning station 3300, shown in FIG. 33. The complete hand care automated cleaning station includes at least three elements that provide a total hand care package. First, the complete hand care cleaning station includes an automated hand-washing cylinder 220. Second, the complete hand care cleaning station includes a monitored hand-sanitizer 3200. Third, the complete hand care cleaning station includes a monitored lotion dispenser 3300. Here, the automated hand-washing cylinder 220 may be used to provide an initial hand washing. The monitored hand sanitizer 3200 may then be used throughout the day in order to maintain hand hygiene. As hand sanitizers 3200 are typically alcohol based, the lotion dispenser 3300 is provided. Here, the lotion may be used to prevent damage to the skin, which may be caused by the use of the alcohol based hand sanitizer. Overuse of lotion, however, may be detrimental to hand hygiene. In particular, repeated use of lotion may result in the build up of a film on the surface of the hands. This film may in fact promote the growth of germs and/or microbes. In order to prevent this from occurring, the automated cleaning cylinder 200 may be used to thoroughly clean the hands, including washing away any film built-up due to lotion use. Here, the use of the automated cleaning station, the hand-sanitizer 3200 and the lotion dispenser may be monitored, and instructions and/or requirements may be issued regarding their use. In particular, an individual may be instructed or required to use the lotion dispenser after a predetermined number of uses of the hand sanitizer 3200. In addition, an individual may be instructed or required to use the automated cleaning cylinder after a predetermined number of uses of the lotion dispenser 3300.

Figure 34:
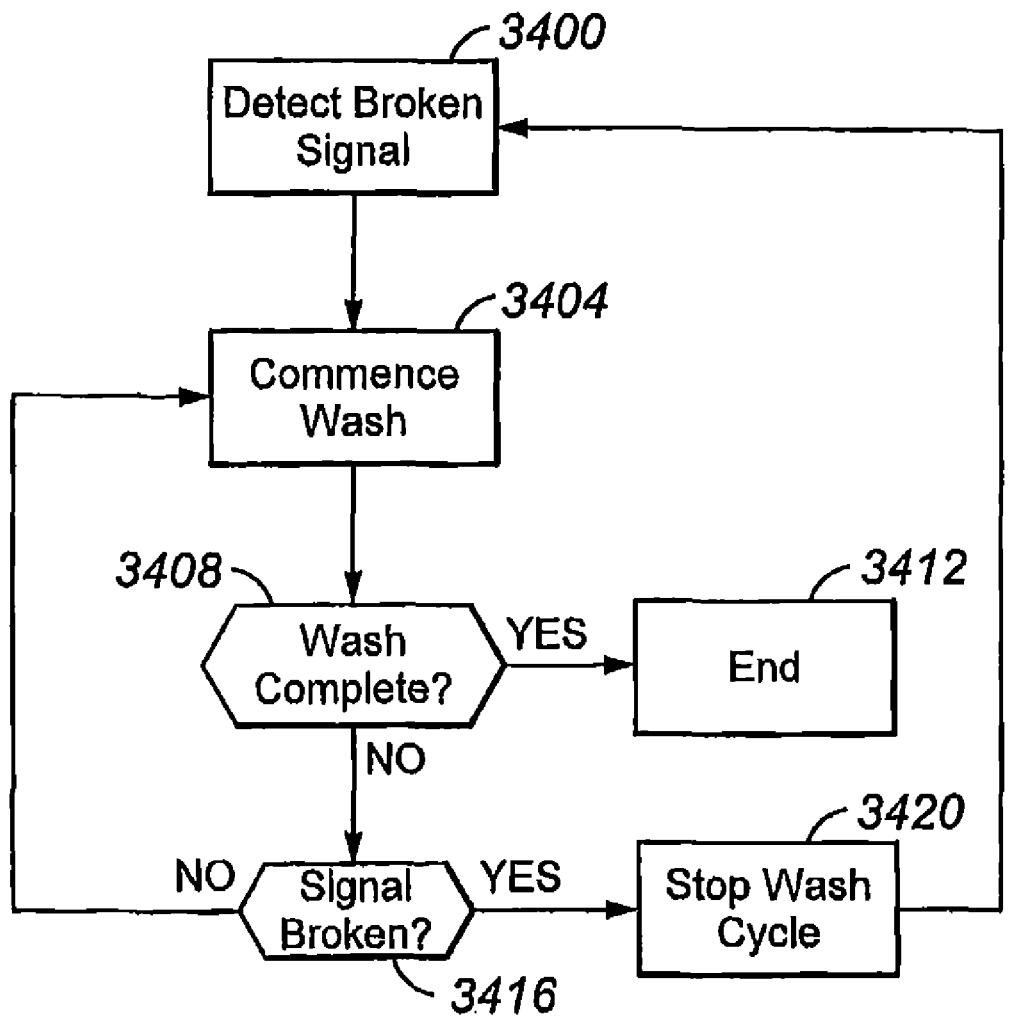
FIG. 34 is a flow chart showing a verification cycle in accordance with embodiments of the present invention.

Any of the above described automated cleaning stations may be used to prevent the false indication of compliance with a hygiene requirement. In particular, an automated cleaning stations may be used to ensure that hand washing in fact takes place. In contrast to automated cleaning stations, existing hand-sink monitoring systems may register that a hand washing took place when in fact none took place. For instance, existing hand-sink monitoring systems may register a complete hand wash after a faucet has been turned on for a predetermined amount of time. Here, hand-washing requirements may be easily falsified by a user simply turning on the faucet for the predetermined time and not placing his or her hands under the faucet. In contrast, an automated hand-washing station in accordance with embodiments of the present invention is operable to ensure or guarantee that a hand washing actually takes place. In particular, when the user places his or hands in the cylinder 220 an optical signal (e.g., light beam) is broken. As will be appreciated other radiation wavelengths may be used to detect the presence of the user's hands. For example, infra red sensors may be used to detect the thermal emissions of the user's hands. As a result, the automated cleaning cycle is initiated. The cleaning cycle continues provided that the signal remains broken (i.e. the hands remain in the cylinders). When the cleaning cycle is completed, it can be ensured that the hands were in the cylinders throughout the entire duration of the cleaning cycle. In this way, falsification of hand-washing requirements is prevented. This aspect of the present invention is diagrammed in the flow chart given in FIG. 34.

At step 3400, a detection of a broken optical signal is made. In particular, as the individual places his hands within the cylinders of the automated washing station, the individual's hands break an optical signal associated with the hygiene cylinders. After the broken optical signal is detected, step 3404 follows. In step 3404, a wash signal is generated and the hygiene cycle is initiated.

Step 3408 follows step 3404. In step 3408, a determination is made as to whether the wash cycle is complete. More particularly, a determination is made as to whether the required time has elapsed for the wash cycle to complete. If the wash cycle has allowed to complete, step 3412 follows. If the wash cycle is not yet finished, step 3416 follows.

In step 3412, the wash cycle is allowed to end. Herein the individual may remove his hands from the wash cylinders and a complete wash cycle is registered. In step 3416, wherein the wash cycle is not yet complete, the optical signal is continually monitored. If, in step 3416, it is determined that the wash signal is broken (i.e., the optical signal is restored) for at least a predetermined period of time, the method continues to step 3420. If the wash signal is restored (i.e., the optical signal is broken again) before the predetermined configurable time has elapsed, the removal of the user's hands from the optical signal path is deemed to be accidental or incidental and the wash is not determined to be compromised. The predetermined time preferably ranges from about 0.5 seconds to 5 seconds, and more preferably from about 0.5 seconds to about 3 seconds. Stated another way, the predetermined time ranges from about 5 percent to about 50 percent of the wash duration, and more preferably from about 5 percent to about 30 percent of the wash duration. In step 3420, it is determined that the individual has removed his hands from the wash cylinder prior to the end of a complete wash cycle. Herein a complete wash cycle is not registered and step 3400 follows, wherein the signal is again detected in preparation for a new wash cycle.

If in step 3416 the signal remains broken, step 3404 follows, wherein the wash cycle continues.

Figure 35:
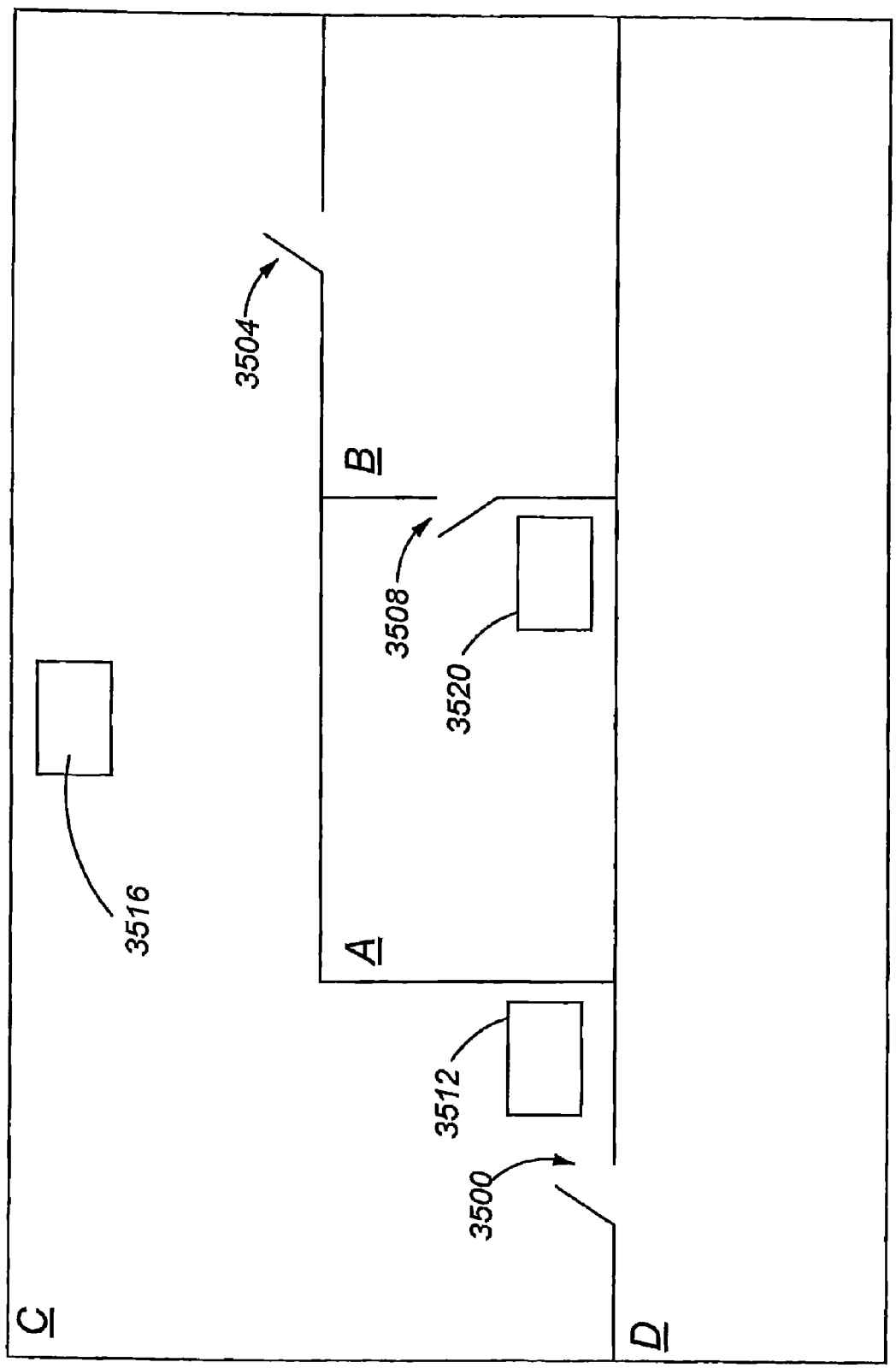
FIG. 35 is yet another schematic illustration of a hygiene system in accordance with embodiments of the present invention.

The deployment of various types of hygiene stations throughout a facility is illustrated in FIG. 35. Keeping with the example set forth above, the facility shown in FIG. 35 is considered to be hospital. Here, area A (hygiene level of 1) might correspond to a bathroom. Similarly, area B (hygiene level of 2) might correspond to a waiting area, area C (hygiene level of 3) might correspond to a staging area, and area D (hygiene level of 4) might correspond to a surgery wing. Here, door 3500 separates area C from area D. Door 3504 separates area B from area C. Door 3508 separates area B from area A. In implementing a hygiene protocol and/or in maintaining the hygiene levels set forth above, one or more hygiene stations may be strategically placed throughout the facility. For example, a surgical scrub hygiene station 3512 may be deployed near the door 3500 that leads into the surgery wing (area D). A complete hand care hygiene station 3516 may be deployed a central location in the staging area (area C).

In accordance with embodiments of the present invention, an automated cleaning station may be electronically coupled to a locking mechanism on a door, gate, turnstile, or other means for preventing ingress and egress. This aspect of the present invention is illustrated with reference to the surgical scrub hygiene station 3512 which is electronically coupled to a locking mechanism on the door 3508. Here, a person may be physically prevented from passing through the door 3508, if the person has not yet completed a verified wash cycle. In this way, it is ensured that an individual must have the required level radius before that individual enters the higher-level hygiene area. In particular, the person must place his or her hands within the scrub cylinders for the duration of complete wash cycle. After the wash cycle is completed, a signal may be sent to the door 3508, which causes the door to unlock allowing the person to pass through. As explained in connection with the verification cycle diagramed in FIG. 34, the use of an automated hygiene station in accordance with embodiments of the present invention prevents falsification and ensures that a hand washing actually takes place. Embodiments of the present invention include an emergency override that will disable to door locking mechanism.

In electronically coupling a hygiene station to a door, it may be the case that ingress or egress is prevented only at a certain time or in response to a certain event. Still referring to FIG. 35, it may be the case that ingress into the surgery wing is prevented pending a hygiene action only at the beginning of a shift. Here, individuals would be forced to initially perform a thorough hygiene scrub. Thereafter or throughout the remainder of the shift, individuals may be allowed to freely pass through the door 3500, between the surgery wing (area D) and the staging area (area C). This free passing may be made contingent on other factors. For example, free passage through the door 3500 may be contingent on the person not leaving the staging area C and going into a lower level hygiene area, namely the waiting room (area B). In addition, free passage through the door may be contingent on continued actions that would maintain a hygiene level. For example, use of the complete hand care station 3516.

In accordance with embodiments of the present invention, the hygiene requirements associated with an individual may depend on his or job title. In the hospital example give above, a surgeon may have different hygiene requirements from that of a social worker. Moreover, hygiene requirement may be imposed on or required of workers associated with a facility and not with visitors to the facility.

Figure 36:
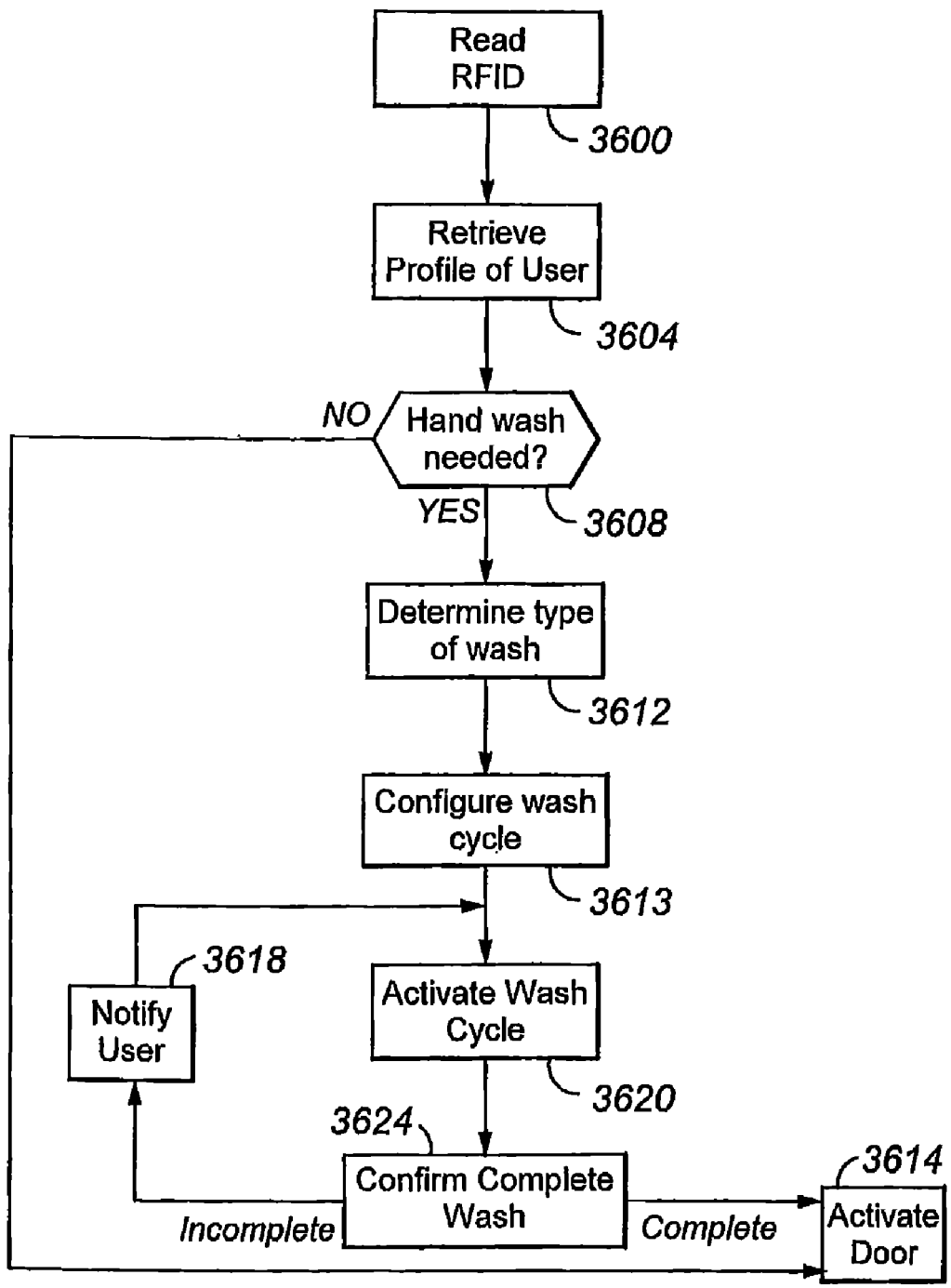
FIG. 36 is a flow chart showing a compliance method for in accordance with embodiments of the present invention.

An embodiment of the present invention, which employs both job title/visitor specific hygiene requirements and ingress/egress prevention, will now be described with continuing reference to FIG. 35. As shown in FIG. 35, the hospital facility includes an additional hygiene station 3520 in the bathroom (area A). The hygiene station 3520 may be electronically coupled to the door 3508 in order to physically prevent certain individuals from leaving the bathroom if they have not undergone a verified hygiene cycle. For example, if a surgeon uses the bathroom (area A) he or she may be physically prevented from leaving the bathroom pending a verified hygiene cycle. As can be appreciated, it would be desirable to only physically prevent certain individuals from leaving the bathroom. In particular, if visitors to the hospital were to use the bathroom it may not be desirable to physically prevent them from leaving the bathroom if they have not undergone a hygiene cycle. FIG. 36 shows a flow chart, which illustrates this aspect of the present invention.

In step 3600, an individual approaches an automated hand hygiene station or automated cleaning station and his or her RFID tag is read. Step 3604 follows 3600. At step 3604, the automated hygiene station downloads a profile specific to the user. At step 3608, a determination is made as to whether a hand wash is needed for this particular individual. If no hand wash is needed, the method continues to step 3612. At step 3612, the door is activated and the individual is allowed to pass through the door. This may correspond to the instance where the individual who has approached the hygiene station and door is a visitor to the facility. Herein the individual is not required by the facility to undergo any hand washing. Accordingly, the individual is allowed to pass through the door without having to undergo a verified hygiene cycle.

Step 3612 will follow step 3608 if it is determined that the individual requires a hand wash or other hygiene related action. At step 3612, a determination is made as to what type of wash is needed. Here the type of wash may be specific to the individual as indicated by his or her downloaded profile. Specifically, for certain individuals a higher level or more thorough hygiene cycle may be required. As described above, this may be the case in a hospital facility when the individual is a surgeon. Alternatively, a low level hygiene cycle may be required for in this example a social worker.

Following step 3612, the hand washing station is configured at step 3616. Step 3620 follows step 3616. At step 3620, the hygiene cycle is activated. Step 3624 follows step 3620. At step 3624, the completion of the hygiene cycle is confirmed. In particular, the hygiene station ensures that a wash was completed according to the steps set forth in the method illustrated in FIG. 19. If at step 3624 it is determined that the washing cycle was incomplete, step 3628 follows. At step 3628 the user is thereby notified that his or her washing cycle was incomplete. At this time, the door is not activated and the individual is not permitted to pass through. Accordingly, step 3620 follows step 3628 wherein a new hygiene cycle is initiated.

If at step 3624, it is determined that a complete wash cycle in fact took place, step 3612 follows. At step 3612 as described above, the door is activated and the individual is allowed to pass there through.

The present invention may be used in a wide variety of facilities, which may have different hygiene related requirements and/or needs. In addition, the present invention allows a particular facility to define and establish hygiene protocols that are specific to the facility. Using one or more of the aspects of the present invention set forth above, a hygiene protocol may be defined for a particular facility. Data may be collected in connection with monitoring of compliance with the hygiene protocol. The collected data may be complied for internal use only. Alternatively, the collected data may be provided to outside reporting agencies or other third parties.

Depending on the needs of a particular facility, the present invention allows for the implementation of a spectrum of hygiene protocols, from the loose to the more robust. For example, a loose hygiene protocol might allow individuals who have not meet a hygiene requirement to move through the facility. A more robust protocol might instruct such an individual to perform a hygiene related action and register a protocol violation if the individual fails to comply with the instruction. A still more robust protocol may physically prevent movement of an individual past a choke point if the individual has not complied with a hygiene requirement. A particular protocol may impose hygiene requirements on visitors to a facility that differ from those that work at the facility. For those that work at a particular facility, different hygiene requirements may be imposed based on job title.

In implementing a particular hygiene protocol, a facility may consider various factors described herein when determining the following parameters. In particular, a particular protocol may specify if hygiene radius violations are tolerated, whether contingent hygiene radius downgrading is allowed, and/or whether contingent zone contamination is allowed. Moreover, the facility's hygiene protocol may specify a time from a hygiene radius violation to a hygiene protocol violation. Second, the hygiene protocol may specify a time from a protocol violation to a zone contamination. Additionally, the protocol may specify the time in a lower level hygiene zone sufficient to cause a hygiene radius downgrade. Additionally, the protocol may specify the frequency of hand washing to maintain a particular hygiene radius value. A spectrum of different hygiene protocols may be implemented by a particular facility. Some hygiene protocols may employ location tracking as described herein. Moreover, it should be appreciated that a hygiene protocol may be established without reference to location tracking. Any hygiene compliance means as set forth herein may be used in establishing a hygiene protocol.

Referring now to FIG. 37, an exemplary multilevel hygiene protocol is generally identified by reference number 3700. For each hygiene level, a number of parameters are specified. For the exemplary hygiene protocol 3700 illustrated in FIG. 37, the following parameters are defined: hygiene requirements 3704, response to hygiene radius violation 3708, time to hygiene protocol violation 3712, allowability of contingent zone contamination 3716, time to zone contamination 3720, and response to zone contamination 3724. The hygiene protocol 3700 illustrated in FIG. 37 defines a series of hygiene levels with hygiene level 1 being the lowest level.

Hygiene level 1 indicated by reference number 3728 specifies no particular hygiene requirements. Accordingly, the hygiene parameters 3708 through 3724 are not applicable. Hygiene level 2, indicated by reference number 3732, includes more stringent hygiene requirements than hygiene level 1, indicated by reference number 3728.

Hygiene level 2 (3732) specifies that an alarm is given as a response to a hygiene radius violation. The time to hygiene protocol violation is one minute and contingent zone contamination is allowed. At hygiene level 2, zone contamination does not occur. Accordingly, no particular time is specified for a time to zone contamination, and no particular response is specified for a zone contamination.

Hygiene level 3 (3736) specifies more stringent hygiene requirements than hygiene level 2 (3732). In hygiene level 3 (3736), an alarm is given in response to a hygiene radius violation. A quicker time, namely, 30 seconds, is specified for a time to hygiene protocol violation. At hygiene level 3, contingent zone contamination is allowed. However, in contrast to level 2 (3732), one minute is specified for a time to zone contamination. In response to a zone contamination, hygiene level 3 (3736) specifies an alarm.

Hygiene level 4 (3740) specifies more stringent hygiene requirements than hygiene level 3 (3736). In hygiene level 4 (3740), an alarm is indicated in response to a hygiene radius violation. Zero seconds is specified as a time to hygiene protocol violation. Accordingly, a hygiene protocol violation occurs immediately following a hygiene radius violation. At hygiene level 4 (3740), contingent zone contamination is not allowed. Accordingly, zone contamination occurs immediately following a hygiene protocol violation. In particular, zero seconds is specified as the time to zone contamination. In response to the zone contamination, hygiene level 4 (3740) specifies an alarm and mechanical lockout workstations and/or doors that provide access to a particular area.

Turning now to FIG. 38, an exemplary multilevel hygiene protocol is generally referred to with reference number 3800. Hygiene protocol 3800 includes protocol identifier 3804 that allows multiple hygiene protocols to be defined for a particular hygiene level. A hygiene level may include different requirements depending on, for example, an employee type, job title, whether the monitored individual is an employee or a visitor to the facility, and any other requirement that specifies or requires individuals to have different hygiene requirements for a particular hygiene level. The remainder of the hygiene protocol parameters remain the same as the hygiene protocol 3700 shown in FIG. 37. For some hygiene levels in the hygiene protocol 3800, the hygiene requirements do not differ based on the protocol identifier 3804. More specifically, hygiene level 1 specifies requirements 3808a for protocol identifier 1 and requirements 3808b for protocol identifier 2 which are exactly the same. In particular, as hygiene level 1 is the least stringent hygiene level, no particular hygiene requirements are specified. Similarly, hygiene level 4, the most stringent hygiene level, requires the same hygiene requirements for each protocol identifier. Specifically, both hygiene level requirements 3820a for protocol identifier 1 and hygiene level 4 requirements 3820b for protocol identifier 2 specify an alarm given in response to a hygiene radius violation; zero seconds is the time to hygiene protocol violation; contingent zone contamination is not allowed; zero seconds to zone contamination; and alarm and lockout as a response to zone contamination. Turning now to hygiene level 2, the second most stringent hygiene requirement level, a hygiene requirement 3812a is specified for protocol identifier 1, and a hygiene level 2 requirement 3812b is specified for protocol identifier 2. For protocol identifier 2, level 1 specifies a one minute to hygiene protocol violation. For protocol identifier 2, level specifies no particular time to hygiene protocol violation. In this way, different hygiene requirements may be associated with different individuals. For example, an employee may be assigned protocol identifier 1, whereas a visitor may be assigned protocol identifier 2.

Turning now to FIG. 39, an exemplary hygiene compliance report is generally referred to with reference number 3900. The compliance report 3900 is compiled by the operation of the compliance monitoring module 630 based on a particular hygiene protocol. In particular, the compliance monitoring module 630 may implement a hygiene protocol, and in so doing produce a compliance report such as the compliance report 3900, shown in FIG. 39. For example, exemplary hygiene protocols 3700 or 3800 may be used to compile a hygiene compliance report 3900. The exemplary hygiene compliance report 3900 shown in FIG. 39 includes a number of parameters. Each entry in the hygiene compliance report 3900 specifies an entry that records an employee or visitor's transition across a hygiene boundary, which is recorded as hygiene compliance parameter 3902. Hygiene compliance report 3900 records transitions that occur from a lower level hygiene zone into a higher level hygiene zone. Compliance report 3900 may be provided in connection with the hygiene compliance 4000, shown in FIG. 40, which specifies transitions which occurred from a higher hygiene zone into a lower level hygiene zone. Compliance report 3900 and compliance report 4000 are shown separately for illustration purposes. It should be understood that these reports may be combined to provide a composite report that records all hygiene related events.

Turning first to hygiene compliance report 3900, the parameters include an employee ID 3904, a time in which the transition occurred 3908, a date 3912 which the transition occurred 3912, a hygiene radius value 3916 assigned to the individual when the individual transitioned across hygiene boundaries, whether a hygiene radius violation occurred 3920, the time to hygiene radius violation remediation 3924, whether a protocol violation occurred 3928, and whether a zone contamination occurred 3932. The hygiene compliance report 3900 records a number of hygiene zone boundary transitions 3936a through 3936g. Turning now to the compliance report 4000, which specifies hygiene boundary transitions that occurred from higher hygiene level to a lower hygiene level. Parameters associated with compliance report 4000 include an employee ID 3904, a time of day 3808, a date 3912, a hygiene radius during the transition 3916, whether a hygiene radius downgrade occurred 4004, and a time to hygiene radius downgrade 4008. The hygiene compliance report 4000 includes a number of entries 4012a-4012i that record hygiene zone boundary transitions. The hygiene zone boundary transitions recorded in compliance reports 3900 and 4000 are described and illustrated above with reference to FIGS. 11A-21D.

FIG. 41 illustrates yet another compliance report 4100 that may be produced by the operation of the compliance monitor 630. The hygiene compliance report 4100 includes a listing of hygiene radius violations that occurred during a particular day, including the results of these hygiene radius violations. In the exemplary hygiene compliance report 4100, six hygiene radius violations, 4104a-4104f occurred. For each hygiene radius violation 4104a-4104f, the hygiene compliance report 4100 specifies a hygiene radius violation number 4108, an employee ID 4112, a cause of the hygiene radius violation 4116, a time that the hygiene radius violation occurred 4120, a date which the hygiene radius violation occurred 4124, a time to hygiene radius violation remediation 4128, and whether or not a hygiene protocol violation occurred 4132. Hygiene radius violations 1-5 (4104a-4104e) record the hygiene radius violations that are specified in compliance report 3900. Compliance report 4100 additionally includes a hygiene radius violation 4104f that occurred as a result of a zone contamination.

Figure 42:
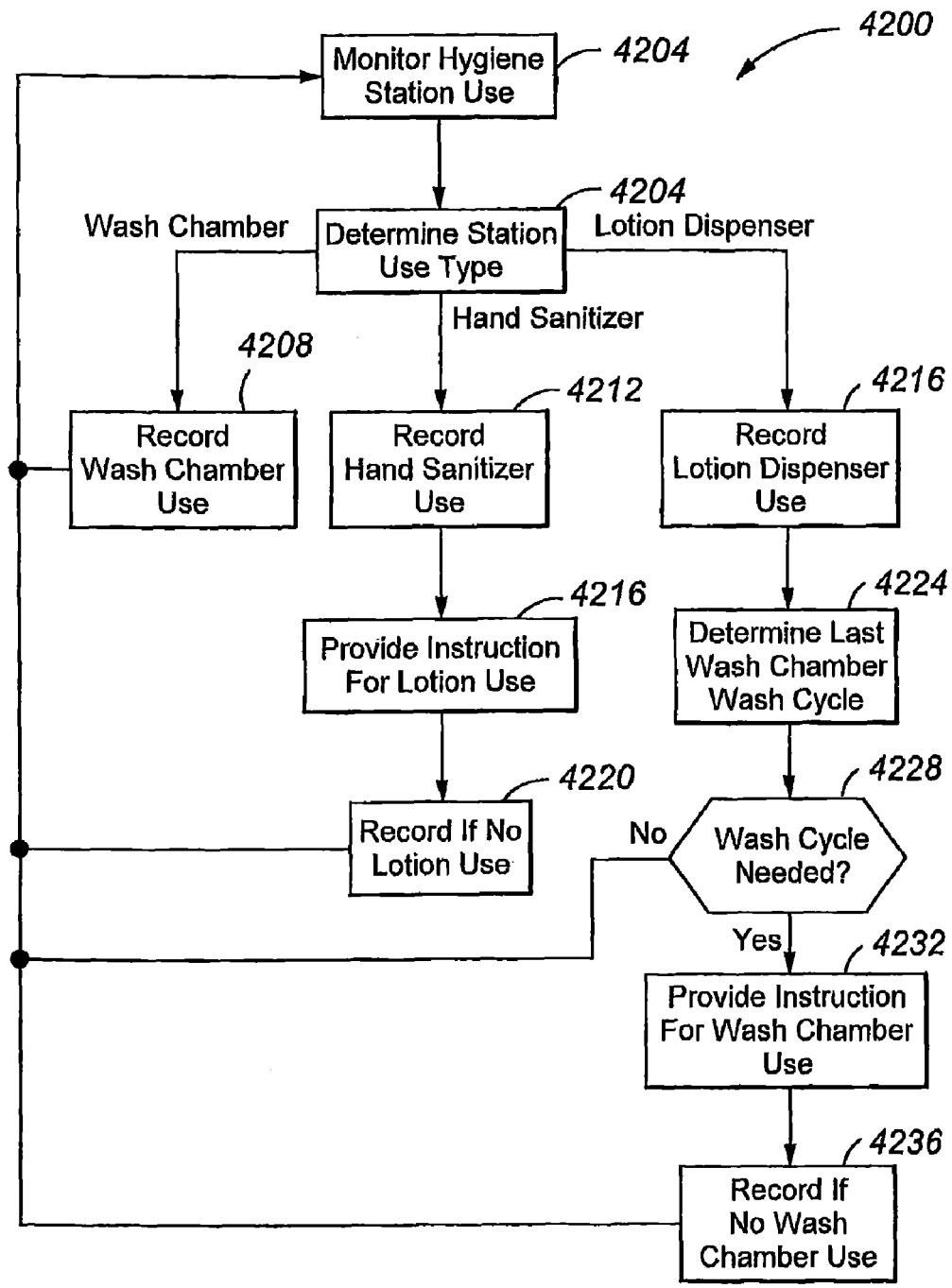
FIG. 42 is a flow chart showing another compliance method in accordance with embodiments of the present invention.

Embodiments of the present invention are directed to a compliance system and monitoring method used in connection with the complete hand care system shown in FIG. 33. FIG. 42 is a flow chart that illustrates a compliance monitoring method used in connection with the complete hand care station 3300. The method 4200 illustrated in FIG. 42 may be used to implement a particular hygiene protocol such as hygiene protocol 4300 illustrated in FIG. 43. Hygiene protocol 4300 includes requirements for daily hand washing, lotion use and mandatory complete hand washing. Parameters specified by the hygiene protocol 4300 include a hygiene requirement 4304, a frequency of the hygiene protocol requirement 4308, and a hygiene station component 4312 that is used to implement the hygiene requirement 4304. The first hygiene requirement 4316 is directed to a daily hand washing requirement. In particular, the hygiene protocol 4300 specifies (hygiene requirement 4304) a particular number (frequency 4308) of washes that must be achieved during a particular day. The daily washes may be implemented with the hygiene wash chamber 220 or the hand sanitizer 3200 as specified by hygiene station component parameter 4312. The next hygiene protocol requirement 4320 specifies that lotion must be used after every use of the hand sanitizer. Here, the lotion dispenser 3300 may be used to accomplish the hygiene requirement 4320. The next hygiene requirement 4324 specifies that a complete hand wash must be achieved after a predetermined number of uses of the lotion dispenser 3300. Here, the wash chamber only 220 must be used to carry out the hygiene requirement 4324. This set of hygiene requirements may be monitored using the method specified in FIG. 42.

Turning initially to step 4204, usage of the complete hand washing station 3300 is monitored. In step 4204, a type of hygiene station usage is determined. As there are three different hand station components, if the wash chamber 2200 is used, step 4208 follows. If the hand sanitizer is used, step 4212 follows. If the lotion dispenser is used, step 4216 follows. At step 4208, the usage of the wash chamber is recorded and the method proceeds again to step 4204. In step 4212, the use of hand sanitizer is recorded. At step 4216, an instruction is provided to the user indicating the need for lotion use. At step 4220, if the lotion is not used within a predetermined time, non-usage of the lotion dispenser is recorded. Step 4204 follows step 4220. At step 4216, use of the lotion dispenser is recorded. Following step 4216, a determination is made of the prior use history of the wash chamber at step 4224. At step 4228, a determination is made if a complete wash cycle is needed. If no wash cycle is needed, step 4204 follows step 4228. If a wash cycle is needed, step 4232 follows, which includes providing instructions to the user for usage of the wash chamber. At step 4236, if the wash chamber is not used within a predetermined time, recordation of the non-usage of the wash chamber is recorded and control passes again to step 4204.

In implementing the method 4200 shown in FIG. 42, the compliance monitor 630 may produce the compliance report 4400 shown in FIG. 44. The compliance report 4400 includes entries 4432a-4432s that record particular usages of the complete hygiene station 3300. For each entry in the compliance report 4400, the following components are specified: an employee ID 4404, a usage type 4408, a date 4412, a time 4416, an indication of compliance with daily requirements 4420, an indication of compliance with lotion use requirement 4428, and an indication with compliance of mandatory chamber use 4428. The compliance report 4400 shows compliance statistics for a single employee. It should be understood however, that compliance report 4400 may include compliance statistics for any number of employees. For the employees' compliance statistics shown in compliance report 4400, it can be seen that on a first day, the individual was out of compliance with daily washing requirements. On the second day, the individual was out of compliance with the lotion use requirement, and on the third day, the individual was out of compliance with the mandatory wash chamber use requirement.

Figure 45:
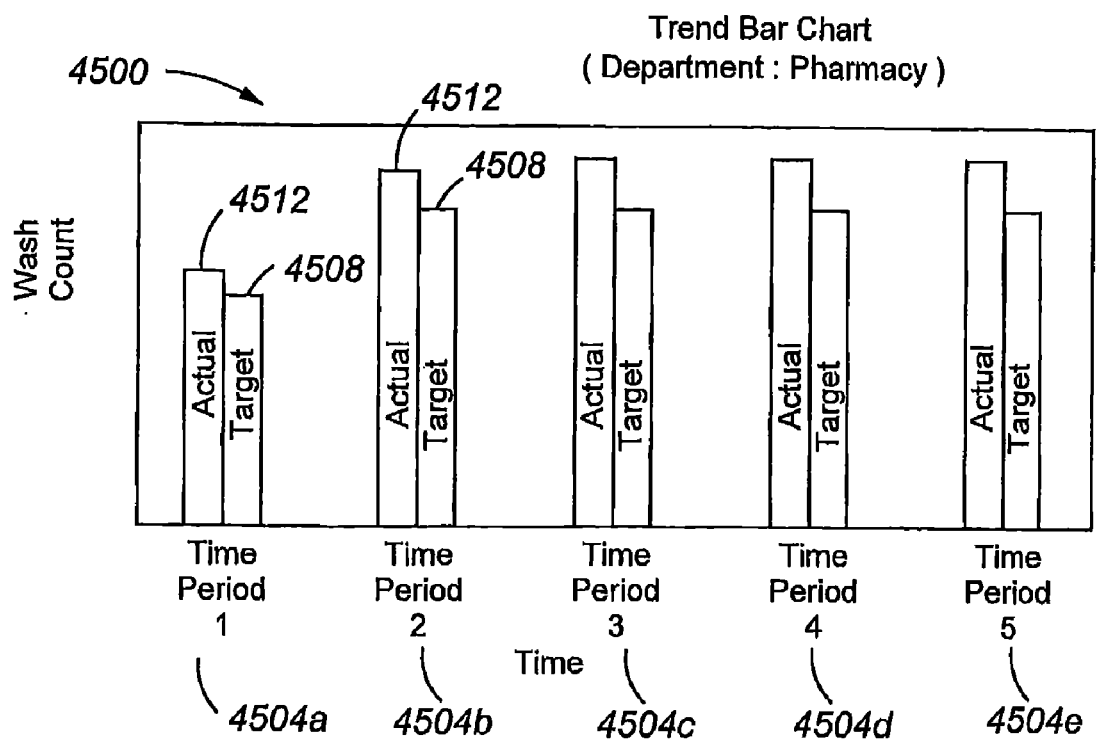
FIG. 45 is a graphical hygiene compliance report in accordance with embodiments of the present invention.

The compliance reports 640, 3900, 4000, 4100 and 4400 described herein include raw compliance statistics. In accordance with alternative embodiments of the present invention, compliance statistics may be analyzed and organized and presented in a compliance report that includes charts and/or graphs. An exemplary trend chart or bar graph compliance report 4500 is shown in FIG. 45. The bar graph 4500 shows compliance statistics for various time periods 4504a-4504e. For each time period, the compliance report 4500 includes an indication of the target compliance measurement 4508 in a side by side comparison with actual compliance statistics 4512. For the compliance report 4500, in the time period 4504a, it can be seen that the actual compliance statistics 4512 exceeded the target values 4508.

Figure 46:
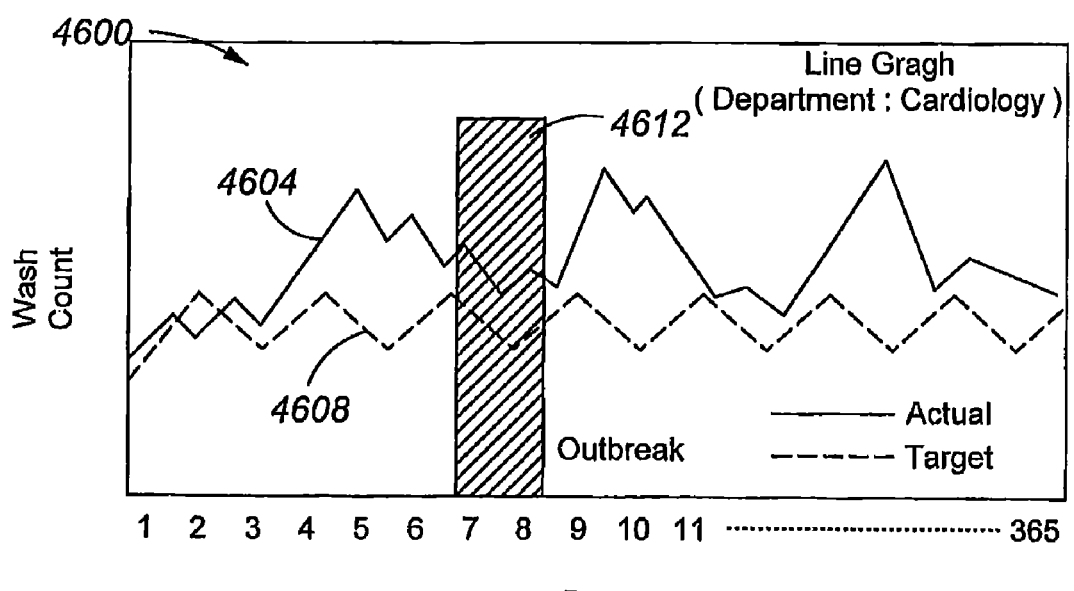
FIG. 46 is another graphical compliance report in accordance with embodiments of the present invention.

FIG. 46 shows a line graph 4600 showing compliance statistics for a cardiology department. The compliance report 4600 includes a line 4604 indicating the data points for actual wash counts on consecutive days. The compliance report 4600 additionally includes a line 4608 showing the target washes for each of the consecutive days. Additionally, FIG. 46 includes an indication 4612 of an outbreak which occurred between days 8 and 10.

In accordance with embodiments of the present invention, real time feedback may be provided to an employee in order to improve hygiene protocol compliance. This real time feedback may be provided through a computational device and displayed in a graphical user interface. The graphical user interface may be displayed on a screen such as display screen 224 associated with a particular hand hygiene station. In accordance with alternative embodiments of the present invention, the graphical user interface may be provided on a screen associated with a computational device that is a stand alone device and provided separately from a particular hand hygiene station.

Figure 47:
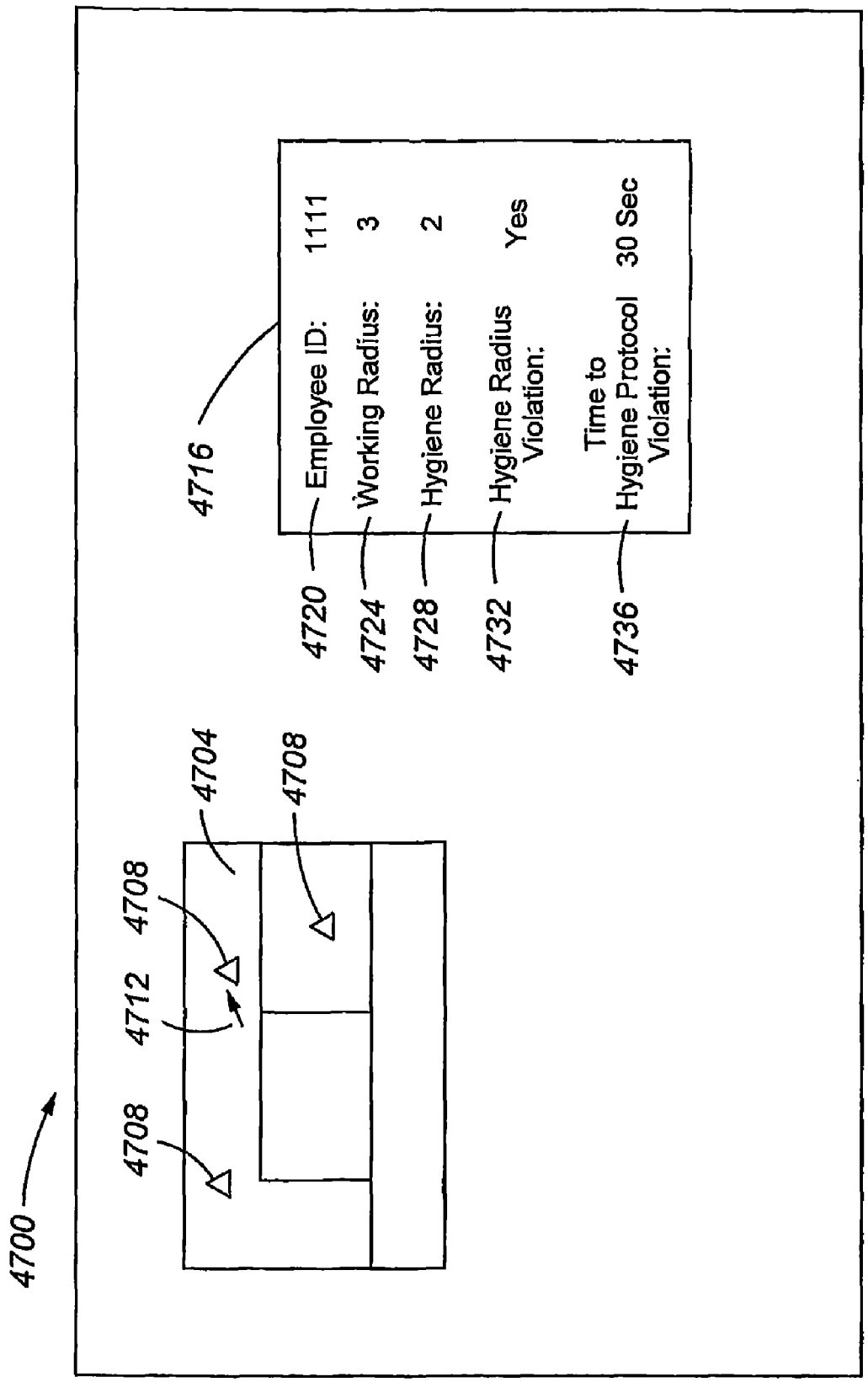
FIG. 47 is a schematic of a graphical user interface providing hygiene compliance information in accordance with embodiments of the present invention.

FIG. 47 shows an exemplary graphical user interface 4700. The graphical user interface 4700 includes a schematic layout of the facility in which monitored employees and/or visitors are located. The facility map 4704 includes icons 4708 that represent individuals and the individual's location within the facility. The icons 4708 may be accessed by a user who clicks on the icon using the mouse and associated mouse cursor 4712. In response, the graphical user interface may provide a drop down menu 4716 that includes current hygiene status information for the individual whose icon was accessed. The drop down menu 4716 includes hygiene information such as an employee ID 4720, a current working radius 4724, a current radius 4728, an indication if a hygiene radius violation has occurred 4732, and a current time to hygiene protocol violation 4736. These statistics may be used in order to allow the individual to remediate his deficient hygiene status as appropriate.

Figure 48A:
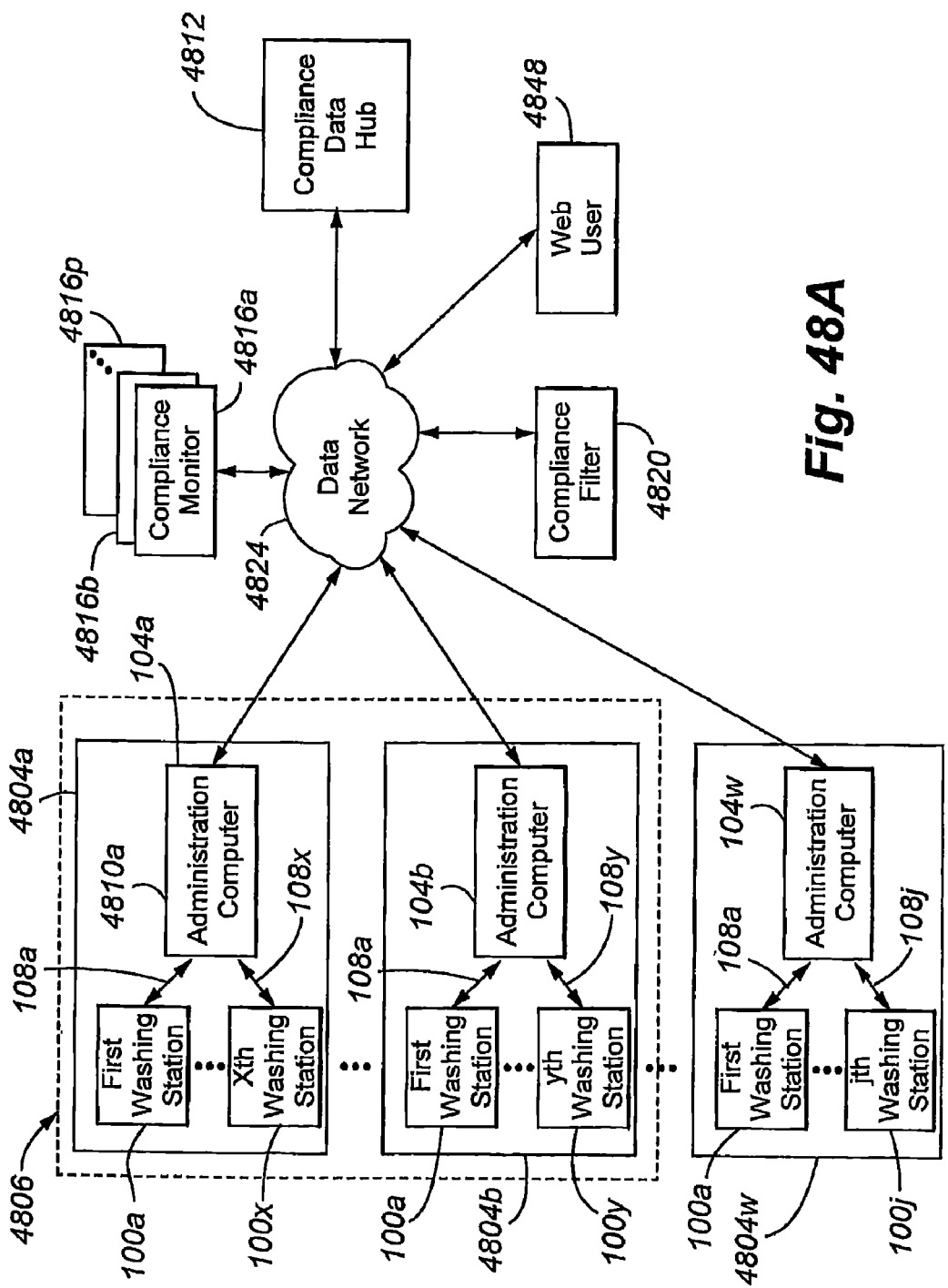
FIGS. 48A and 48B are illustrations of a compliance monitoring system according to another embodiment of the present invention.
Figure 48B:
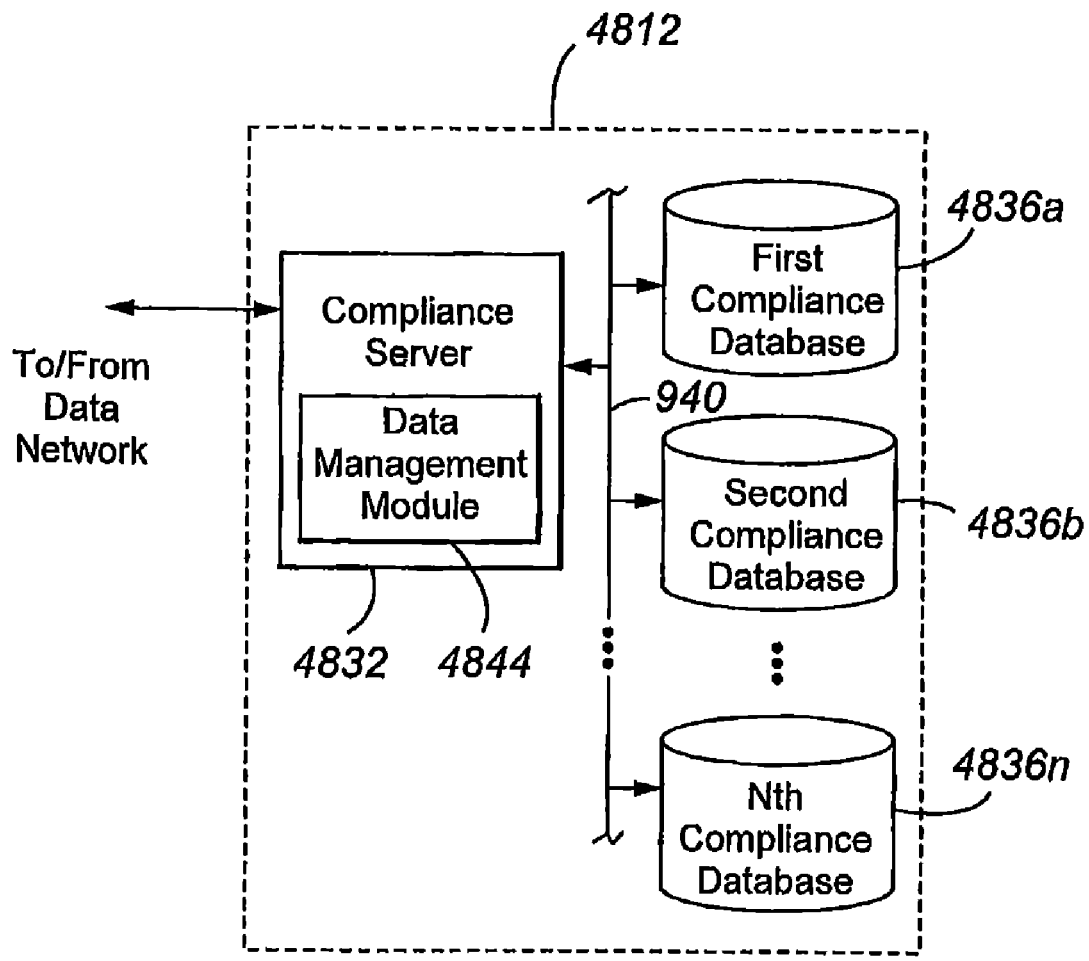

In another embodiment, a web-enabled hygiene monitoring system is provided. As shown in FIGS. 48A-B, the system 4800 includes a plurality of discrete monitored entities 4804a,b-w, each comprising first, second, . . . xth; first, second, . . . yth; or first, second, . . . jth washing stations 100a-x, 100a-y or 100a-j, respectively, a compliance data hub 4812, a compliance monitor 4816a,b-p, and a compliance filter 4820, all interconnected by a data network 4824.

The entities 4804a,b-w are each a monitored location. Particular monitored entities may be discrete facilities of a common monitored enterprise. For example, the automated compliance data hub 4812 may monitor a network of hospitals or restaurants. In one configuration, the compliance data hub 4812 processes and analyzes data received from the various locations, prepares reports, and provides user and administrator compliance feedback. Referring to FIG. 48A, the monitored entities 4804a and 4804b represent different locations associated with a common business enterprise 4806. Alternatively, a monitored enterprise may include only one monitored entity. In FIG. 48A, monitored entity 4804w represents a separate business enterprise. In other words, the compliance data hub 4812 may be associated with a plurality of business enterprises that are owned and operated by different companies, and one or more of those enterprises may include a plurality of different locations or facilities. Examples of enterprises include health care providers, food service providers (e.g., restaurants), food and/or drink manufacturers (e.g., meat packing plants, dairy product manufacturers, and the like), and other types of providers subject to internal and/or regulatory cleaning requirements.

In accordance with embodiments of the present invention, each monitored entity 4804 network includes an administration computer 104a,b-w or data collection point that collects cleaning information from each washing station 100a-x, a-y, a-j in the corresponding enterprise network and, periodically or continually, provides the information to the compliance server 4832 (shown in FIG. 48B) of the compliance data hub 4812. As can be appreciated, an administration computer may be a network computer or server and may include a database. In this configuration, the cleaning information may be pushed by the administration computer 104a,b-w to the compliance server 4832 or pulled from the administration computer 104a, b-w by the compliance server 4832. Furthermore, it is noted that configuration of the each monitored entity 4804a,b-w substantially corresponds to the embodiment of the present invention shown in FIG. 1.

Each administration computer 104a,b-w may include a user interface through which employee related data may be entered. The user interface may be implemented using any suitable software package (such as Access 2003) and can include portions that are icon driven to facilitate data entry and include drop down menus to ensure consistency of data. Additionally, data may be dynamically saved when possible. The user interface may include a plurality of screens wherein data is saved after a screen is changed. When changing screens, a user may be prompted to enter data not previously saved. Moreover, mandatory data fields may be supported for a software version.

The washing stations 100a-x, a-y, a-j can be any type of cleaning equipment and are typically at different spatial locations in the monitored entity. Examples of washing stations include manual and automated body member (e.g., hand, foot, etc.) and other object washing stations, such as automated hand washers, sinks/faucets and cleaning solution dispensers, and the like. As will be appreciated, "object" refers to living or animate organisms, such as people and animals, as well as inanimate objects or entities, such as equipment and tools.

As discussed below, each monitored entity 4804a, b-w has a corresponding unique monitored entity identifier, and, within each monitored entity 4804a, b-w, each washing station 100a-x, a-y, a-j has a unique station identifier. Accordingly, each pairing of monitored entity and station identifiers is unique. In one configuration, an object type identifier (not shown) is used in addition to the employee type identifier. The object type identifier refers to animate and inanimate objects, each of which has a unique or substantially unique identifier. While the identifier is carried removably by persons, the identifier may be attached permanently or semi-permanently to the inanimate object. The identifier can be, for example, a passive RFID tag, a bar code label, and the like. Unlike employee identifiers, which, for an enterprise, are unique, inanimate object identifiers may not be unique for each individual object in the enterprise but unique for a class of objects of the same type. Thus, objects of the same type have a common identifier, while objects of different types have different identifiers.

Each washing station 100a-x, a-y, a-j includes a compliance module 316 that in turn includes a processor and computer readable storage medium. The compliance module 316 identifies objects to be cleaned, determines a suitable cleaning protocol for the object to be cleaned, records object identifiers, object type identifiers, cleaning protocol identifiers, timestamps, compliance indicators, alert instances, and the like, determines the compliance or noncompliance of a cleaning, and generates appropriate alerts. Additionally, each washing station 100a-x, a-y, a-j can further include modules to determine whether the operational status of the corresponding washing station or a component thereof. As noted, the operational status includes not only whether the washing station or a component thereof is fully or partly operational or nonoperational, but also quantitatively a current level or remaining amount of a consumable item, such as soap or a cleaning/antimicrobial solution, or qualitatively whether the consumable level falls below a threshold level. Each module 316 may be associated with a memory 304 that typically includes a record or lookup table listing, by employee identifier, a corresponding cleaning protocol identifier.

The compliance data hub 4812 generally collects, stores, and analyzes cleaning information from the various administration computers 104a, b-w. (The administration computers 104a, b-w having collected hand-washing data from the individual cleaning stations 100a-x, a-y, a-j.) The compliance data hub 4812 includes a compliance server 4832 for receiving cleaning information and forwarding the cleaning information to an appropriate storage location in the compliance data hub 4812, and for retrieving requested cleaning information from an appropriate storage location and forwarding the information to an authorized and verified entity, such as compliance monitor 4816a, b-p. In that regard, the compliance data hub 4812 further includes one or more databases 4836a-n for storing cleaning information and a Local Area Network 4840 interconnecting the databases with the server 4832. The databases 4836a-n may be separate, as shown, with each database corresponding to a monitored entity 4804a-n or a single database partitioned into segments, one segment for each monitored entity 4804. The databases 4836a-n may be implemented using suitable database software (such as SQL Server Express).

The various administration computers 104a, b-w associated with the various monitored entities may support modules that communicate with compliance data hub 4812. In accordance with embodiments of the present invention, it may by necessary to import a license token from the compliance data hub 4812 in order to enable modules used at the administration computer level. The token may be specific to a particular enterprise and may include: the company name, a primary contact and primary contact information, a secondary contact and secondary contact information, the number of licensed users, and the type of service supported. In accordance with embodiments of the present invention, the token may be an encrypted string of text that will be delivered as a token license file. Moreover, the compliance data hub 4812 may periodically access and/or update modules at the administration computer level. In accordance with embodiments of the present invention, an email may be generated providing notice that a particular module was accessed or updated.

As shown in FIG. 48B, the compliance server 4832 includes a data management module 4844 that queries administration computers 104a,b-w for cleaning information, forwards received cleaning information to an appropriate database 4836 for storage, receives requests for cleaning information and, after successful authentication and verification of the request source, retrieves and forwards the requested cleaning information to the requesting source, and analyzes the cleaning information for instances of compliance and/or noncompliance events.

The data management module 4844 is operable to provide a data management module report. An exemplary data management module report 1000 is shown in FIG. 49. The data management module report 4900 may include an enterprise identification number 4904. The compliance data hub 4812 may assign a unique enterprise identification number 4904 to each business enterprise monitored by the compliance data hub 4812. For example, the enterprise identification number 4904 having a value "123456", as shown in FIG. 49, may be associated with the business enterprise 4806 shown in FIG. 48. A particular compliance data report 1000 may be provided in connection with a particular business enterprise and will typically not include compliance data associated with other entities monitored by the compliance data hub 4812. In particular, monitored entity 4804w, which is not part of business enterprise 4806, would be associated with a different enterprise identification number 4904. Accordingly, compliance data associated with the monitored entity 4804w would not appear on the exemplary compliance data module report shown in FIG. 49. The data hub 4812 may maintain a contacts module operable to store and track contact information associated with each monitored business enterprise.

The data management module report 4900 may additionally include a station identification number 4908 and a user identification number 4912. For a particular entry in the report 4900, the station identification number 4908 indicates the particular washing station where the washing took place. The user identification number 4912 is associated with a particular individual, such as an employee. Accordingly, for a particular entry in the report the user identification number indicates who used the washing station. Each entry in the report 4900 includes a date 4916 and time 4920 indication when the washing took place. A facility identifier 4924 may also be included if the monitored enterprise associated with the report 4900 includes more than one location or facility. The facility identifier 4924 may indicate in which facility within a particular enterprise the washing took place. The report also includes an indication 4928 of whether or not a complete wash cycle wash performed.

Additionally, the data management module report 4900 may include a compliance monitor identification number 4932. The compliance monitor identification number 4932 may be used to indicate which compliance monitor 4816a, b-p of a plurality of compliance monitors 4816a, b-p is currently receiving or will be receiving compliance data associated with a particular item in the data management module report 4900. In addition or in the alternative, the compliance monitor identification number 4932 may be used by the compliance filter 4820 in connection with determining which data items in the data management module report will be sent to the compliance monitors 4816a, b-p. It should be appreciated that a particular report may include other fields not shown in FIG. 49. For instance, the report may include a wash station name or a wash station IP address.

The exemplary data module report 4900, shown in FIG. 49, includes exemplary compliance statistics such as Boolean value indication of whether or not an individual identified by a particular user ID number completed a hygiene requirement. Additionally, the report indicates that the individual is associated with a particular enterprise, i.e., identified by a particular enterprise ID number. It should be understood that any of the compliance statistics discussed and described herein may be provided in connection with a data management module report 4900. In particular, a data management module report 4900 may include time stamp information, duration, date, percentage of hand washing statistics, current training segment statistics, allergy information, preferred entertainment content information. In embodiments of the present invention where location tracking is provided, a data management module report 4900 may include such hygiene protocol parameters as hygiene boundary transition information including time, date, level indications, hygiene radius violations, hygiene protocol violations, time to hygiene radius violation remediation, zone contamination statistics, hygiene radius downgrade statistics, time to hygiene downgrade information, time to remediation of hygiene radius violations that occur as a result of zone contamination. In embodiments of the present invention that include a complete hand care station, a data management module report 4900 may include statistics such as compliance with daily hand washing requirements, compliance with lotion use requirements and compliance with mandatory wash chamber use requirements. In accordance with alternative embodiments of the present invention, a data management module report 4900 may include graphical information such as the graphical information presented in the bar chart 4500 and/or the line graph chart 4600. In accordance with still alternative embodiments of the present invention, an interactive graphical user interface such as the one shown in FIG. 47 may be included in a data management module report. In this embodiment, an individual who is monitoring hygiene compliance may actively monitor the current status of one or more employees by accessing graphical icons that represent the employees and thereby accessing drop down menus which provide real time information indicating compliance with hygiene protocol requirements and/or current hygiene status.

Data management module reports 4900 may be generated at different time intervals and may be grouped based on different criteria. For example, reports 4900 may be generated daily, weekly, monthly, yearly, et cetera. Moreover, reports 4900 may be generated that are grouped by individual, company, facility, station, et cetera.

The compliance hub 4812 may allow particular individuals to access stored data and/or reports including the data management module report 4900. In accordance with embodiments of the present invention, a report 4900 may be accessed remotely through a web interface. In that regard, web user 4848, with proper access permission, can access compliance data stored in the compliance data hub 4812. Particular individuals given access to stored data may include, for example, company managers and/or officers. As described in greater detail below, a report may be provided to a compliance monitor 4816a, b-p.

Access to data management module reports 4900 and other stored data may be limited and/or controlled by a security system. In that regard, the data compliance hub 4812 may include a group security module that provides a password protected control to stored data. The level of access allowed to a particular individual may be based on their membership in a particular group. Particular groups can include, for example, account manager, customer, demo, administration, data hub administration, and developer. Particular functions such as view, store and print may be useable based on the level of access granted.

The compliance data hub 4812 can perform a variety of data processing functions. The compliance data hub 4832, for example, can compare cleaning information, or a given sensed parameter, to identify events, temporal trends, or differences and, if necessary, generate appropriate alarms. The alarms can be logged internally and/or forwarded to the respective cleaning station 100a-x, a-y, a-j. The cleaning station 100a-x, a-y, a-j can then provide the alarm or warning to the appropriate cleaned object that, for instance, the cleaning provided was not compliant. An exemplary alarm may be "Successful Cleaning", "Warning Cleaning Failed", and the like. In another configuration, the alarm is that a consumable level is low and requires replacement or that the wrong consumable is being used. The compliance data hub 4812 can also provide communications to the cleaning stations. The communications can, for example, be audio and video information for display to users of the stations. As will be appreciated, the audio and video information may be streaming media transmitted over the data network 4824, including, but not limited to, video transmitted to video display 224.

In one configuration, the databases 4836 further include, or reference, information collected and stored by the enterprise security system (not shown). For example, employee badge activated entrances typically collect the badge identifier (or employee identifier) and a timestamp when the badge identifier was received. Such information can be used in analyzing compliance by determining whether the employer having the sensed badge identifier used the washing station in temporal proximity to passing through the secured entrance. As will be appreciated, the spatial locations of activated entrances and washing stations are known and can be used, collectively, to monitor compliance.

The one or more compliance monitors 916a, b-p may be, for example, an entity responsible for monitoring and/or otherwise administering the hygiene policies and/or requirements of the one or more enterprises associated with the monitored entities 904. The monitor may be a governmental entity, such as a department of health and human services and the U.S. Food and Drug Administration, to name but a few, or a private entity such as a hygiene administration department. Typically, a plurality of compliance monitors 4816a, b-p are involved, with each monitor being associated with a different local, state, or national (federal) government entity. By way of example, a facility of an enterprise 4806 may need to report compliance data to multiple compliance monitors 4816a, b-p, such as at the city or municipality, county, state, and federal levels.

In one or more embodiments of the present invention, a compliance filter 4820 may be used. The compliance filter 4820, in one configuration, receives outgoing transmissions of cleaning information and filters the information before it is provided to one or more of the compliance monitors 4816a, b-p. The compliance filter 4820 may be part of or separate from (as shown) the compliance data hub 4812. The compliance filter 4820 ensures that cleaning information from different monitored enterprises 4806 is not intermixed and only necessary cleaning information is provided to the compliance monitor 4816a, b-p, thereby protecting client/customer confidentiality and legally recognized privileges. In one configuration, the compliance filter 4820 is a law firm responsible for and knowledgeable about compliance monitoring requirements. Attorneys may review the cleaning information and maintain the confidentiality of the cleaning information under the attorney-client privilege. Furthermore, in at least one embodiment, the compliance filter 4820 is an auditing entity other than a law firm.

The data network 4824 can be any circuit- or packet-switched network, with a packet-switched network, such as the Internet or World Wide Web, being preferred.

The cleaning information is typically converted into a selected form, packetized, and transmitted over the network 4824. The form of the information can be in accordance with any selected language, such as the eXtensible Markup Language or XML, the HyperText Markup Language or HTML, Remote Method Invocation or RMI, or Direct Socket Connections. The packets can be transported using any suitable protocol, such as the Transport Control Protocol/Internet Protocol suite of protocols, Simple Object Access Protocol, or User Datagram Protocol.

An exemplary graphical user interface ("GUI") for the compliance data hub 4812 will now be discussed. The GUI can be accessed from a washing station 100, administration computer 4810, a compliance monitor 4816, or Web browser (not shown) operated by a Web user 4848.

Figure 53A:
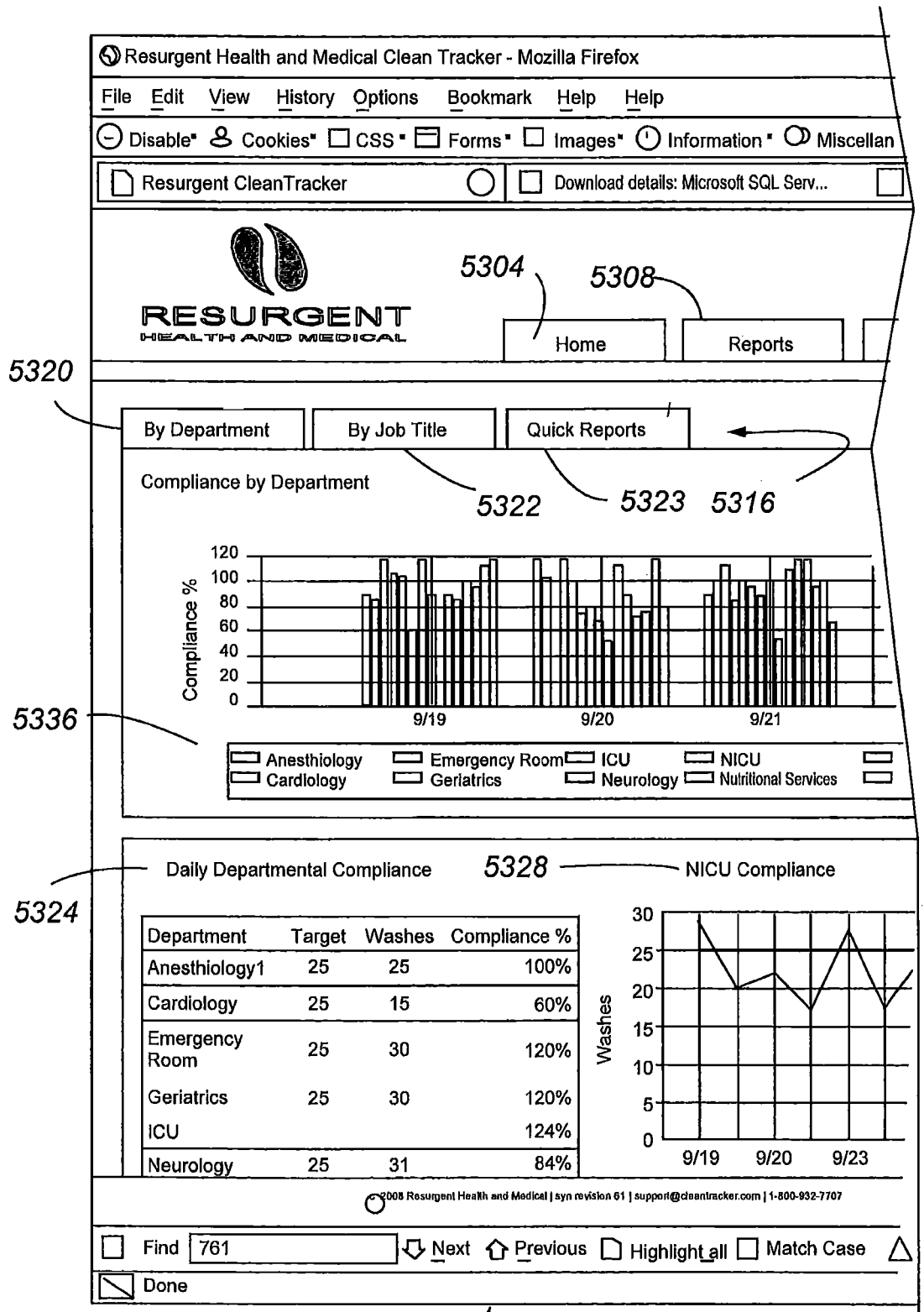
FIGS. 53A-53B is a screenshot according to an embodiment.
Figure 53B:
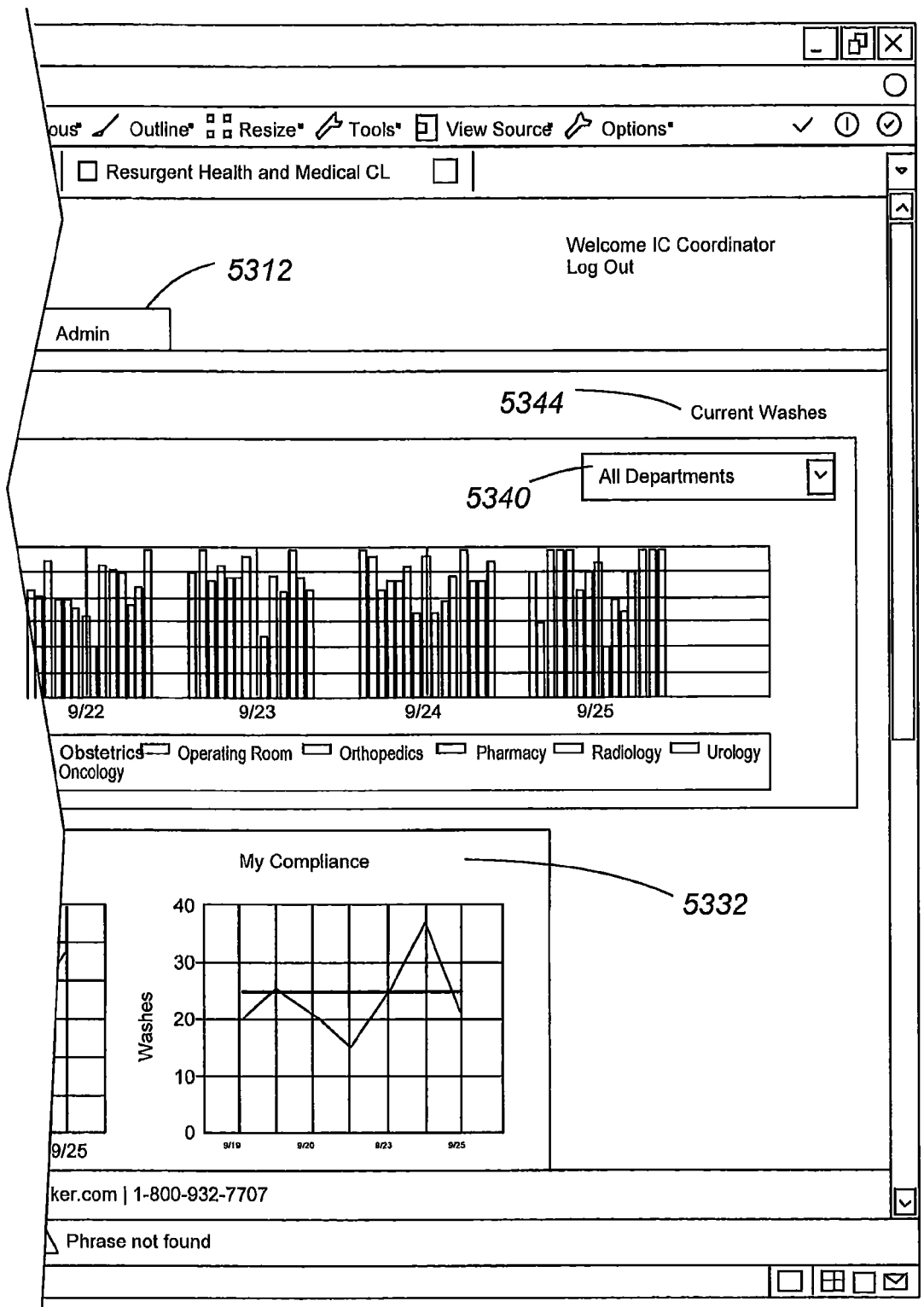

A screen shot of a GUI page is shown in FIGS. 53A-53B.

Referring to FIGS. 53A-53B, GUI page 5300 includes home, reports, and administrative tabs 5304, 5308, and 5312, respectively.

The home tab 5304 contains a (weekly) compliance dashboard 5316 that reports up-to-date hand-washing statistics that can be viewed in various chart forms, including compliance by department 5320 (shown), compliance by job title 5322, and quick reports 5323 tabs.

In FIGS. 53A-53B, the compliance by department tab 5320 is selected, which produces a number of tables of charts, namely daily departmental compliance 5324, Neonatal Intensive Care Unit compliance 5328, and my (current user) compliance 5332. Although discussed as a weekly compliance dashboard, the compliance dashboard can be determined over any suitable recurring time period. The compliance-by-department chart 5336 offers comparative bar charts by department for the recurring time period (shown as being a week). The vertical axis (height of the bars) reflects compliance by percentage of set goals (which can vary by department). Departments are selected by a pull-down selector 5340 that offers the choice of "all" or "individual" department views.

The departments shown in FIGS. 53A-53B are for a health care facility and include, in addition to NICU, anesthesiologist, cardiology, emergency room, geriatrics, intensive care unit ("ICU"), neurology, nutritional services, obstetrics, oncology, operating room, orthopedics, pharmacy, and radiology.

Figure 54B:
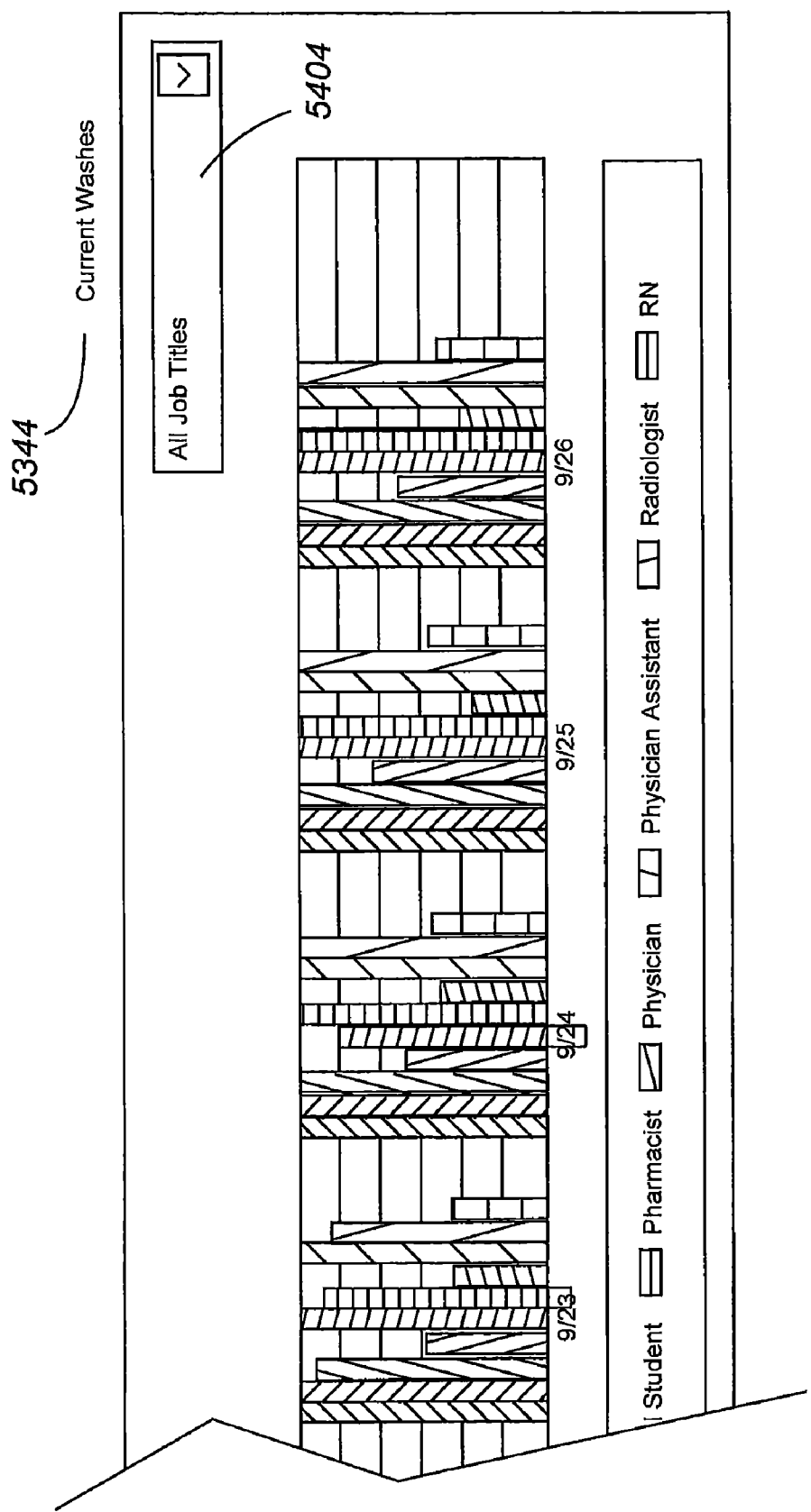

Referring to FIGS. 54A-54B, the compliance by job title tab 5322 offers comparative bar charts 5400 for job title for the last week. The job titles include administrator, food service, laboratory technician, licensed practical nurse ("LPN"), medical student, pharmacist, physician, physician assistant, radiologist, and registered nurse ("RN"). The vertical axis (height of the bars) reflects compliance by percentage of set goals, which can vary by job title. Job titles can be selected through a pull-down selector 5404 that offers the choice of "all" or "individual" job-title views.

The quick reports tab 5323 displays all the report configurations that have been saved from the compliance by department and compliance by job title search boxes. Clicking on one of the displayed links will launch the report with preconfigured parameters, with all the same functionalities a normally-generated report has.

A current washes quick reference 5344 takes the user directly to the current washes section of the quick reports tab 5323. This provides information on all of the latest washes in the saved in the system for that monitored entity.

Referring to FIG. 55, the daily compartment compliance chart 5324 breaks down departmental compliance to a spreadsheet format. The table headers include department, target, washes, and compliance percentage (relative to set goals, targets, or bench marks). To enhance readability, selected rows may be color coded based on the department's compliance status. For example, green indicates greater than 90% of the target washes or goal has been met. Yellow indicates that greater than or equal to 75% of the target washes has been met. Red indicates that less than 75% of the daily departmental target washes have been met.

Figure 56:
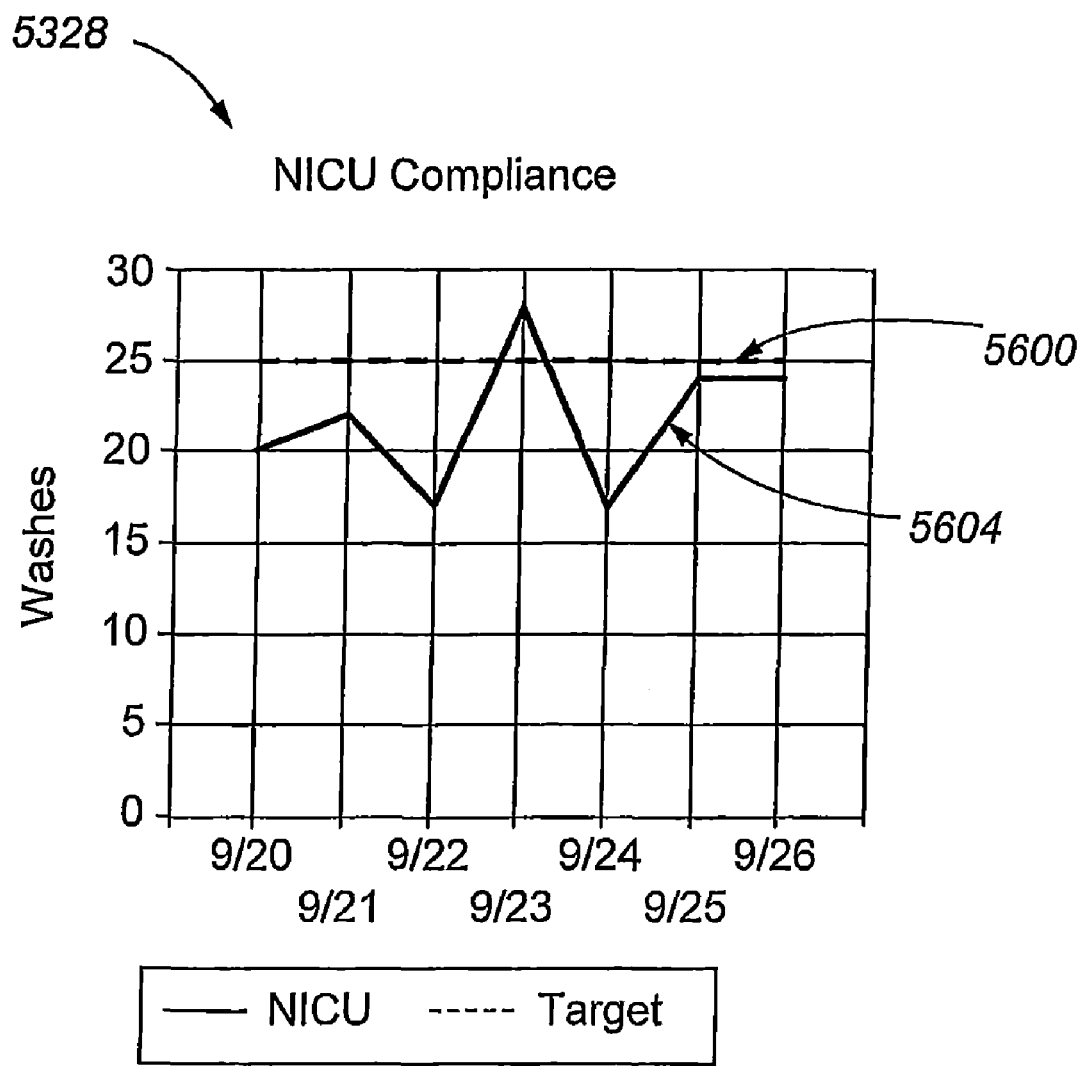
FIG. 56 is a screenshot according to an embodiment.

Referring to FIG. 56, the NICU compliance chart 5328 depicts data specific to a more important department (NICU) for the past reporting period (week). The dashed red line 5600 indicates target washes, and the moving blue line 5604 represents daily washes relative to the target for the week of September 20 to September 26.

Figure 57:
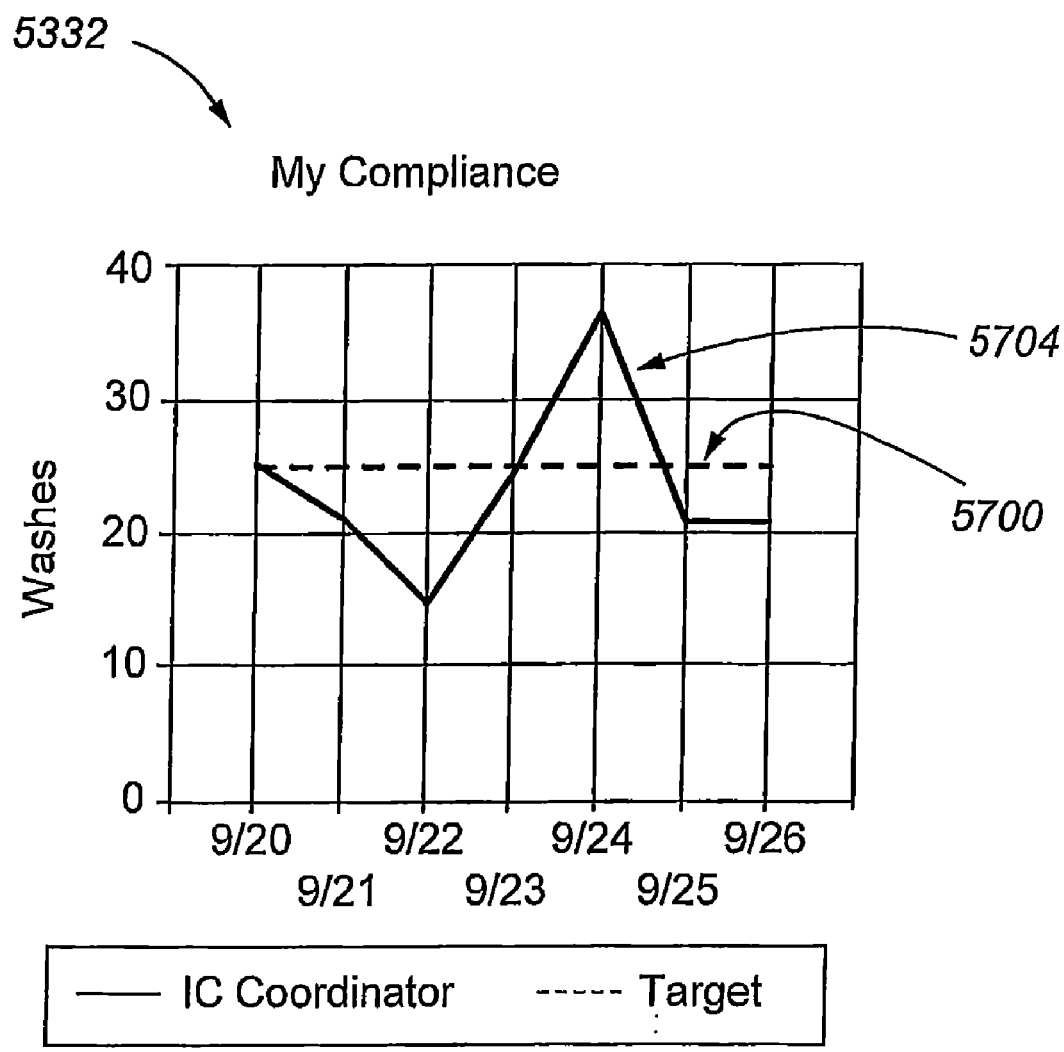
FIG. 57 is a screenshot according to an embodiment.

Referring to FIG. 57, the my (current user) compliance chart 5332 depicts data specific to the active user for the past reporting period (week). The dashed red line 5700 indicates targeted washes, and the moving blue line 5704 represents daily washes relative to the target for the week of September 20 to September 26.

Figure 58A:
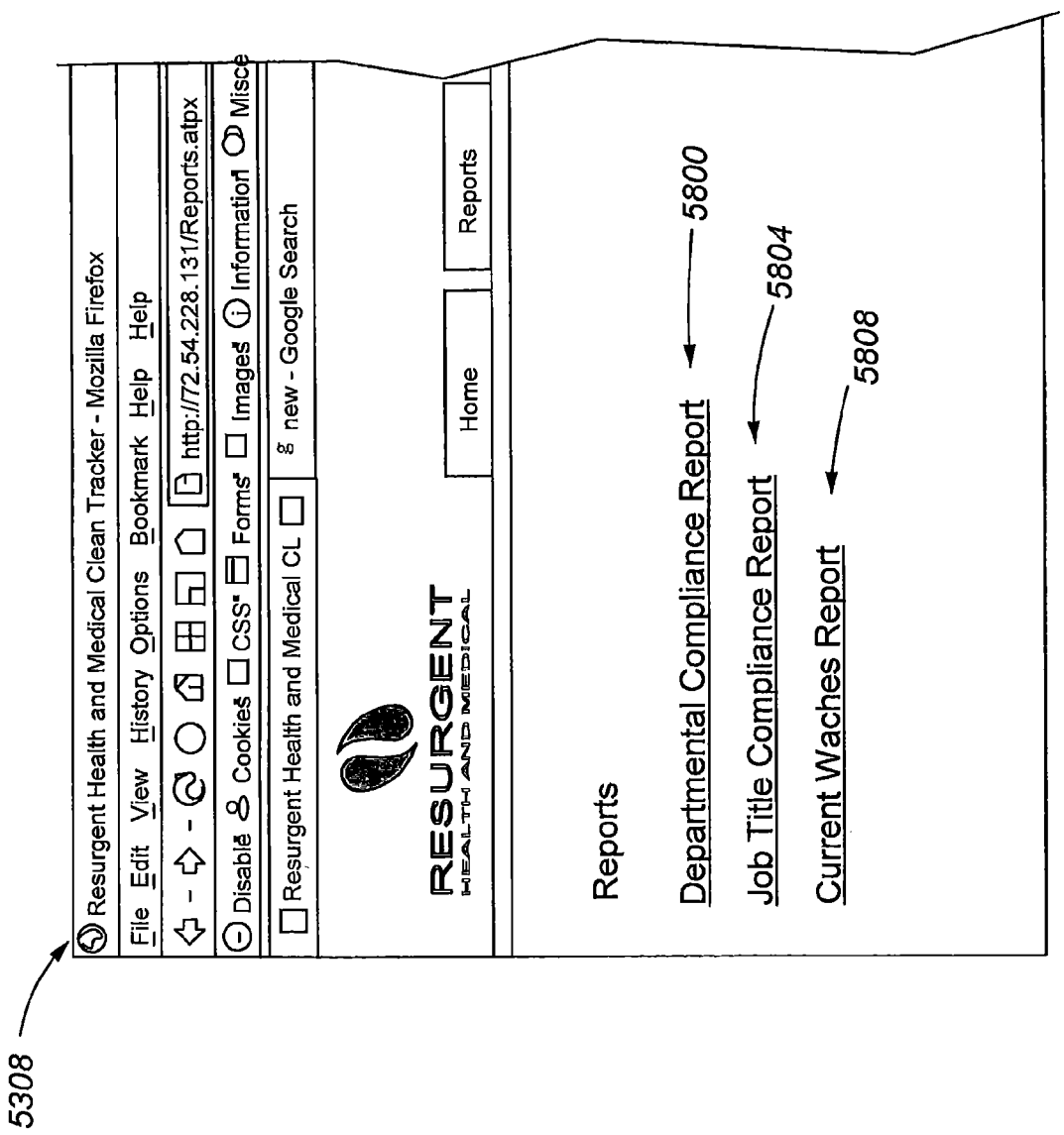
FIGS. 58A-58B is a screenshot according to an embodiment.
Figure 58B:
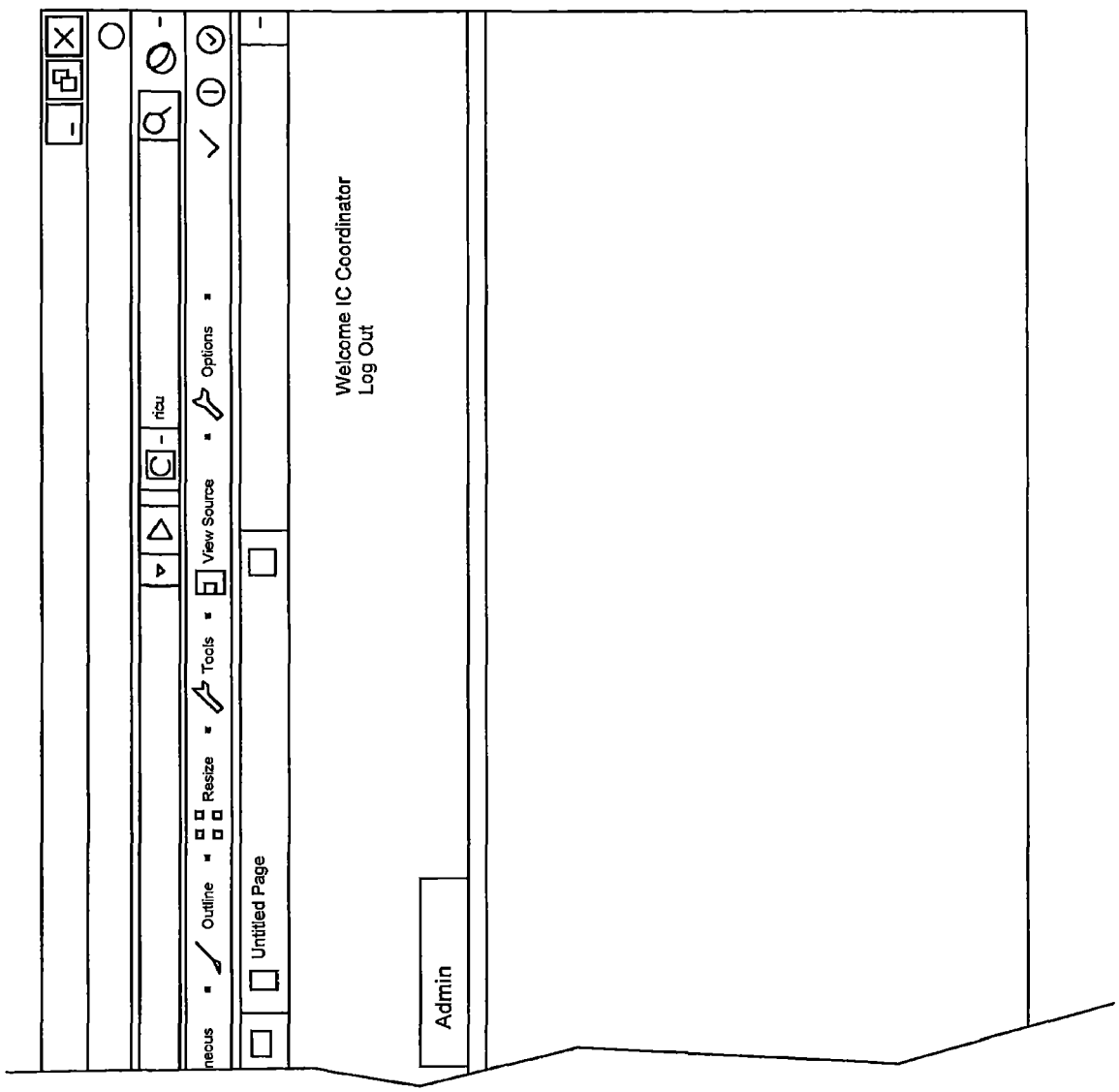
Figure 59A:
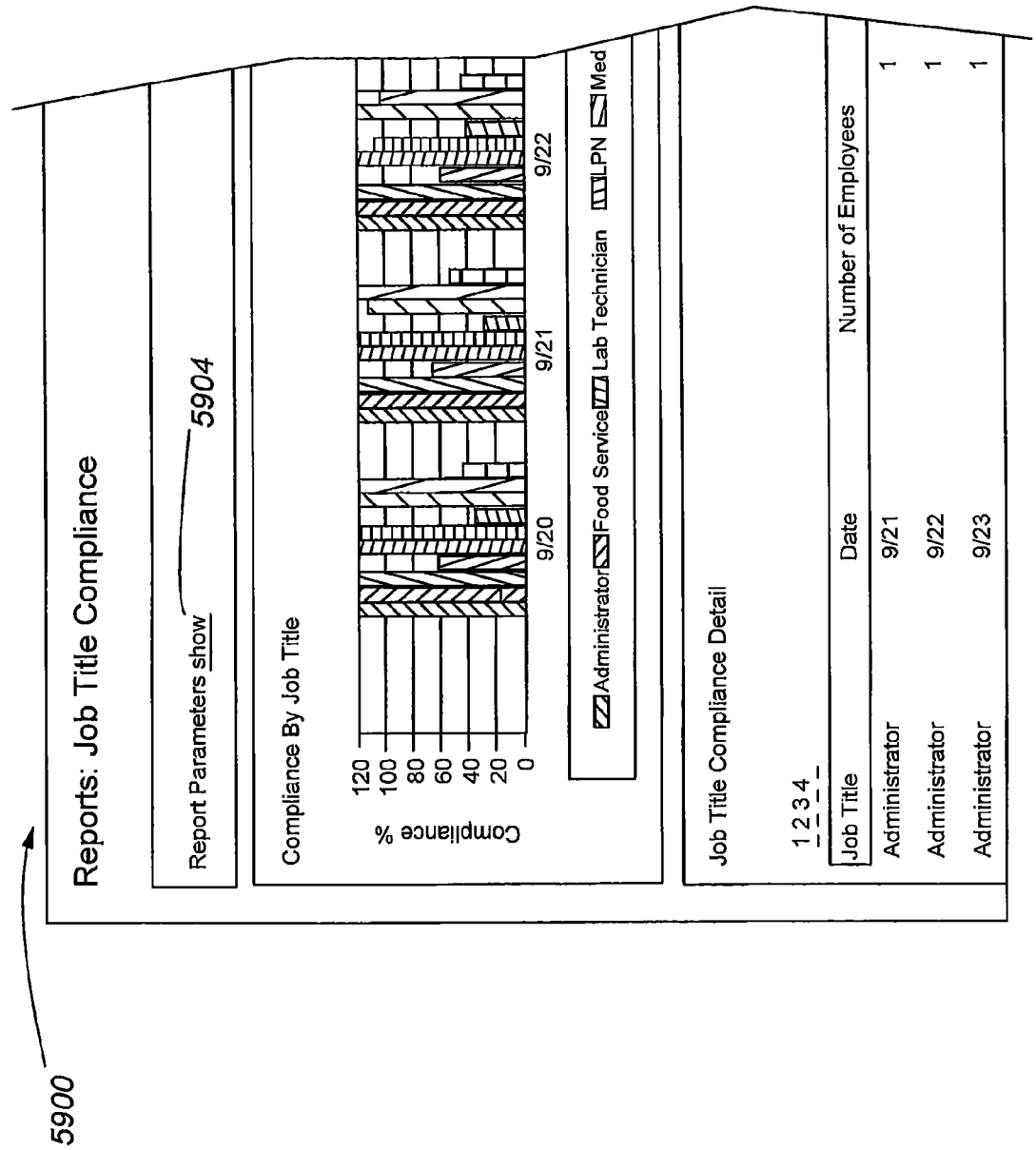
FIGS. 59A-59B is a screenshot according to an embodiment.
Figure 59B:
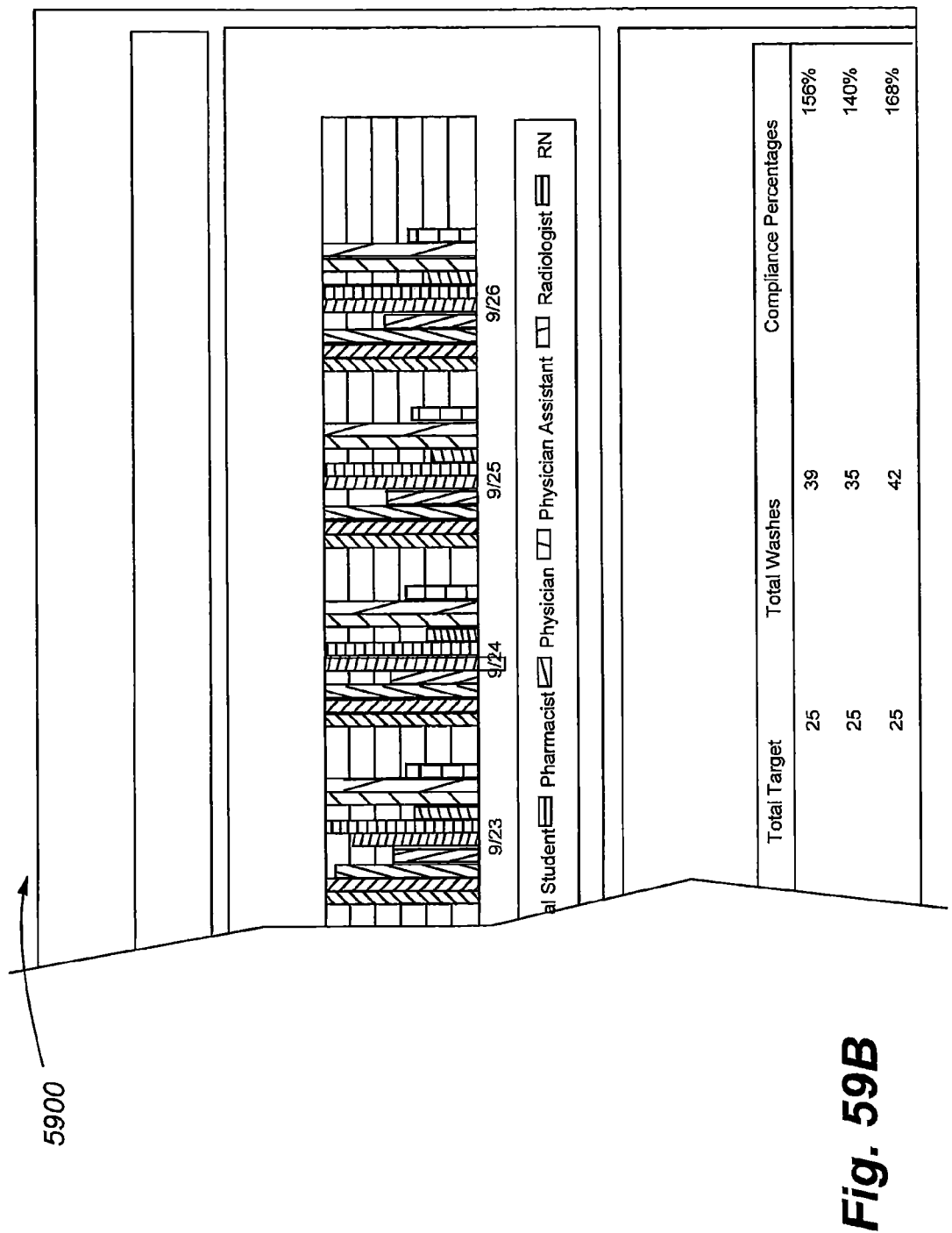

Referring to FIGS. 58A-58B, the reports tab 5308 provides three links, namely the department compliance report 5800, the job-title compliance report 5804, and the current washes report 5808. Referring to FIGS. 59A-59B, the default state of the upper half of the department compliance report 5800 is similar to the compliance by department chart in the GUI page 5300. The bottom portion of the screen has changed. It now contains a detailed compliance information spreadsheet with columns, including department, date, number of employees, total target washes, and compliance percentage. The show link 5904 permits the user to view the current report settings and parameters and edit them as desired. For example, the user can select a different set of departments, report period, and whether the report format is to be in detail or summary form. The detail format produces a report broken down by day. The summary form produces a summary report of all dates selected.

Referring to FIGS. 54A-54B and 59A-59B, the upper half of the job title compliance report 5900 looks similar to the job title compliance view in FIGS. 54A-54B. The bottom portion of the screen shot has changed, and it now contains a detailed compliance information spreadsheet with the columns, job title, date, number of employees, total target, total washes and compliance percentage. The show link 5904 permits the user to view the current report settings and parameters and edit them as desired. For example, the user can select a different set of job titles, different set of departments (for which the job titles are to be reported (e.g., physicians in the NICU), report period, and whether the report format is to be in detail or summary form, as discussed above.

The current washes report, which is also available from the quick reference 5344, displays all of the most recent washes in a detailed spreadsheet format. Displayed information includes user name, user's department, user's job title, user's employee identifier, user's badge identifier, the identifier of the wash station used, an indicator whether or not the wash was completed successfully, and the wash date.

The administrative tab 5312 permits administrators to manage various functions, including washer configuration, user management (drop, add, or edit user information (e.g., user name, user contact information, user password, user employee identification number, user badge (or RFID) number, user assigned department, employee type identifier, user job title, identities of devices associated with the user (e.g., a user work piece, a door into or out of a designated user work area, a user powered or unpowered tool, and the like), user shift times, and the like)), automated washing device management (e.g., add, drop, or edit device information (e.g., device or wash station name, device or wash station location, device or wash station type, device or wash station assigned department, device or wash station washes-per-soap bottle (currently remaining and/or original soap bottle capacity), a number of washes performed by the device, a number of washes performed by the device since the soap bottle was replaced, device maximum wash water temperature, device IP address, device IP port, and device serial number)), location management (setting up logical hierarchical relationships between locations), target management (e.g., edit the target number of washes per day for a department, job title, or user (the number of washes is of course a function of the number of hours the respective employee will work during the reporting period)), department management (e.g., add, delete, or edit a department), job-title management (e.g., add, delete, or edit a job title), and shift management (e.g., add, delete, or edit a shift).

Figure 50:
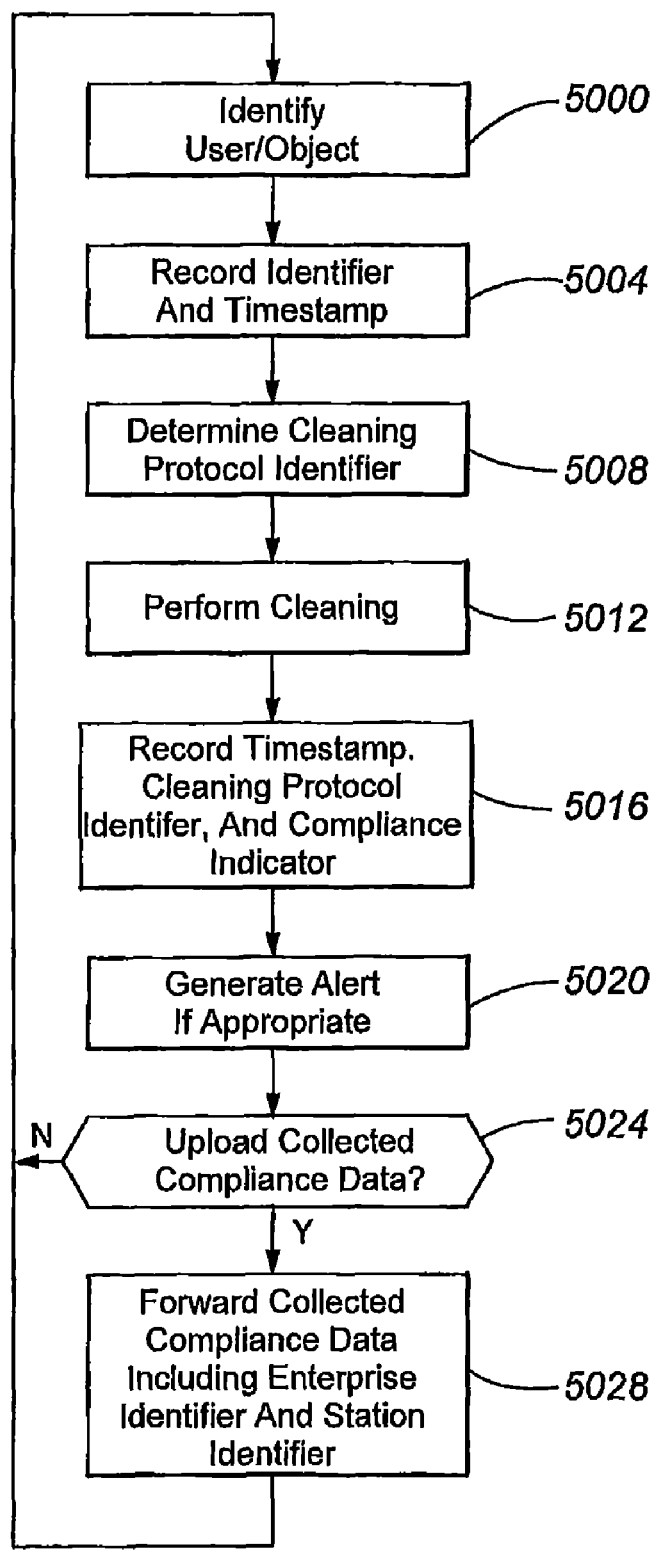
FIG. 50 is a flow chart according to an embodiment of the present invention.

The operation of the hygiene monitoring system will now be discussed with reference to FIG. 50.

In step 5000, the compliance module 316 of a selected washing station 100 identifies an object within range of the sensor. For example, an RFID tag identifier code associated with an animate or inanimate object is read by the RFID reader. Control then passes to step 5004.

In step 5004, the sensed identifier code and a first timestamp are recorded by the module 316. The first timestamp is indicative of the start time of the cleaning or washing cycle. In other configurations, the actual time that the cleaning cycle is commenced is sensed by a suitable sensor, such as an infrared sensor, motion sensor, or other type of optical or electromagnetic sensor, and recorded.

In step 5008, the module 316 maps the sensed identifier code against the lookup table of FIG. 5B and determines, for the sensed identifier code, a corresponding value for the cleaning protocol to be employed. The module 316 then configures the corresponding washing station 100 for performing the cleaning steps required by the protocol.

In step 5012, under the control of the module 316 the washing station 100 cleans the identified object according to the requirements of the cleaning protocol. In one configuration, the washing station 100 provides audible or visual instructions to the identified object or to an operator cleaning the identified object regarding the protocol requirements and senses when the various protocol steps are performed.

In step 5016, the module 316 records the sensed identifier and a second timestamp when one or more steps of the cleaning protocol is/are completed or, if the cleaning protocol steps are not completed, when the object to be cleaned is no longer within range of a sensor (e.g., the RFID reader or infrared sensor) of the washing station 100. The module 316 further records, for the sensed identifier, the protocol identifier for the corresponding protocol, and a compliance indicator (e.g., whether the protocol was successfully or unsuccessfully completed before the sensed identifier left sensor range).

In step 5020, an appropriate alert is generated depending on whether the protocol was successfully or unsuccessfully completed. The alert or warning can be provided to the object by the washing station 100.

In one configuration, the response is based on one or more of the job title, department, badge number, and/or employee identity of the noncompliant user. Different employees may have different responses, depending upon one or more of their respective histories of compliance or noncompliance with a hygiene protocol, their respective job titles, their respective departments, their respective badge numbers, and/or their respective identities. A first user may thus have a first response for failing to complete a wash successfully, and a second user a second different response for failing to complete a wash successfully. The response may be not only an audible and/or visual alert or warning but also a selective disablement of a device associated with the user. The device is identified in the user information. For example, a response to a first user failing to complete a wash successfully may be to disable a first door to a first work area (such as a clean room, food storage or preparation area, health care area, and the like) for the first user but not a second door to a different second work area while a response to a second different user failing to complete a wash successfully may not cause disablement of the first door but the second door because, for instance, the second user, and not the first user, is not designated to work in the second work area. In another example, the first user, in response to failing to complete a wash successfully, may find a device, such as an oven, which the user uses in the course of his work, to be disabled. In another example, the first user, in response to failing to complete a wash successfully, may be prevented from punching in on a time clock. In another example, a compliance monitor, in response to the first user failing to complete a wash success-fully, alerts a responsible person (such as a manager or compliance administrator) other than the first user.

In decision diamond 5024, the module 316 determines whether collected compliance data or cleaning information should be uploaded to the data network 4824 for transmission to the compliance server 4832. The trigger for uploading the information could be, for example, time-based, based on the number of washings performed by the corresponding station, or based on the available or unavailable memory capacity of the module 316 in the corresponding station. Alternatively, the trigger could be the receipt of a request from the server 4832 for the information.

When the collected compliance data is to be provided to the server 4832, the module 316 generates one or more signals containing the data and includes, in each signal, the monitored entity identifier of the corresponding monitored entity (e.g., the identifier of the enterprise operating the washing station 100) and station identifier of the washing station 100 performing the cleaning. As noted, the monitored entity identifier is unique among the monitored entities, and the station identifier among the various stations 100 operated by the corresponding monitored entity. The signal(s) are then forwarded to the compliance server 4832.

The data management module 4844, based on the enterprise identifier, forwards the signals to the appropriate compliance database 4836, or storage location(s), for storage and analysis. As will be appreciated, the module 4844 maps the monitored entity identifier against a lookup table indexing monitored entity identifiers against database address and/or storage address range. The received information is then forwarded to an interface for the corresponding database for storage. The table is further used to retrieve compliance data for an identified, monitored entity.

In another embodiment, the data management module 4844 and/or compliance filter 4820 use location information to identify appropriate compliance monitor(s) 4816a, b-p to which to report, to configure collection parameters, and/or to configure compliance reports for transmission to the identified compliance monitor(s) 4816a, b-p. The location information can be in many different forms. For example, each monitored facility of a common enterprise or each monitored enterprise is assigned geographical information indicating the physical location of the monitored entity. In another example, each monitored facility of a common enterprise or each monitored enterprise is assigned geopolitical information indicating the regulatory jurisdiction or political location of the monitored entity. By way of illustration, the political location of the facility would identify each compliance monitor 4816a, b-p to which activities at the facility must be reported. In yet another example, each washing station is assigned geographic and/or geopolitical information. In yet another example, each washing station has an embedded location module, such as a GPS or other satellite enabled locating device, which provides location coordinates. In this example, as the washing station is moved from one facility to another the location information is changed dynamically.

Using the location information, whether associated with the facility as a whole or separately with each washing station in the facility, the data management module 4844 determines the corresponding monitoring and reporting requirements for the pertinent compliance monitor(s) 4816a, b-p. This is typically done using a lookup table, such as that shown in FIG. 51.

Referring to FIG. 51, the geographic location information 5100 is mapped against compliance monitor 5102, compliance data required 5104, required reporting frequency 5108, and reporting requirements 5112. The geographic location information 5100 refers to the expression of geographical and/or geopolitical location used to signify the location of the monitored entity. As noted, the geographic location information 5100 can be satellite-enabled location coordinates, compliance monitor identifiers, city identifiers, county identifiers, state identifiers, country identifiers, and the like. The compliance monitor designation 5102 identifies the compliance monitor 4816*a, b-p* to which compliance reports are to be provided. The values in column 5102 can be values associated with the compliance monitor 916*a, b-p* (which may be an electronic address). Compliance data required 5104 refers to the information to be collected to comply with requirements of the identified compliance monitor. Compliance data required 5104 includes, for example, a number of required washes/station, percent compliance (determined on a suitable basis), number of required washes/employee, and the like. The required reporting frequency 5108 refers to how frequently compliance data/reports are to be forwarded to the identified compliance monitor. The frequency, for example, can be daily, weekly, monthly, yearly, and the like. Finally, report requirements 5112 refer to requirements for the compliance information provided to the identified compliance monitor. Report requirements 5112, for example, can refer to how the compliance data is to be transmitted to the monitor (e.g., by email, by mail, by upload/download operation over the data network 4824, and the like), the formatting and organizational requirements for the report, the entities associated with the monitor to whom the information is to be provided and each entity's address information, and the like. Other information in column 12 includes whether the information is to be encrypted and, if so, what key(s) are to be employed, the human or computer language in which the report is to be expressed (e.g., German, English, HTML, XML, and the like), and the like.

Figure 52:
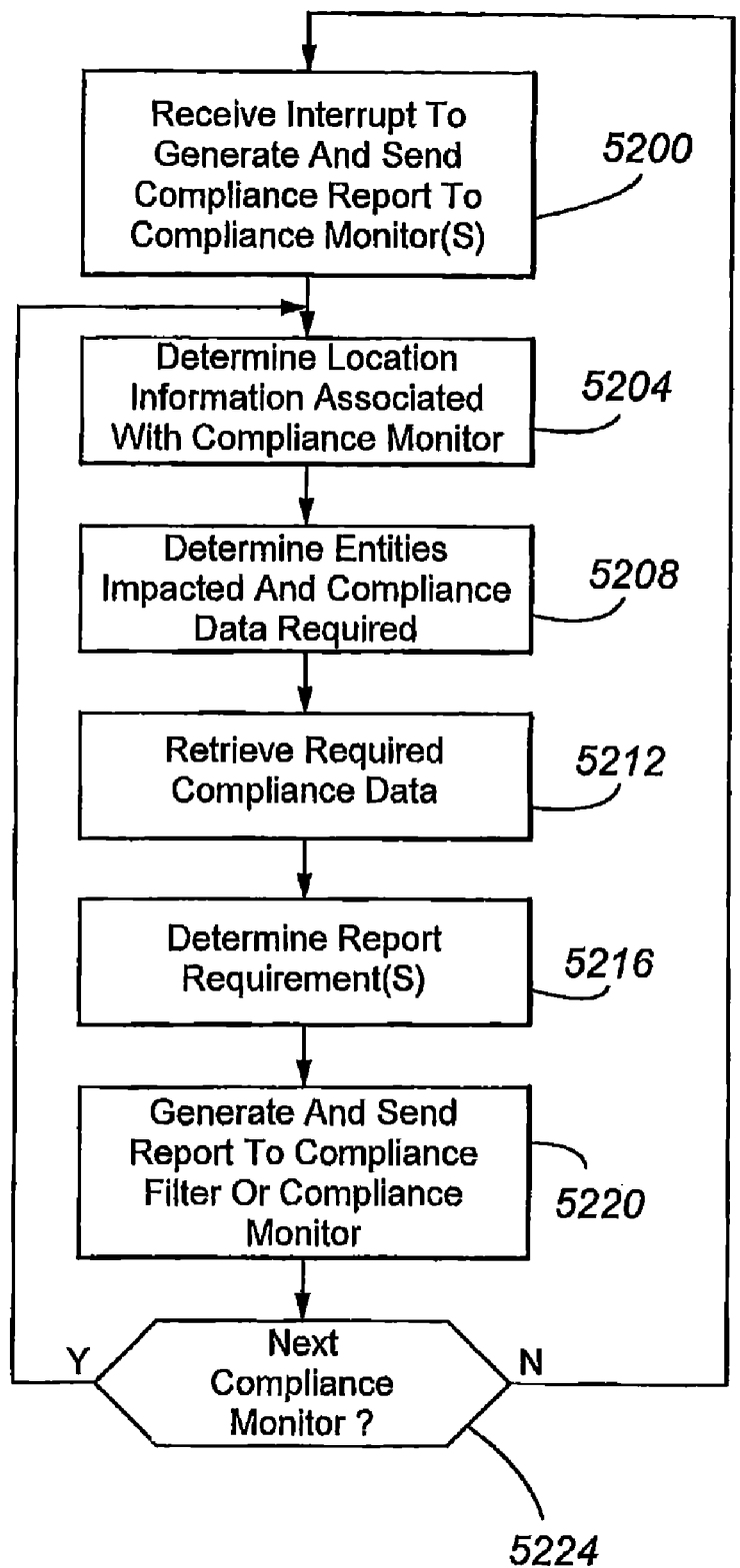
FIG. 52 is a flow chart according to an embodiment of the present invention.

The operation of this embodiment will now be discussed with reference to FIG. 52.

In step 5200, a scheduling module (not shown) generates an interrupt identifying one or more compliance monitors 916*a, b-p* requiring compliance report(s) to be provided. The interrupt is received by the data management module 4844.

In step 5204, the module 4844 determines the location information associated with a selected one of the compliance monitors referenced in the interrupt. This can be done by mapping an identifier of the selected compliance monitor against a listing of location information regulated or serviced by the selected compliance monitor 486*a, b-p*.

In step 5208, the module 4844 determines, based on the geographic location information 5100, each of the monitored entities 4804*a,b-w* monitored by the selected compliance monitor and, based on the geographic location information 5100 a monitored entity identifier for each of the identified entities, the compliance data required 5104.

In step 5212, the module 4844 retrieves the required compliance data. This is typically done iteratively on an enterprise-by-enterprise basis to avoid intermixing compliance data for different enterprises. Compliance data may be collected by querying the appropriate one of the first, second, . . . nth databases 4836*a-n* and/or obtaining compliance information from each of the first, . . . xth washing stations 100*a-x* at the subject facility for each identified enterprise.

In step 5216, the module 4844 determines the reporting requirements 5112 for the selected compliance monitor.

In step 5220, the module 4844, using the reporting requirements and compliance data obtained, generates and sends the report to the compliance filter 4820 and/or directly to the compliance monitor 4816*a, b-p*. When the report is sent to the compliance filter 4820, the filter 4820 can remove unnecessary information collected by the washing stations and forward the filtered report to the compliance monitor 4816*a, b-p*.

In decision diamond 5224, the module 4844 determines whether the interrupt identified a next compliance monitor. If not, control returns to step 5200. If so, the next compliance monitor is selected, and the module returns to step 5204.

The exemplary systems and methods of this invention have been described in relation to automated cleaning systems. However, to avoid unnecessarily obscuring the present invention, the preceding description omits a number of known structures and devices. This omission is not to be construed as a limitation of the scope of the claimed invention. Specific details are set forth to provide an understanding of the present invention. It should however be appreciated that the present invention may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as an automated washing station, or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the invention.

A number of variations and modifications of the invention can be used. It would be possible to provide for some features of the invention without providing others.

In yet another embodiment, the systems and methods of this invention can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this invention. Exemplary hardware that can be used for the present invention includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this invention is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this invention can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present invention describes components and functions implemented in the embodiments with reference to particular standards and protocols, the invention is not limited to such standards and protocols. Other similar standards and protocols not mentioned herein are in existence and are considered to be included in the present invention. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present invention.

The present invention, in various embodiments, configurations, and aspects, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments, configurations, or aspects for the purpose of streamlining the disclosure. The features of the embodiments, configurations, or aspects of the invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the invention.

Moreover, though the description of the invention has included description of one or more embodiments, configurations, or aspects and certain variations and modifications, other variations, combinations, and modifications are within the scope of the invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A washing system, comprising:
a rotatable wash cylinder to receive an appendage of a user; and
a plurality of nozzles in the rotatable wash cylinder, the plurality of nozzles to direct a cleaning fluid inwardly into an interior of the wash cylinder, wherein a depth of the wash cylinder is adjustable, whereby, in a first mode of operation, the wash cylinder has a first depth and, in a second mode of operation, the wash cylinder has a second depth, with the first depth being greater than the second depth to accommodate user appendages of differing sizes.

2. The washing system of claim 1, wherein a first set of nozzles are positioned in a cylindrical portion of the wash cylinder and a second set of nozzles are positioned in a telescopic portion of the wash cylinder and wherein a common fluid input port provides fluid to both the first and the second sets of nozzles.

3. The washing system of claim 1, wherein the wash cylinder comprises an accordion portion of variable length connected with a cylindrical portion of fixed length.

4. The washing system of claim 1, wherein the washing system comprises a memory and a processor, the memory comprising a profile of a user, the profile of the user comprising a particular depth setting of the wash cylinder and a unique identifier of the user.

* * * * *